(12) United States Patent
Nashman et al.

(10) Patent No.: US 12,245,849 B2
(45) Date of Patent: Mar. 11, 2025

(54) SYSTEM AND METHOD FOR NUCLEAR MAGNETIC RESONANCE MEASUREMENT OF BLOOD ANALYTE LEVELS

(71) Applicant: Synex Medical Inc., Toronto (CA)

(72) Inventors: Benjamin Saul Nashman, Toronto (CA); Stephen McFadyen, Toronto (CA); Martin Gajdosik, Toronto (CA)

(73) Assignee: Synex Medical Inc., Toronto (CA)

( * ) Notice: Subject to any disclaimer, the term of this patent is extended or adjusted under 35 U.S.C. 154(b) by 0 days.

(21) Appl. No.: 18/798,176

(22) Filed: Aug. 8, 2024

(65) Prior Publication Data

US 2025/0049343 A1 Feb. 13, 2025

Related U.S. Application Data

(60) Provisional application No. 63/531,405, filed on Aug. 8, 2023, provisional application No. 63/544,041, filed on Oct. 13, 2023, provisional application No. 63/544,723, filed on Oct. 18, 2023, provisional application No. 63/544,726, filed on Oct. 18, 2023.

(51) Int. Cl.
| | |
|---|---|
| *A61B 5/145* | (2006.01) |
| *A61B 5/00* | (2006.01) |
| *A61B 5/055* | (2006.01) |
| *G01R 33/20* | (2006.01) |

(52) U.S. Cl.
CPC .......... *A61B 5/055* (2013.01); *A61B 5/14532* (2013.01); *A61B 5/14546* (2013.01); *A61B 5/6826* (2013.01); *G01R 33/20* (2013.01); *A61B 2560/0223* (2013.01)

(58) Field of Classification Search
CPC . A61B 5/055; A61B 5/14532; A61B 5/14546; A61B 5/6826; A61B 2560/0223
See application file for complete search history.

(56) References Cited

U.S. PATENT DOCUMENTS

| | | | |
|---|---|---|---|
| 4,875,486 A * | 10/1989 | Rapoport | G01R 33/46 |
| | | | 324/318 |
| 5,072,732 A | 12/1991 | Rapoport et al. | |
| 6,255,929 B1 * | 7/2001 | Xu | G01R 33/381 |
| | | | 335/299 |
| 7,405,567 B2 | 7/2008 | Mcdowell | |
| 9,285,441 B1 | 3/2016 | Mcdowell | |
| 10,739,428 B2 | 8/2020 | Mcdowell | |
| 10,845,441 B1 | 11/2020 | Mcdowell | |
| 11,204,405 B1 | 12/2021 | Mcdowell | |
| 11,237,237 B2 | 2/2022 | O'Brien | |
| 2010/0201357 A1 | 8/2010 | Ogawa et al. | |

(Continued)

OTHER PUBLICATIONS

"Direct Non-Invasive Measurement of Glucose with Tabletop Magnetic Resonance Spectroscopy", Synex Medical, Oct. 10, 2023.

(Continued)

*Primary Examiner* — Eric J Messersmith
(74) *Attorney, Agent, or Firm* — Jeffrey Schox; Annabel Imbrie-Moore

(57) ABSTRACT

The nuclear magnetic resonance system can include: a set of magnets, a housing, a set of coils (e.g., receive coil, transmit coil, gradient coil, active shim coil, etc.), and a processing system. The nuclear magnetic resonance method can include: applying a pulse sequence, acquiring a signal, and processing the signal (e.g., to determine blood analyte levels).

9 Claims, 49 Drawing Sheets

(56) References Cited

U.S. PATENT DOCUMENTS

| | | |
|---|---|---|
| 2013/0154642 A1 | 6/2013 | Sueoka |
| 2016/0011290 A1* | 1/2016 | Lannello ............... A61B 5/055 600/422 |
| 2016/0120438 A1 | 5/2016 | Cima et al. |
| 2017/0299674 A1 | 10/2017 | Mcdowell |
| 2017/0325710 A1* | 11/2017 | Ryan ................... G01R 33/448 |
| 2018/0106876 A1 | 4/2018 | Nielsen et al. |
| 2019/0271749 A1 | 9/2019 | Cistola et al. |
| 2021/0121108 A1 | 4/2021 | Nashman et al. |
| 2021/0199736 A1* | 7/2021 | O'Brien ................ G01N 33/66 |
| 2021/0290319 A1 | 9/2021 | Poltaretskyi et al. |

OTHER PUBLICATIONS

"NMR Topic of the Month: the Perfect Echo Pulse Sequence", Texas A&M, https://nmr.chem.tamu.edu/pdf/tidbits/NMRTotM_202208.pdf, Aug. 2022.

"Solving the Holy Grail of Health Monitoring", Synex Medical, https://synex.substack.com/p/188746f5-066b-4f9f-a645-7a2a8ba53ee3, Nov. 9, 2023.

Ahmed, Mustafa Ahmed Ali, et al., "Robustness of dynamical decoupling sequences", arXiv:1211.5001v2, https://arxiv.org/pdf/1211.5001, Mar. 26, 2013.

* cited by examiner

Position number represents the slice position is from: 2 (1) to -8 mm (12)

TR: Repetition Time

| 90° Pulse | 90° Pulse | 90° Pulse |
|---|---|---|
| 90 | 0 | 0 |
| 270 | 0 | 180 |
| 0 | 90 | 270 |
| 180 | 90 | 90 |
| 90 | 180 | 0 |
| 270 | 180 | 180 |
| 0 | 270 | 270 |
| 180 | 270 | 90 |

Note the increased area in the glucose region as blood glucose concentration increased throughout the test.

Reference = clinical grade finger-prick

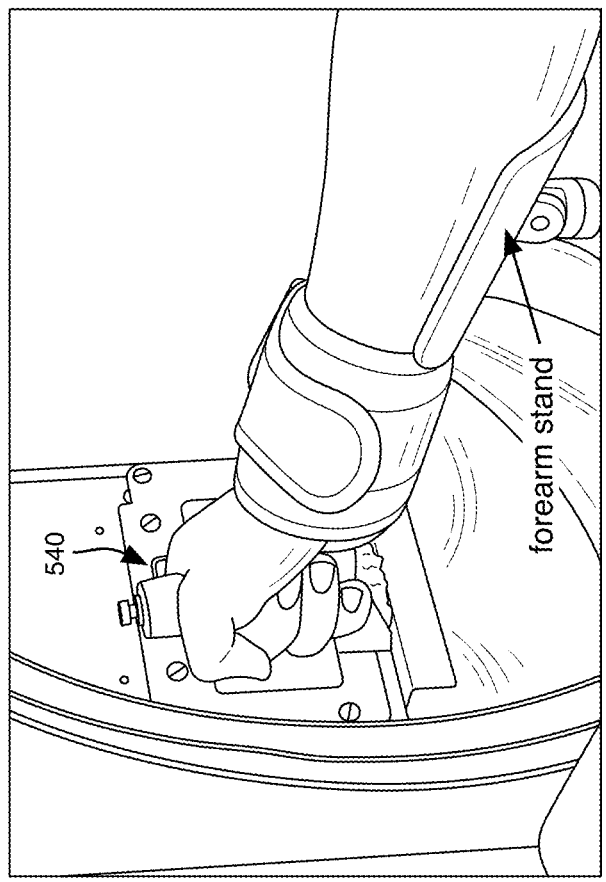
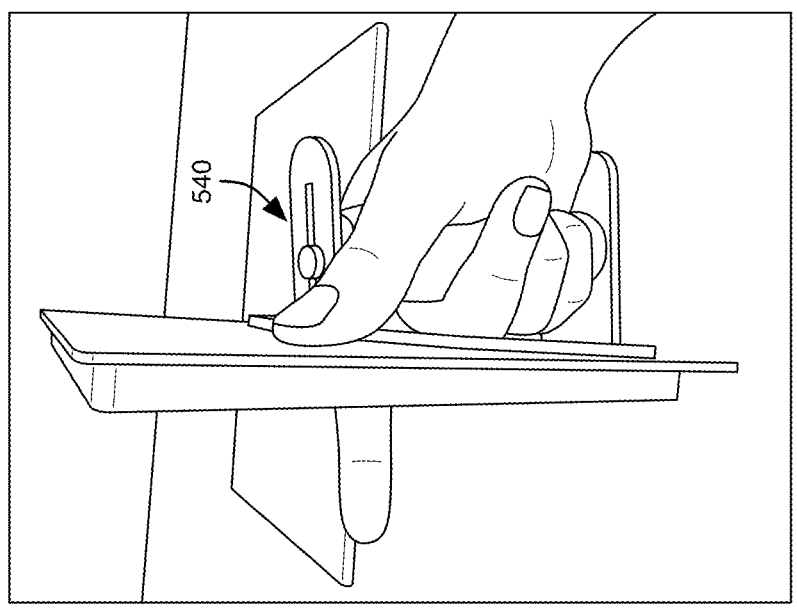
FIGURE 29B
FIGURE 29A

SYSTEM AND METHOD FOR NUCLEAR MAGNETIC RESONANCE MEASUREMENT OF BLOOD ANALYTE LEVELS

CROSS-REFERENCE TO RELATED APPLICATIONS

This application claims the benefit of U.S. Provisional Application No. 63/531,405 filed 8 Aug. 2023, U.S. Provisional Application No. 63/544,041 filed 13 Oct. 2023, U.S. Provisional Application No. 63/544,723 filed 18 Oct. 2023, and U.S. Provisional Application No. 63/544,726 filed 18 Oct. 2023, each of which is incorporated in its entirety by this reference.

TECHNICAL FIELD

This invention relates generally to the nuclear magnetic resonance field, and more specifically to a new and useful system and method for nuclear magnetic resonance measurement of blood analyte levels in the nuclear magnetic resonance field.

BRIEF DESCRIPTION OF THE FIGURES

FIGS. 29A and 29B depict specific examples of a grounding system.

DETAILED DESCRIPTION

The following description of the embodiments of the invention is not intended to limit the invention to these embodiments, but rather to enable any person skilled in the art to make and use this invention.

1. Overview

Figure 1:
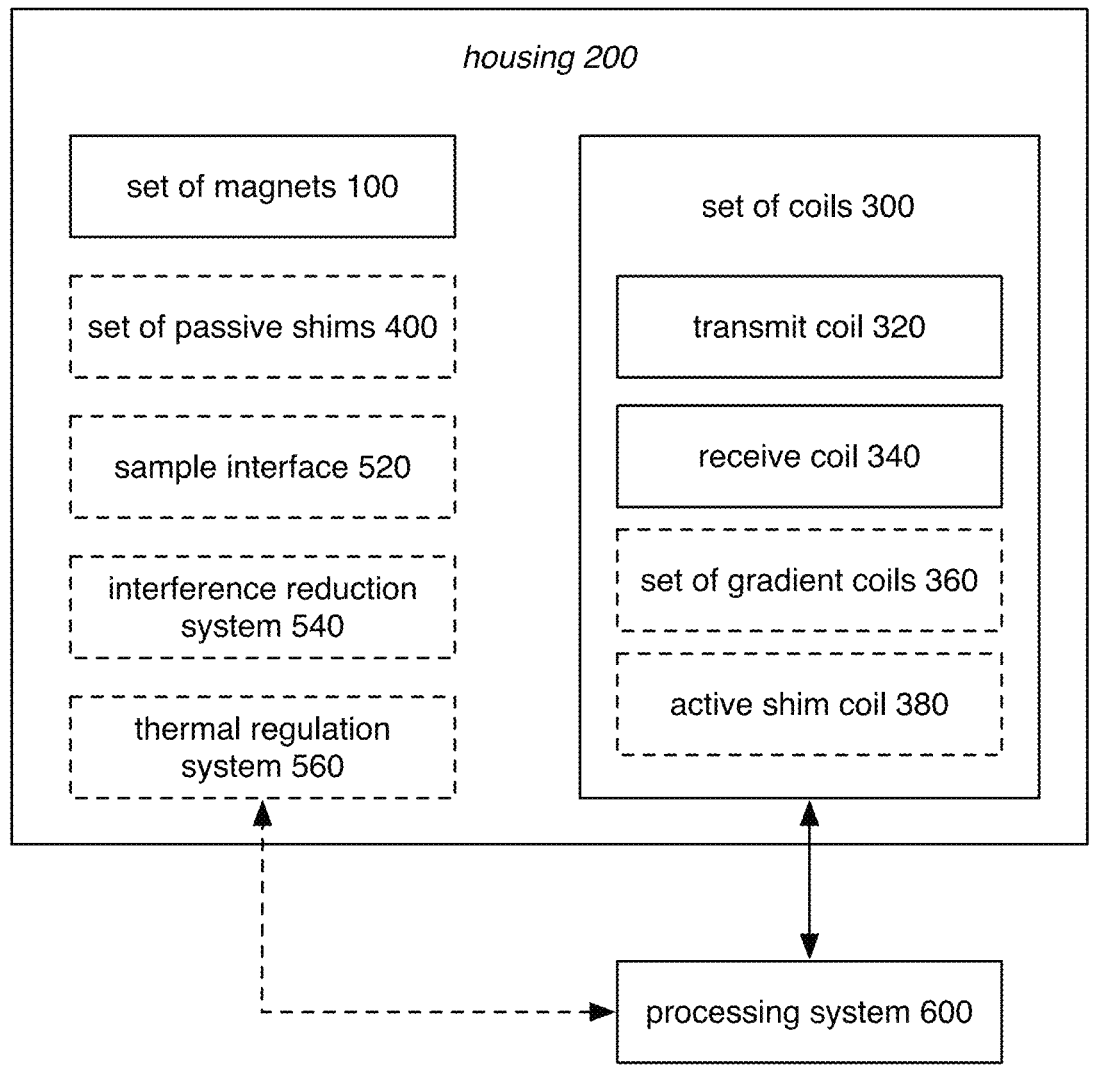
FIG. 1 is a schematic representation of a variant of the system.

As shown in FIG. 1, the system 10 can include: a set of magnets 100, a housing 200, a set of coils 300, and a processing system 600. However, the system 10 can additionally or alternatively include any other suitable components.

Figure 2:
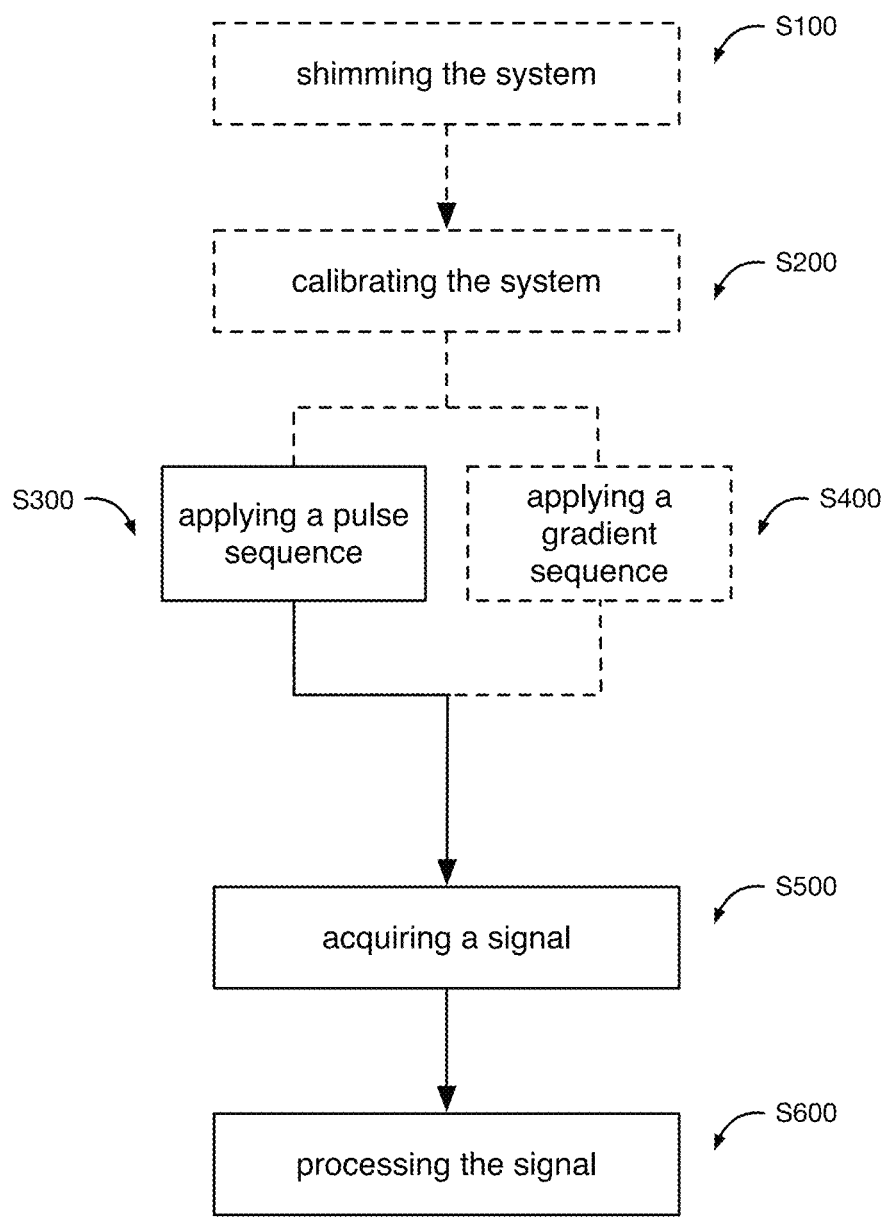
FIG. 2 is a schematic representation of a variant of the method.

As shown in FIG. 2, the method can include: applying a pulse sequence, acquiring a signal, and processing the signal. However, the method can additionally or alternatively include any other suitable steps.

In variants, the system 10 and method can function to measure blood analyte levels within a sample (e.g., a finger). The system 10 and method can additionally or alternatively function to image a sample (e.g., a finger). For example, the system 10 can function as a magnetic resonance imaging (MRI) device.

2. Examples

In an example, the system includes a portable NMR device (e.g., a desktop NMR device) that can measure blood analyte levels (e.g., glucose levels) within a user's finger. The NMR device can include, within a single housing enclosure: a set of magnets, a surface receive coil, a solenoid transmit coil, a set of gradient coils (e.g., multi-axis), an active shim coil, passive shims (e.g., button shims, ink shims, etc.), a sample interface, and a processing system. In an example, the set of magnets includes an array of magnets arranged around a bore. In a specific example, a cross-section of the bore is oblong, with first dimension (e.g., the major axis, in the case of an elliptic cylindrical bore) larger than a second dimension (e.g., the minor axis, in the case of an elliptical cylindrical bore). In an example, the sample interface interfaces with the receive coil such that, when the user inserts their finger into the sample interface, the sample interface facilitates positioning of the finger pulp against the surface receive coil, where the central axis of the surface receive coil intersecting with the pulp of the finger. The sample interface can include material of comparable susceptibility to finger tissue.

Measuring blood analyte levels using the system can include: performing one or more calibration scans on the user's finger and/or another sample (e.g., passive shimming calibration, active shimming calibration, target region calibration, etc.), performing a measurement scan of the user's finger, and analyzing the acquired signal to determine analyte levels in the sample. In an example, the measurement scan includes an excitation pulse, a non-selective train of refocusing pulses (e.g., non-selective Carr-Purcell-Meiboom-Gill (CPMG)), and a selective train of refocusing pulses (e.g., CPMG with Localization through Adiabatic SElective Refocusing (LASER)). In a specific example, the selective train of refocusing pulses can include three axis selection, which can be used to select a voxel of the finger tissue within the pulp of the finger, away from the bone/tissue interface.

3. Technical Advantages

Variants of the technology can confer one or more advantages over conventional technologies.

First, conventional methods of NMR measurements of blood analytes require large, heavy NMR systems to maintain magnetic field homogeneity over a given region of interest (ROI). These NMR systems cannot be significantly scaled down in size (e.g., to less than 1,000 $cm^3$ volume, to less than 5 kg weight, etc.), as this would result in an ROI that is too small for accurate biometric parameter measurements due to their high ratio of overall volume to ROI volume. Additionally, small manufacturing errors compound as NMR systems decrease in size, resulting in a significant decrease in magnetic field homogeneity and thus a decrease in measurement sensitivity. Variants of the technology can reduce the size and weight of an NMR biometric measurement system. In a first example, the system can measure blood analytes (e.g., metabolites) in vivo using low magnetic field strength (e.g., less than 1.5T, less than 1T, less than 0.75T, less than 0.5T, etc.), which can enable the use of smaller, permanent magnets. In a second example, the system can implement passive shimming (e.g., localized shimming) and/or active shimming to ensure a homogenized magnetic field ROI that is large enough (e.g., larger than 1 mm, larger than 5 mm, larger than 10 mm, etc.) to accurately measure biometric parameters of a human appendage (e.g., a human finger) while being light enough to be a portable or desktop system.

Second, variants of the technology can account for tissue variations within the sample (e.g., the outer layers of the finger pulp have a higher concentration of water, the deeper areas of the finger pulp have a higher fat:water ratio, etc.). In an example, slice selection can be used to avoid regions at or near the bone/tissue interface (with strong susceptibility gradients) and/or to select a target region (e.g., target voxel) of the sample.

Third, users across a population can have different NMR responses (e.g., total signal at long echo times), different grounding abilities (e.g., different electrical properties, a degree of grounding that can be achieved, etc.), different temperatures, and/or different tissue compositions (e.g., amount of blood). Variants of the technology can account for this variation between users. In a first example, a calibration can be performed for each user (e.g., to identify a target region for slice selection, to perform active shimming, etc.). In a second example, a sample interface can be used to reduce the volume of air between the sample and the receive coil. In a third example, a heater can be used to maintain the sample at a target temperature.

Fourth, the volume of blood analytes in the finger pulp is comparatively low relative to the volume of lipids and water. Variants of the technology can minimize the contribution of lipids and water to the measured signal response. The inventors have discovered that analytes have different relaxation rates than lipids and water (e.g., different relaxation rates than lipids and water in the finger at lower magnetic field strengths). In a first example, a subset of analytes (e.g., MSM) relax slower than lipids and water (e.g., longer T2 relaxation). In a specific example, a pulse sequence with a T2 filter can be used to detect analyte signals in long T2 echos while minimizing water and/or lipid signals. In a second example, a subset of analytes (e.g., glucose) relaxes faster than lipids and water (e.g., faster T1 relaxation).

Fifth, variants of the technology can measure blood analyte levels in a sample where the blood analyte exhibits J-coupling (e.g., above a threshold value). For example, the pulse sequence applied to the sample can include sequence parameters designed to refocus the J-coupling evolution. In a specific example, the pulse sequence can include a train of refocusing pulses with a loop time below a threshold value (e.g., 50 ms, 30 ms, 20 ms, 15 ms, 10 ms, 5 ms, etc.).

Sixth, variants of the technology can measure blood analyte levels in a sample where the blood analyte has similar T2 relaxation constant to lipids. For example, the pulse sequence applied to the sample can exclude lipid suppression sequences. In a specific example, the pulse sequence can include a T2 filter that does not filter lipid signals (e.g., does not filter a majority of the lipid signals).

However, further advantages can be provided by the system and method disclosed herein.

4. System

As shown in FIG. 1, the system 10 can include: a set of magnets 100, a housing 200, a set of coils 300, and a processing system 600. The system 10 can optionally include a set of passive shims 400, a sample interface 520, an interference reduction 540, a thermal regulation system 560, a user device, a user interface, and/or any other suitable components. Examples of the system 10 are shown in FIGS. 8A-8L.

Figure 24:
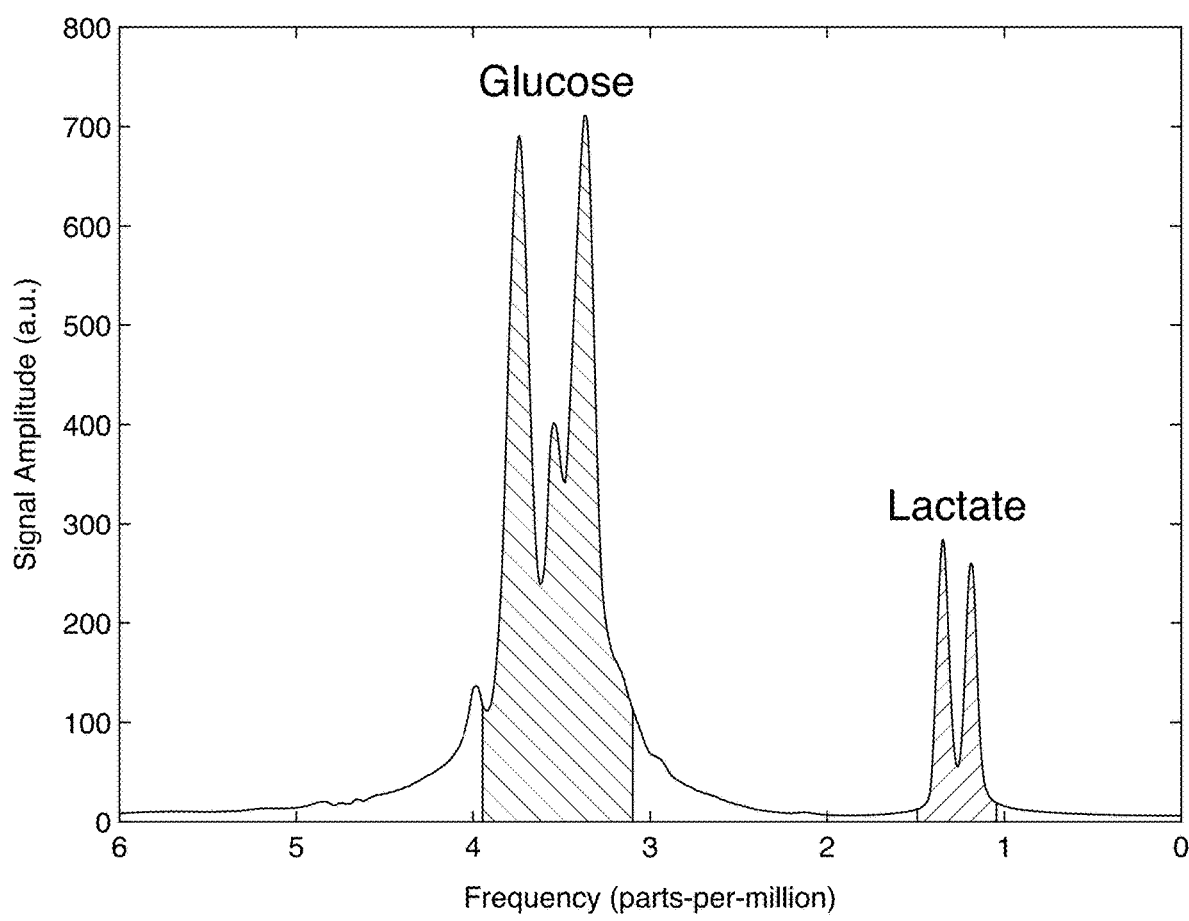
FIG. 24 depicts an example signal (e.g., spectrum) produced by a mixture of glucose and lactate.

The system 10 can be used with one or more samples. For example, the system 10 can characterize analyte levels (e.g., concentration or other quantification of the analyte) in the sample(s). The sample preferably includes a body region of a user, but can alternatively include any other in vivo sample, an in vitro sample, an inanimate sample (e.g., liquid reference sample, a phantom, etc.), and/or any other sample. The body region can include a digit (e.g., finger, toe, etc.), an extremity (e.g., arm, leg, wrist, etc.), any other appendage, and/or other body region. Examples of analytes in the sample include: glucose, methylsulfonylmethane (MSM), cholesterol, lactate, any blood analyte (e.g., blood metabolite), a proxy for an analyte (e.g., glucose proxy), any analyte exhibiting J-coupling, and/or any other component. An example signal (e.g., magnetic resonance spectrum) produced by a mixture of glucose and lactate is shown in FIG. 24. In a specific example, the system 10 can measure a signal from the analyte itself (e.g., not a proxy for the analyte).

The set of magnets 100 functions to generate a magnetic field for nuclear magnetic resonance (NMR) measurements of the sample. NMR measurements can include NMR spectroscopy measurements and/or magnetic resonance imaging (MRI) measurements. The set of magnets 100 can optionally be mounted to the housing 200. The set of magnets 100 can include one or more magnets (e.g., at least 6, at least 12, at least 24, at least 48, at least 100, at least 112, any range or value therebetween, etc.). The set of magnets 100 preferably includes permanent magnets, but can additionally or alternatively include temporary magnets. The material of each magnet in the set of magnets 100 can be iron, cobalt, nickel, neodymium, alloys thereof, and/or any other material.

Figure 3A:
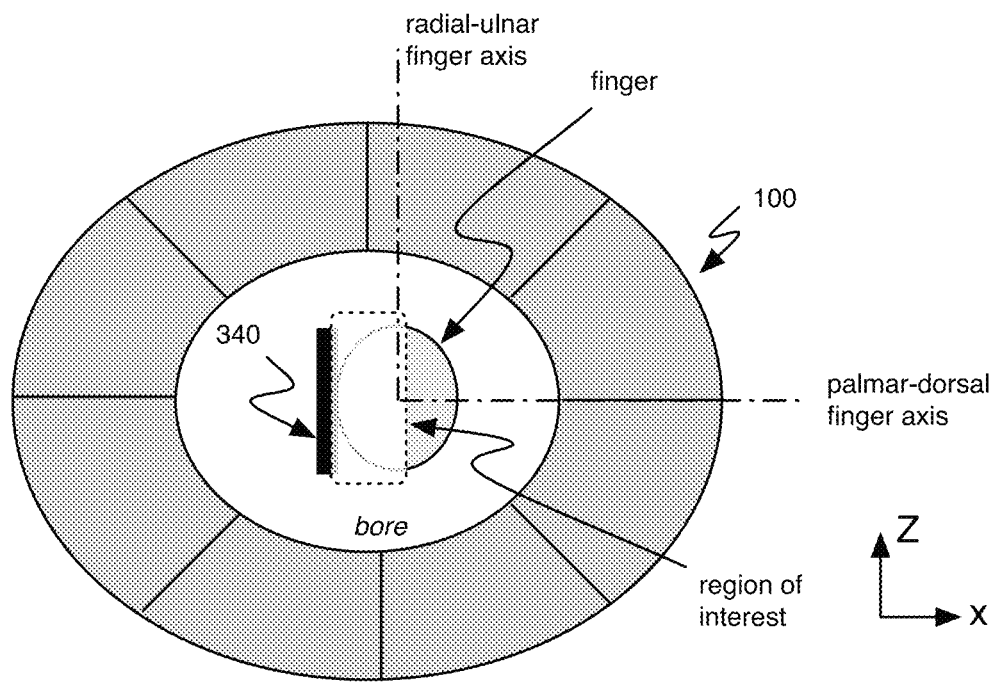
FIGS. 3A and 3B are cross-sectional views of an example of the system, illustrating a region of interest (ROI) within the bore.
Figure 3B:
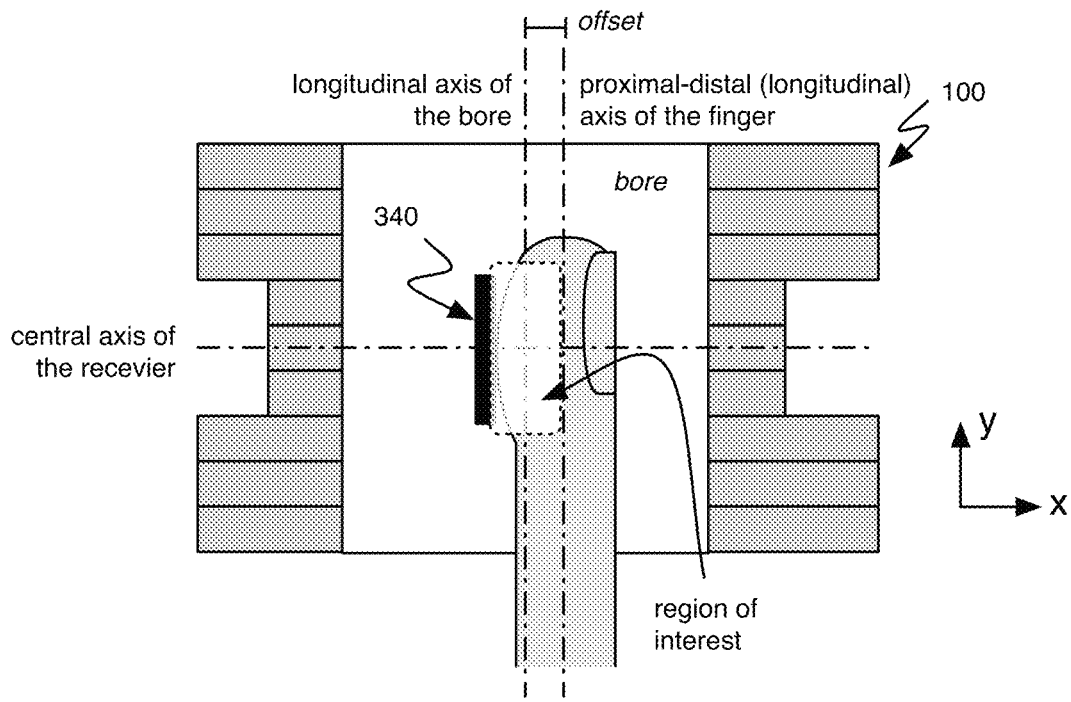

The set of magnets 100 can optionally apply a magnetic field over a region of interest (ROI). Examples are shown in FIG. 3A and FIG. 3B. In an example, the ROI can be a sphere (e.g., a diameter-spherical volume (DSV)), a rectangular prism (e.g., a slab), a rounded rectangular prism, an oblate spheroid, and/or any other shape. The ROI is preferably nonspherical, but can alternatively be spherical. The width (e.g., thickness) of the ROI (e.g., width along the x-axis, where the longitudinal axis of the bore is the y-axis) can be between 0.5 mm-50 mm or any range or value therebetween (e.g., 1 mm-10 mm, approximately 5 mm, etc.), but can alternatively be less than 0.5 mm or greater than 50 mm. The length of the ROI (e.g., length along the y-axis) can be between 1 mm-100 mm or any range or value therebetween (e.g., 5 mm-50 mm, 10 mm-20 mm, approximately 15 mm, etc.), but can alternatively be less than 1 mm or greater than 100 mm. The height of the ROI (e.g., height along the z-axis) can be between 1 mm-100 mm or any range or value therebetween (e.g., 5 mm-20 mm, approximately 10 mm, etc.), but can alternatively be less than 1 mm or greater than 100 mm. The width of the ROI (e.g., along the central axis of the surface coil) is preferably less than the height and/or the length, but can alternatively be equal to or greater than the width and/or the length. The height of the ROI is preferably substantially similar to the length, but can alternatively be substantially different. The ROI volume can be between 0.5 $mm^3$-50 $cm^3$ or any range or value therebetween (e.g., 2 $mm^3$-5 $cm^3$, 500 $mm^3$-1000 $mm^3$, 50 $mm^3$-2 $cm^3$, etc.), but can alternatively be less than 0.5 $mm^3$ or greater than 50 $cm^3$.

The ROI preferably overlaps with a target region of the sample, but can alternatively be otherwise configured relative to a sample. For example, the target region can be within the ROI. The target region (e.g., volume of interest) can be a slice, a column, a voxel, and/or any other volume of interest. A width of the target region (e.g., along a dorsal-palmar axis of the finger) can be between 0.1 mm-15 mm or any range or value therebetween (e.g., in the x-direction, 0.5 mm-4 mm, 2 mm-3 mm, 1 mm, 2 mm, 3 mm, 4 mm, 5 mm, less than 5 mm, less than 10 mm, less than 15 mm, etc.), but can alternatively be less than 0.1 mm or greater than 15 mm. A length of the target region (e.g., in the y-direction, along a proximal-distal axis of the finger, along a longitudinal axis of the finger, along a longitudinal axis of the bore, etc.) can be between 0.1 mm-20 mm or any range or value therebetween (e.g., 5 mm-15 mm, 5 mm, 8 mm, 10 mm, 12 mm, 15 mm, greater than 2 mm, greater than 5 mm, greater than 10 mm, less than 10 mm, etc.), but can alternatively be less than 0.1 mm or greater than 20 mm. A height of the target region (e.g., in the z-direction, along a radial-ulnar axis of the finger, etc.) can be between 0.1 mm-20 mm or any range or value therebetween (e.g., 5 mm-15 mm, 5 mm, 8 mm, 10 mm, 12 mm, 15 mm, greater than 2 mm, greater than 5 mm, greater than 10 mm, less than 10 mm, etc.), but can alternatively be less than 0.1 mm or greater than 20 mm. In a specific example, the width of the target region (e.g., along a dorsal-palmar axis of the finger) is less than the length of the target region (e.g., along a radial-ulnar axis of the finger). In a specific example, the width of the target region (e.g., along a dorsal-palmar axis of the finger) is less than the height of the target region (e.g., along a proximal-distal axis of the finger). In a specific example, the target region of the finger is a voxel (e.g., where the set of gradient coils 360 includes three gradient coils corresponding to three directions), wherein a width of the voxel along a dorsal-palmar axis of the finger is less than a length of the voxel along a radial-ulnar axis of the finger and is less than a length of the voxel along a proximal-distal axis of the finger. A volume of the target region can be between 0.001 mL-100 mL or any range or value therebetween, but can alternatively be less than 0.001 mL or greater than 100 mL.

Figure 4A:
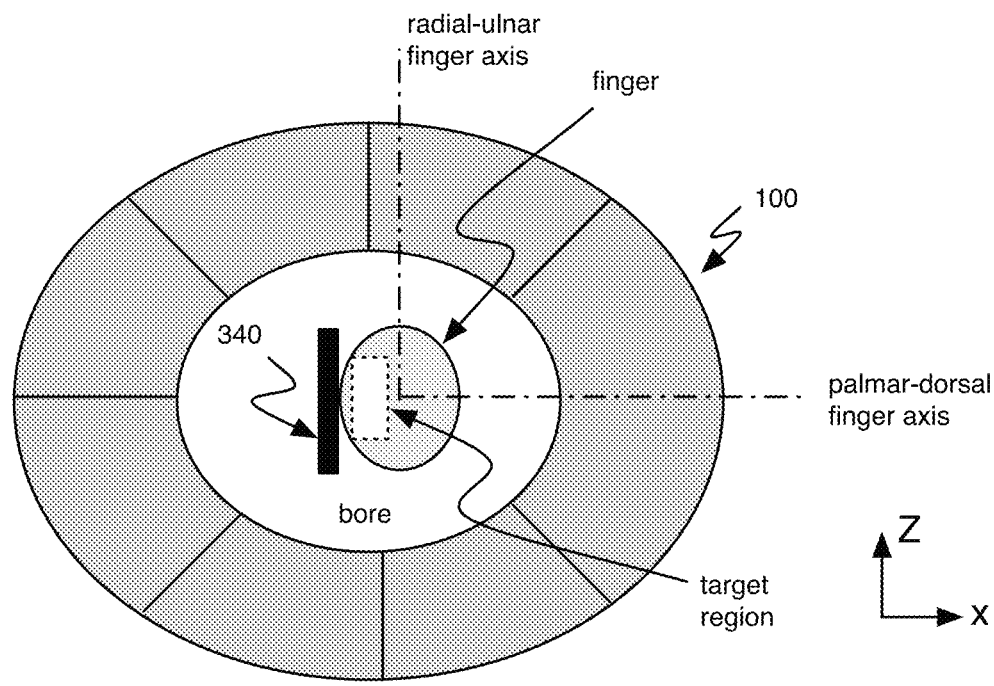
FIGS. 4A and 4B are cross-sectional views of an example of the system, illustrating a target region within the sample (e.g., a finger).
Figure 4B:
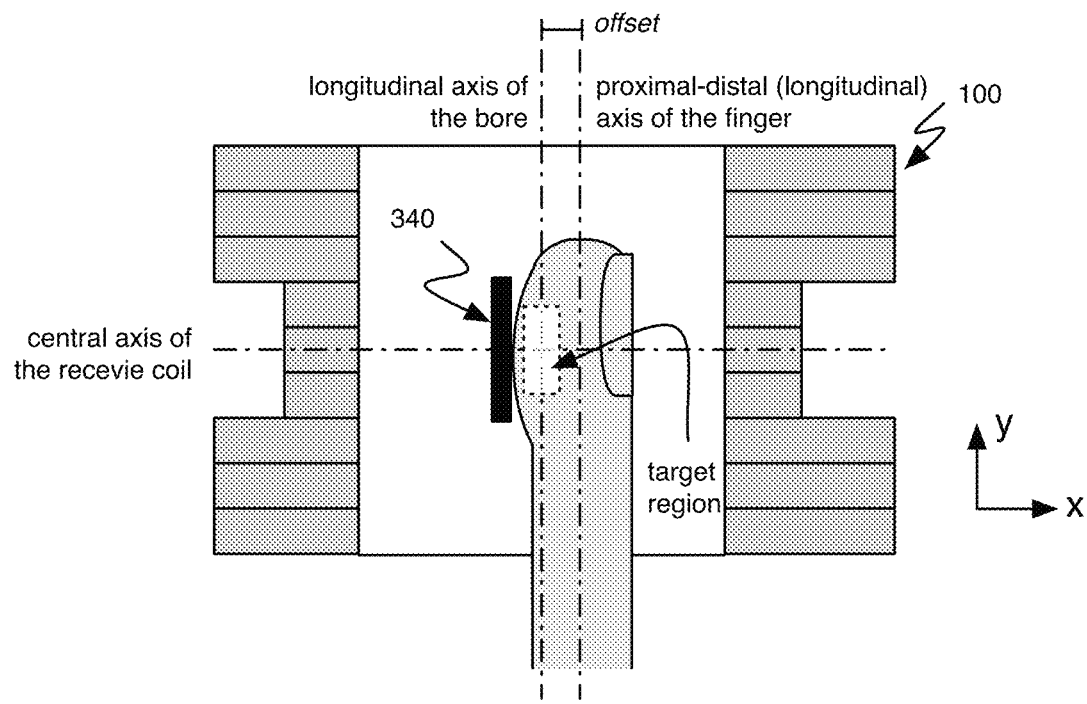

In specific examples, the target region can include (e.g., be located within and/or overlap with): the pulp of a finger (e.g., including tissue from the periosteum of the distal phalanx to the epidermis), the fingertip pad, the dermis of a finger, the hypodermis of a finger, the fingertip, and/or any other region of the finger. In a specific example, for a finger sample, the target region is preferably between 0 mm-10 mm (e.g., 0.05 mm-5 mm, less than 10 mm, less than 7 mm, less than 5 mm, less than 2 mm, greater than 0.5 mm, greater than 1 mm, any range or value therebetween, etc.) from the pulp surface (within the pulp), but can alternatively be less than 0.05 mm or greater than 10 mm from the pulp surface (e.g., fingertip pad surface). In another specific example, for a finger sample, the target region is preferably between 0.05 mm-10 mm (e.g., any range or value therebetween, 0.1 mm-5 mm, greater than 0.1 mm, greater than 0.5 mm, greater than 1 mm, etc.) from the distal phalanx, but can alternatively be less than 0.05 mm or greater than 10 mm from the distal phalanx. Examples of target regions are shown in FIG. 4A and FIG. 4B.

The field strength of the magnetic field within the ROI can be between 0.05 Tesla-2 Tesla or any range or value therebetween (e.g., 0.1 Tesla-1 Tesla, 0.25 Tesla-0.75 Tesla, 0.5 Tesla, 0.6 Tesla, less than 1 Tesla, less than 0.75 Tesla, etc.), but can alternatively be less than 0.05 Tesla or greater than 2 Tesla. The uniformity of the magnetic field within the ROI can be less than: 3000 ppm, 2000 ppm, 1500 ppm, 1200 ppm, 1000 ppm, 500 ppm, and/or any other base uniformity value such that one or more shimming systems and/or methods can correct the final uniformity of the magnetic field to below a threshold (e.g., as described in S100).

The set of magnets 100 can include one or more magnets arranged around a bore (e.g., where the set of magnets 100 defines the bore). The sample can optionally be positioned within the bore for NMR measurements.

As used herein, the y-axis is defined as aligning with the longitudinal axis of the bore. The coordinates, as used herein, are intended only as a reference and are not intended to restrict the orientation of the system 10 relative to a global coordinate system. The system 10 can be arranged in any orientation (e.g., where the x-axis corresponds to a vertical axis, where the y-axis corresponds to a vertical axis, where the z-axis corresponds to a vertical orientation, etc.).

In a specific example, the bore extends along the y-axis, and a finger sample is inserted in the bore such that the pulp of the finger is facing in the negative x-direction. However, the pulp of the finger can alternatively face the positive x-direction, the positive or negative z-direction, and/or any other direction. The proximal-distal axis of the finger (e.g., the longitudinal axis of the finger) can optionally be approximately parallel to the longitudinal axis of the bore. The proximal-distal axis of the finger (e.g., the longitudinal axis of the finger) can optionally be offset from the longitudinal axis of the bore (e.g., offset by at least 0.1 mm, at least 0.2 mm, at least 0.5 mm, at least 1 mm, at least 2 mm, at least 5 mm, etc.). It a specific example, the target region of the finger overlaps with the longitudinal axis of the bore.

In a first variant, the set of magnets 100 can include two magnets arranged on opposing sides of the bore (e.g., as a dipole). In a second variant, the set of magnets 100 can include an array of magnets (e.g., a ring of magnets, any toroidal arrangement of magnets, an annular array of magnets, etc.), including one or more magnets arranged around the bore (e.g., arranged arcuately around the bore, defining the bore, etc.). In a first embodiment, a cross-section of the bore (e.g., in the xz plane; in a plane perpendicular to a longitudinal axis of the bore) is circular. In an illustrative example, the set of magnets 100 forms a Halbach array. In a second example, a cross-section of the bore (e.g., in the xz plane; in a plane perpendicular to a longitudinal axis of the bore) is noncircular. In a specific example, the cross-section of the bore is oblong (e.g., elongated in a dimension). For example, the cross-section of the bore can be elongated in the x-direction (e.g., along the central axis of the surface coil, along the dorsal-palmar axis of the finger, etc.). In a specific example, the cross-section of the bore can be elliptical (e.g., the set of magnets 100 includes an elliptical arrangement of magnets).

The width of the bore (e.g., width along the x-axis, where the longitudinal axis of the bore is the y-axis; width along the central axis of the surface coil) can be between 10 mm-500 mm or any range or value therebetween (e.g., 15 mm-100 mm, 20 mm-40 mm, etc.), but can alternatively be less than 10 mm or greater than 500 mm. The height (e.g., height along the z-axis, where the longitudinal axis of the bore is the y-axis) can be between 10 mm-500 mm or any range or value therebetween (e.g., 15 mm-100 mm, 20 mm-40 mm, etc.), but can alternatively be less than 10 mm or greater than 500 mm. The width of the bore is preferably greater than the height of the bore, but can alternatively be less than the height of the bore. In a specific example, the width of the bore along a first axis (e.g., wherein the first axis is parallel to the central axis of the surface coil) is greater than a height of the bore along a second axis (e.g., wherein the second axis is perpendicular to the first axis and perpendicular to a longitudinal axis of the bore). The height of the set of magnets 100 can be between 15 mm-1000 mm or any range or value therebetween (e.g., 20 mm-500 mm, 30 mm-100 mm, 60 mm-80 mm, etc.), but can alternatively be less than 15 mm or greater than 1000 mm. The width of the set of magnets 100 can be between 15 mm-1000 mm or any range or value therebetween (e.g., 20 mm-500 mm, 30 mm-100 mm, 60 mm-80 mm, etc.), but can alternatively be less than 15 mm or greater than 1000 mm. The width of the set of magnets 100 is preferably greater than the height of the set of magnets 100, but can alternatively be less than the height of the set of magnets 100. In a specific example, the width of the set of magnets 100 along a first axis (e.g., wherein the first axis is parallel to the central axis of the surface coil) is greater than a height of the set of magnets 100 along a second axis (e.g., wherein the second axis is perpendicular to the first axis and perpendicular to a longitudinal axis of the bore). The length of the bore and/or the length of the set of magnets 100 (e.g., along the y-axis) can be between 15 mm-1000 mm or any range or value therebetween (e.g., 20 mm-500 mm, 30 mm-100 mm, 60 mm-80 mm, etc.), but can alternatively be less than 15 mm or greater than 1000 mm.

The set of magnets can optionally include one or more segments. For example, each segment can include an array of magnets, wherein the segments can be stacked longitudinally (e.g., along the y-axis), forming a continuous bore. In a specific example, each segment can include one or more magnets arranged around the bore (e.g., a toroidal arrangement of magnets). The segments can be uniform (e.g., the same arrangement of magnets, the same overall geometry, the same geometry of constituent magnets, the same magnetic field properties, the same mass, etc.) or nonuniform (e.g., a different arrangement of magnets, a different overall geometry, a different geometry of constituent magnets, different magnetic field properties, a different mass,). The set of magnets 100 and/or segments therein can have two or more substantially identical magnets and/or two or more magnets that are not substantially identical. Substantially identical magnets can be substantially identical in their material, mass, geometry (e.g., shape, dimensions, etc.), magnetic field properties (e.g., magnetic field strength, magnetic field shape, etc.), and/or any other parameter.

However, the set of magnets 100 can be otherwise configured.

The housing 200 functions to connect and/or mount components of the system 10. In an example, the housing 200 can include a sample aperture (e.g., an aperture within the bore) extending through all or part of the housing 200 (e.g., along the y-axis). The bore and/or the sample aperture can be configured to receive the sample. The housing 200 can encapsulate (or otherwise retain): the set of magnets 100, the set of coils 300, all or part of the processing system 600, and/or any other system component. The housing can optionally include or retain the sample interface 520. In a specific example, the housing 200 can include a single chassis containing both: magnetic field components (the set of magnets 100 and the set of coils 300) and electronic components (e.g., all or part of the processing system 600). In this example, the magnetic field components are preferably separated and/or shielded from the electronic components, but can alternatively be otherwise configured.

Figure 30A:
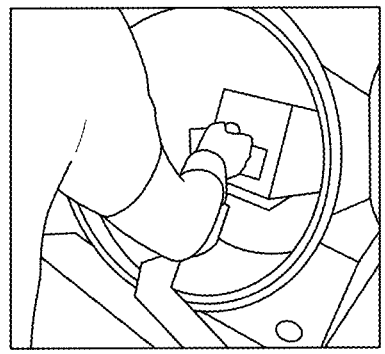
FIGS. 30A-30N depict illustrative examples of the system.
Figure 30B:
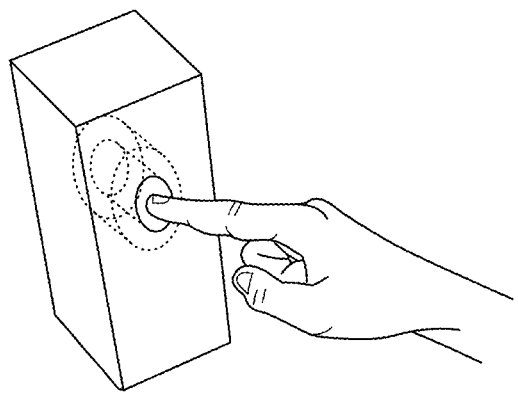
Figure 30C:
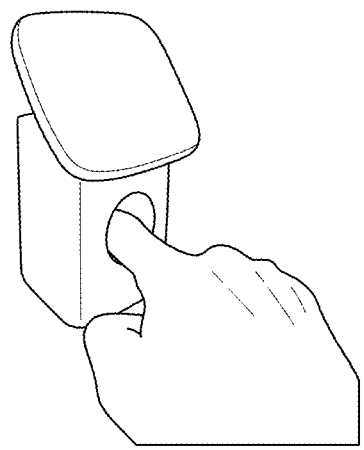
Figure 30D:
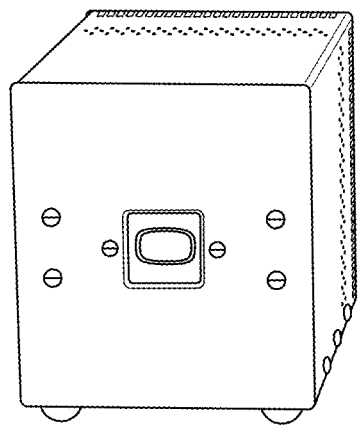
Figure 30E:
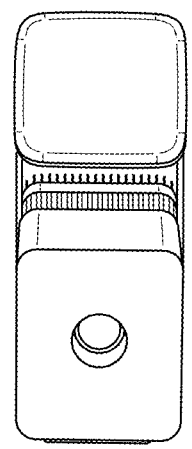
Figure 30F:
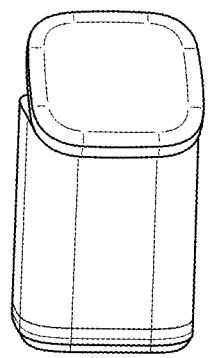
Figure 30G:
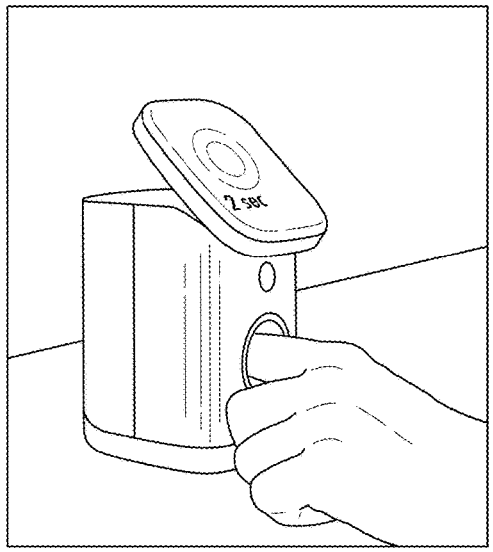
Figure 30I:
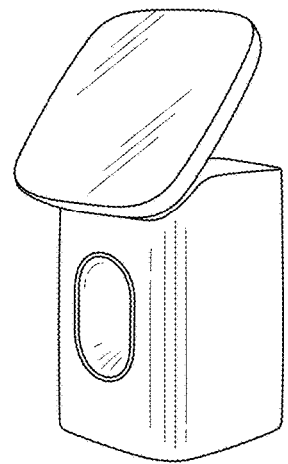
Figure 30H:
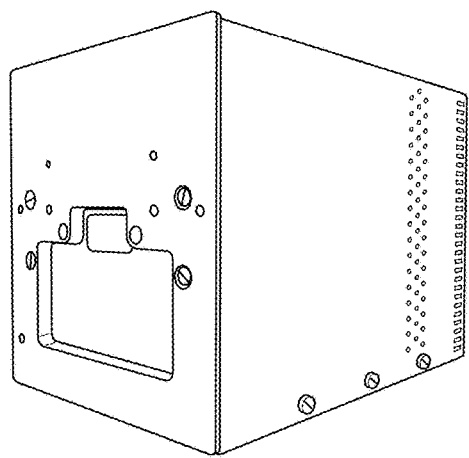
Figure 30J:
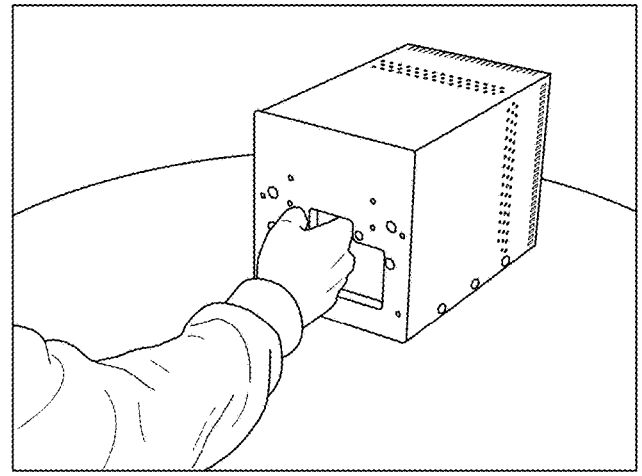
Figure 30K:
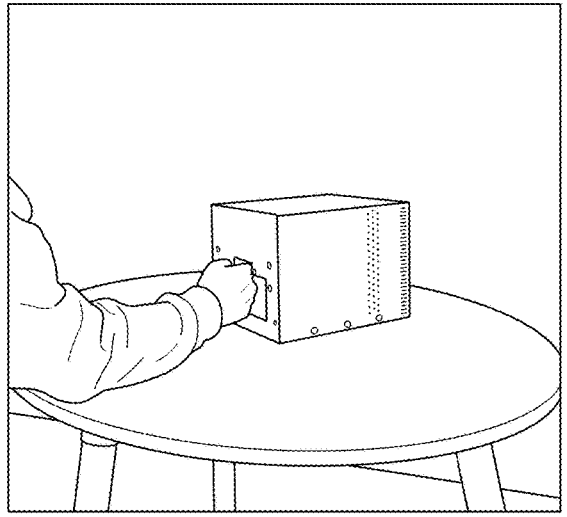
Figure 30M:
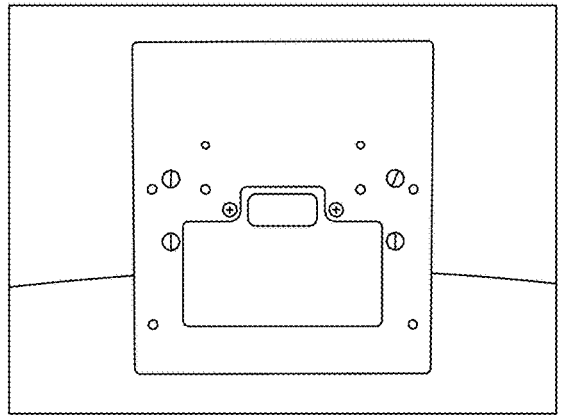
Figure 30L:
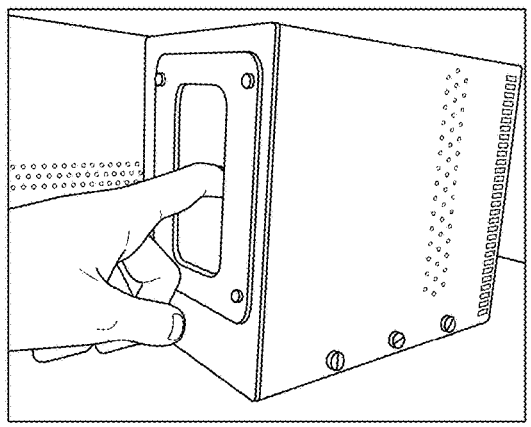
Figure 30N:
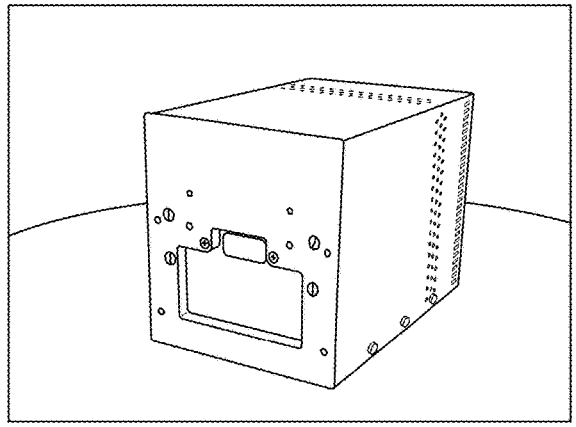

The housing 200 is preferably configured such that the overall NMR system is portable (e.g., a desktop device, etc.), but can alternatively be otherwise configured. Examples are shown in FIGS. 30A-30N. The volume of the housing 200 can be between 20 $cm^3$-1 $m^3$ or any range or value therebetween (e.g., 50 $cm^3$-100,000 $cm^3$, 100 $cm^3$-10,000 $cm^3$, 500 $cm^3$-1000 $cm^3$, etc.), but can alternatively be less than 20 $cm^3$ or greater than 1 $m^3$. The housing footprint can be between 5 $cm^2$-10,000 $cm^2$ or any range or value therebetween (e.g., 10 $cm^2$-1000 $cm^2$, 50 $cm^2$-100 $cm^2$, etc.), but can alternatively be less than 5 $cm^2$ or greater than 10,000 $cm^2$. The housing material can include aluminum, plastic, foam (e.g., to retain components, for potting, for thermal insulation, to reduce electromagnetic interference, etc.), any ferrous material, any non-magnetic material, any light-weight material (e.g., such that the overall weight is less than 50 kg, 10 kg, 5 kg, 2 kg, 1 kg, 0.5 kg, etc.) and/or any other material. The housing 200 can optionally be potted (e.g., with resin or other material).

The housing 200 can optionally include or interface with a shield, which can function to redirect the magnetic field within the housing 200 (and/or reduce the magnetic field outside the housing 200), provide shielding between system components, and/or provide any other magnetic or electromagnetic interference (EMI) shielding. The shield can be mounted to the outside of the housing 200, mounted within the housing 200 (e.g., between system components), and/or otherwise arranged relative to any system component. The shield material can include: mu-metal, steel (e.g., low carbon steel, 1008 steel), iron, nickel, cobalt, a combination of materials, any ferromagnetic material, any material with high (electromagnetic) permeability, and/or any other shielding material. However, the shield can be otherwise configured.

The housing 200 can optionally be located at a target z-location relative to the user, such that the user's hand (when the user's finger is within the sample aperture) is at a target elevation. In illustrative examples, the sample aperture of the housing can be parallel with the user's shoulder, between with the user's shoulder and the user's elbow, parallel to the user's elbow, below the user's elbow, and/or otherwise arranged. In a specific example, the system 10 can include a forearm stand (e.g., optionally mounted to the housing 200), which can function to maintain the user's forearm at a standardized location and/or angle (e.g., parallel to the ground); an example is shown in FIG. 29B. However, the housing 200 can be otherwise configured.

The set of coils 300 functions as an NMR probe, inducing magnetization in the sample and detecting resulting signals from the sample. The set of coils 300 can include one or more of: a transmit coil 320, a receive coil 340, a set of gradient coils 360, an active shim coil 380, an active shield coil, and/or any other coils. All or a portion of the set of coils 300 can be arranged in series, in parallel, and/or otherwise connected. One or more coils in the set of coils 300 can optionally be or include composition arrays. One or more coils in the set of coils 300 (e.g., the set of gradient coils 360, the active shim coil 380, etc.) can optionally be shielded (e.g., using a copper layer, using one or more active shield coils, etc.). One or more passive shields can optionally be positioned in the bore. For example, passive shields can surround all or a portion of one or more coils (e.g., surrounding the transmit coil 320), be positioned between coils (e.g., between the transmit coil 320 and the set of gradient coils 360, etc.), and/or be otherwise positioned. The material of passive shields can be copper and/or any other suitable shielding material.

Figure 5A:
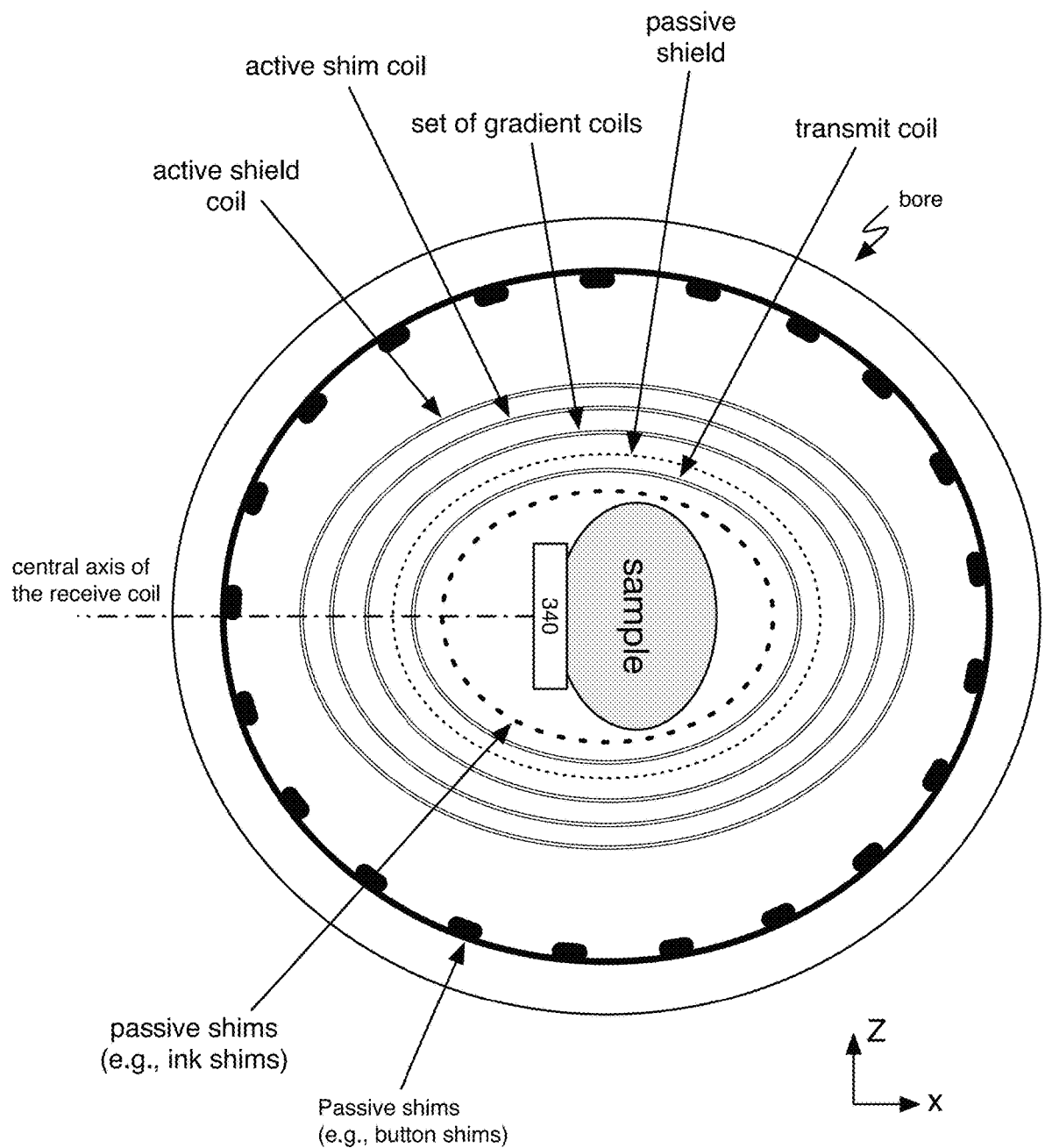
FIG. 5A is an example of a cross-sectional view of the system, including a set of passive shims (e.g., button shims) and a layered arrangement of a set of coils.
Figure 5B:
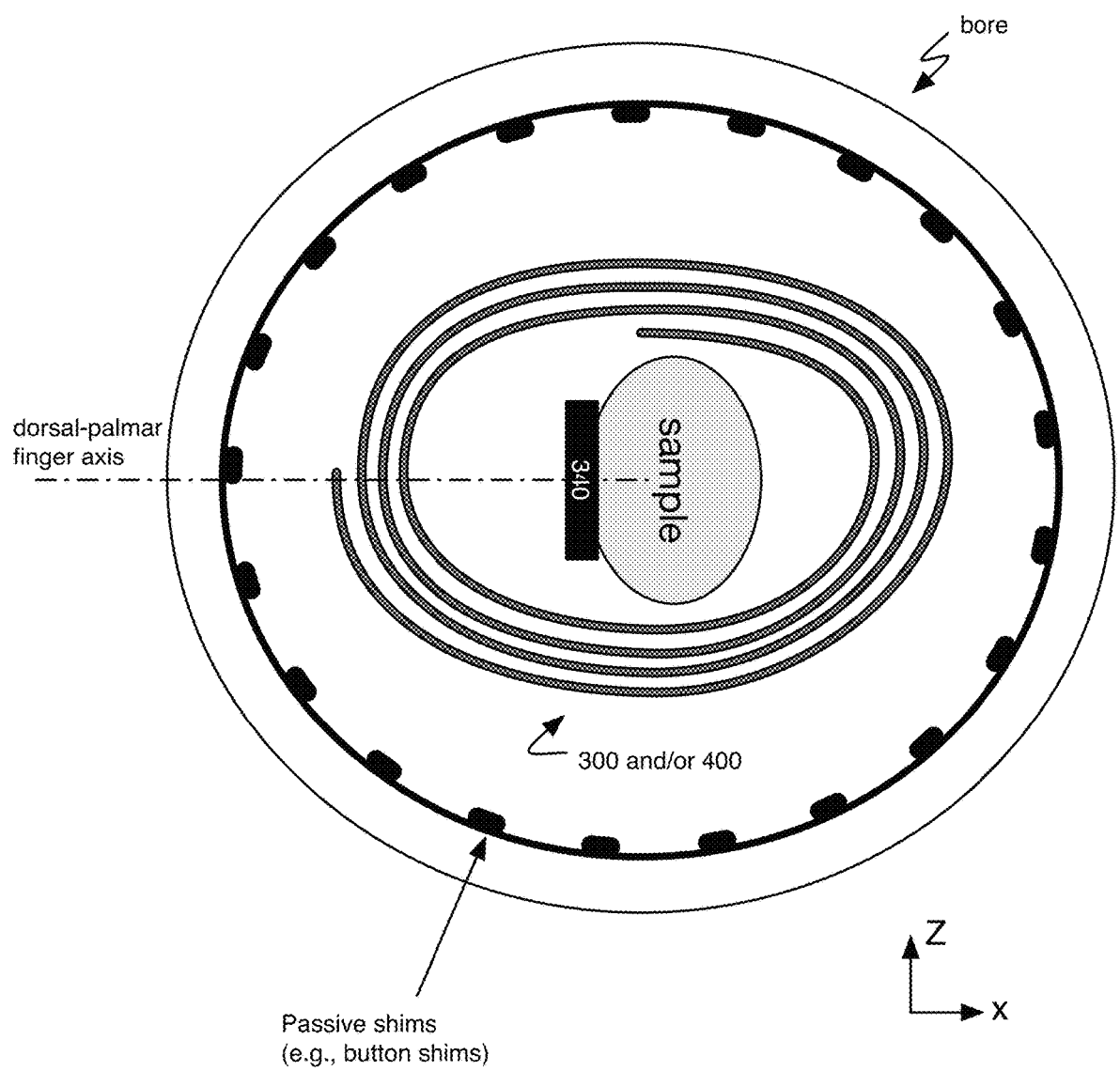
FIG. 5B is an example of a cross-sectional view of the system, including a set of passive shims (e.g., button shims) and a spiraled arrangement of a set of coils.

The set of coils 300 can optionally be mounted to (e.g., printed on) one or more coil supports (e.g., a sheet, a board, etc.). In a specific example, all or a portion of the set of coils 300 (e.g., the transmit coil 320, the active shim coil 380, and the set of gradient coils 360) are printed on a single coil support. Coil supports can optionally be mounted to the housing 200. In a specific example, the coil support can be a flexible board (e.g., flexible printed circuit board). The coil support can optionally include or support other system components (e.g., spacers, the set of passive shims 400, passive shields, etc.). For example, one or more coil supports can be arranged in a set of layers as nested coils within the bore. In a specific example, for each layer in the set of layers, the width of the layer in one dimension (e.g., in the x-direction, where the longitudinal axis of the bore is the y-direction) is greater than the width of the layer in another dimension (e.g., in the z-direction, where the longitudinal axis of the bore is the y-direction). In a first example, multiple coil supports are nested in a set of concentric coil supports. In a second example, a single coil support (e.g., a sheet) can be rolled into a spiral, forming one or more layers (e.g., a loop of the spiral forms a layer of the rolled coil support). In a third example, a combination of the first and second example can be used. The number of layers can be between 1-50 or any range or value therebetween (e.g., at least 2, at least 5, at least 10, etc.), but can alternatively be greater than 50. The layers can correspond to one or more of: the transmit coil 320, the receive coil 340, the set of gradient coils 360 (e.g., a layer can correspond to one gradient coil in the set of gradient coils 360), the active shim coil 380, the active shield coil, passive shields, spacers (e.g., separating the layers), the set of passive shims 400, and/or any other system components. In an illustrative example, the layers of one or more coil supports includes (from the outer layer to the inner layer, wherein the sample and the receive coil 340 are positioned within the innermost layer): a first set of passive shims (e.g., button shims), an active shield coil, an active shim coil 380, a first gradient coil, a second gradient coil, and a third gradient coil, a passive shield, a transmit coil 320, and a second set of passive shims (e.g., ink shims). Examples are shown in FIG. 5A and FIG. 5B.

Figure 9A:
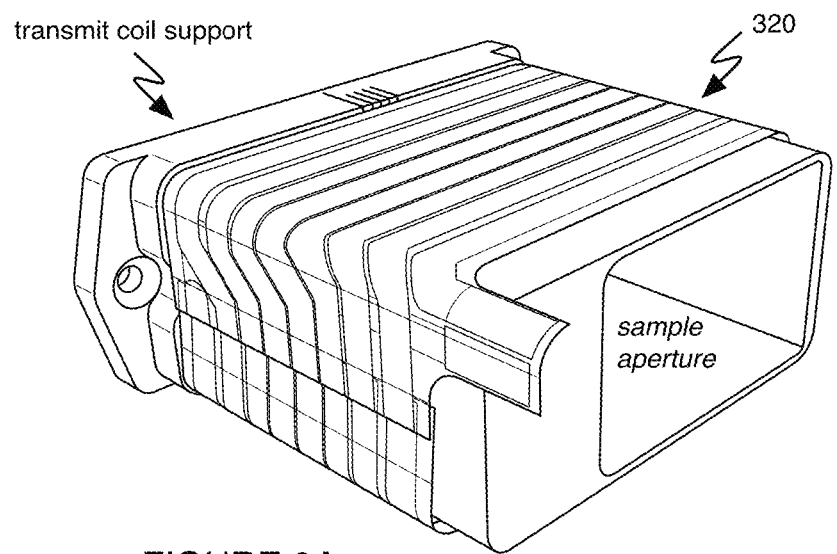
FIG. 9A depicts a specific example of a transmit coil wrapped around a coil support.
Figure 9B:
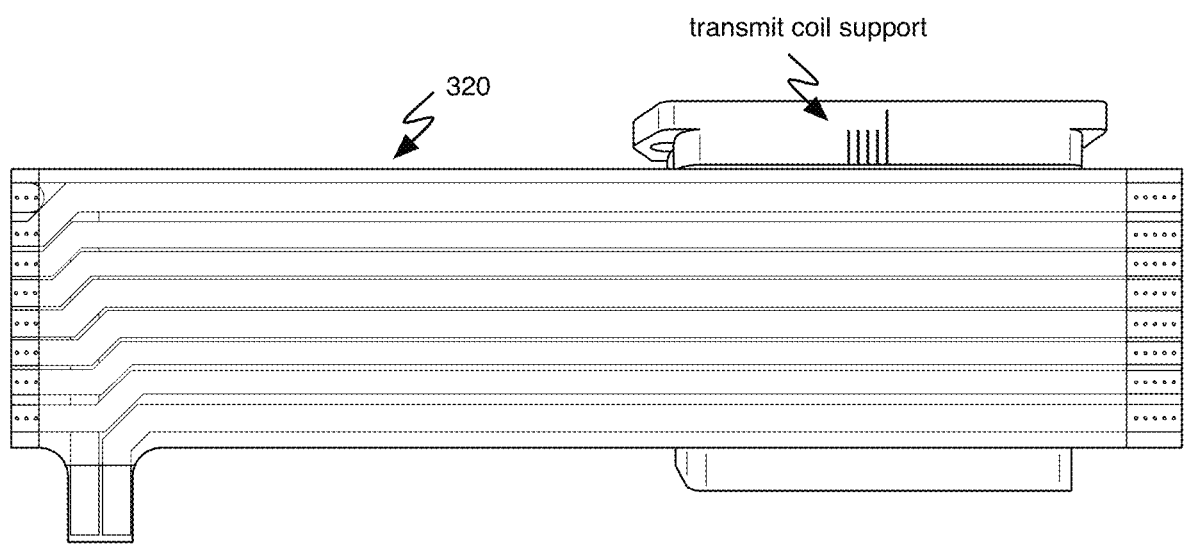
FIG. 9B depicts a specific example of a transmit coil not wrapped around a coil support (e.g., prior to wrapping).

The transmit coil 320 (e.g., transmitter) functions to apply a radiofrequency (RF) sequence within the ROI (e.g., applying the sequence using a substantially homogenous magnetic field imparted by the transmit coil 320). For example, the transmit coil 320 can function to apply a pulse sequence (e.g., S300). The transmit coil 320 preferably includes a solenoid, but can additionally or alternatively include any other coil type. For example, the transmit coil 320 can be oriented such that the axis of the solenoid is parallel to the axis of the bore (e.g., the axis of the solenoid aligns with the proximal-distal axis of the finger). The number of loops in the transmit coil 320 can be between 5-100 or any range or value therebetween, but can alternatively be less than 5 or greater than 100. The length (e.g., perimeter) of each loop of the transmit coil 320 can be between 20 mm-500 mm or any range or value therebetween (e.g., 50 mm-200 mm, 125 mm, etc.), but can alternatively be less than 20 mm or greater than 500 mm. The length of the transmit coil 320 (e.g., length of the solenoid) can be between 10 mm-500 mm (e.g., 25 mm-75 mm, 50 mm, etc.), but can alternatively be less than 20 mm or greater than 500 mm. An example is shown in FIG. 9B. The transmit coil 320 can optionally be coupled to a coil support (e.g., transmit coil support). For example, the transmit coil 320 can be wrapped around a three-dimensional coil support (e.g., wherein the transmit coil support surrounds the sample aperture). An example is shown in FIG. 9A. A cross-section of the coil support (e.g., defining the shape of the transmit coil loops) can be a circular, rectangular (e.g., with beveled edges), and/or any other shape. However, the transmit coil 320 can be otherwise configured.

The receive coil 340 (e.g., receiver) functions to receive signals from excited spins in the sample. For example, the receive coil 340 can function to acquire a signal (e.g., S300). The number of turns (e.g., spiraled loops) in the receive coil 340 can be between 1-50 or any range or value therebetween (e.g., 2, 3, 4, 5, 2-5, less than 10, less than 5, etc.), but can alternatively be greater than 50. The diameter of the receive coil 340 (e.g., of a loop) can be between 2 mm-10 mm or any range or value therebetween (e.g., 3 mm-5 mm), but can alternatively be less than 2 mm or greater than 10 mm. The diameter of the wire of the receive coil 340 is preferably 0.01 mm-2 mm or any range or value therebetween (e.g., 0.1 mm-1 mm), but can alternatively be less than 0.01 mm or greater than 1 mm. The receive coil 340 can optionally include and/or be coupled to one or more capacitors. All or a portion of the capacitors are preferably arranged in parallel relative to one other (e.g., to reduce electron spin resonance), but can alternatively be arranged in series, a combination of series and parallel, and/or otherwise arranged.

Figure 10A:
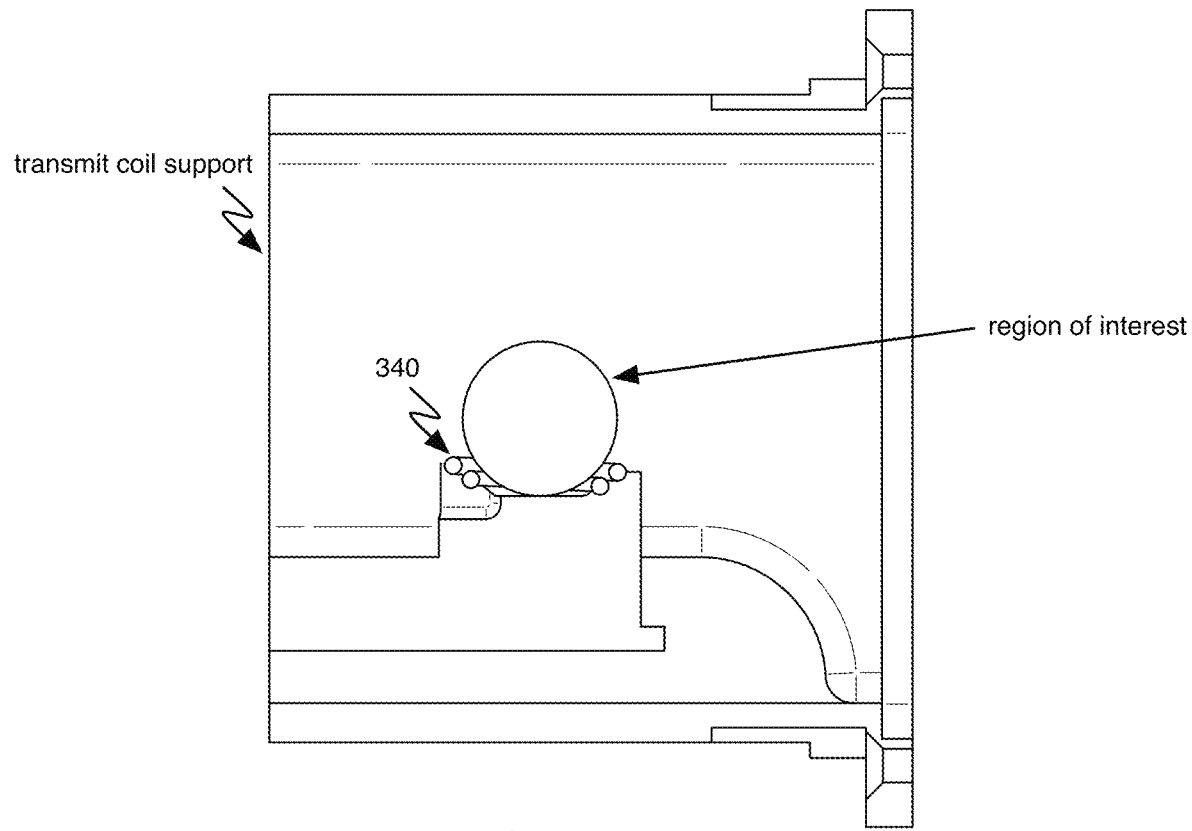
FIGS. 10A and 10B depict examples of a receive coil.
Figure 10B:
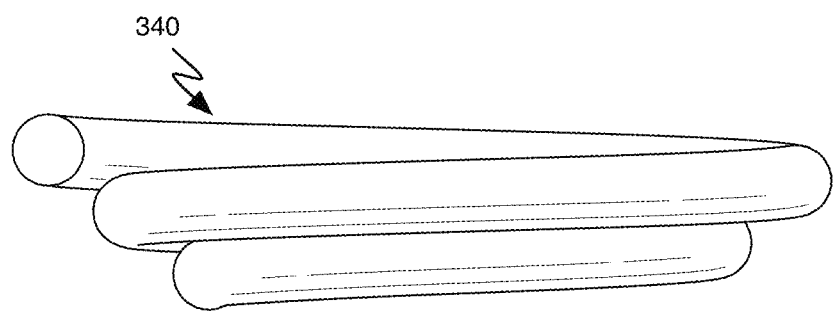

The receive coil 340 is preferably a surface coil (e.g., wherein the receive coil 340 does not include a solenoid), but can alternatively be or include a butterfly coil, a solenoid (e.g., the receive coil 340 is the transmit coil 320, wherein the transmit coil 320 can be a transceiver), and/or any other coil type. The surface coil can optionally be a loop coil (e.g., spiraled). In a first example, the receive coil 340 can be a planar surface coil. In a specific example, the receive coil 340 can form a flat surface in a yz-plane (e.g., the receive coil 340 forms a planar loop coil). In a second example, the receive coil 340 can be a non-planar surface coil; an example is shown in FIG. 10A and FIG. 10B. In a specific example, the receive coil 340 can form an indented surface (e.g., conical, curved, etc.). In a specific example, the receive coil 340 can optionally include turns at different distances to the sample (e.g., x-position of an inner turn further from the sample than the x-position of an outer turn). The thickness of the receive coil 340 (e.g., width in the x-direction between center points of the first and last loops of the receive coil 340; where a 0 mm distance is a planar coil) can be between 0 mm-5 mm or any range or value therebetween, but can alternatively be greater than 5 mm. In a specific example, negative pressure can be used to suction the sample into an indent formed by a non-planar coil.

The axis (central axis) of the receive coil 340 can optionally be oriented to intersect with a target location on the sample (e.g., the target region of the sample, the pulp of the finger, etc.). In a specific example, the axis of the receive coil 340 can be parallel to the x-axis. In an illustrative example, when the finger is positioned within the sample aperture of the housing (e.g., using the sample interface 520) the receive coil 340 (a surface coil) is orthogonal to the finger pulp and flux from the receive coil is parallel with the finger pulp (e.g., the flux is orthogonal to the longitudinal axis of the finger). In a second illustrative example, flux from the receive coil 340 (a solenoid and/or a butterfly coil) is orthogonal to the finger pulp. The receive coil 340 is preferably oriented orthogonal to the transmit coil 320 (e.g., such that the flux lines from the coils are orthogonal), but can alternatively be otherwise arranged. In variants, this can enable isolation between the receive coil 340 and the transmit coil 320.

However, the receive coil 340 can be otherwise configured.

Figure 11A:
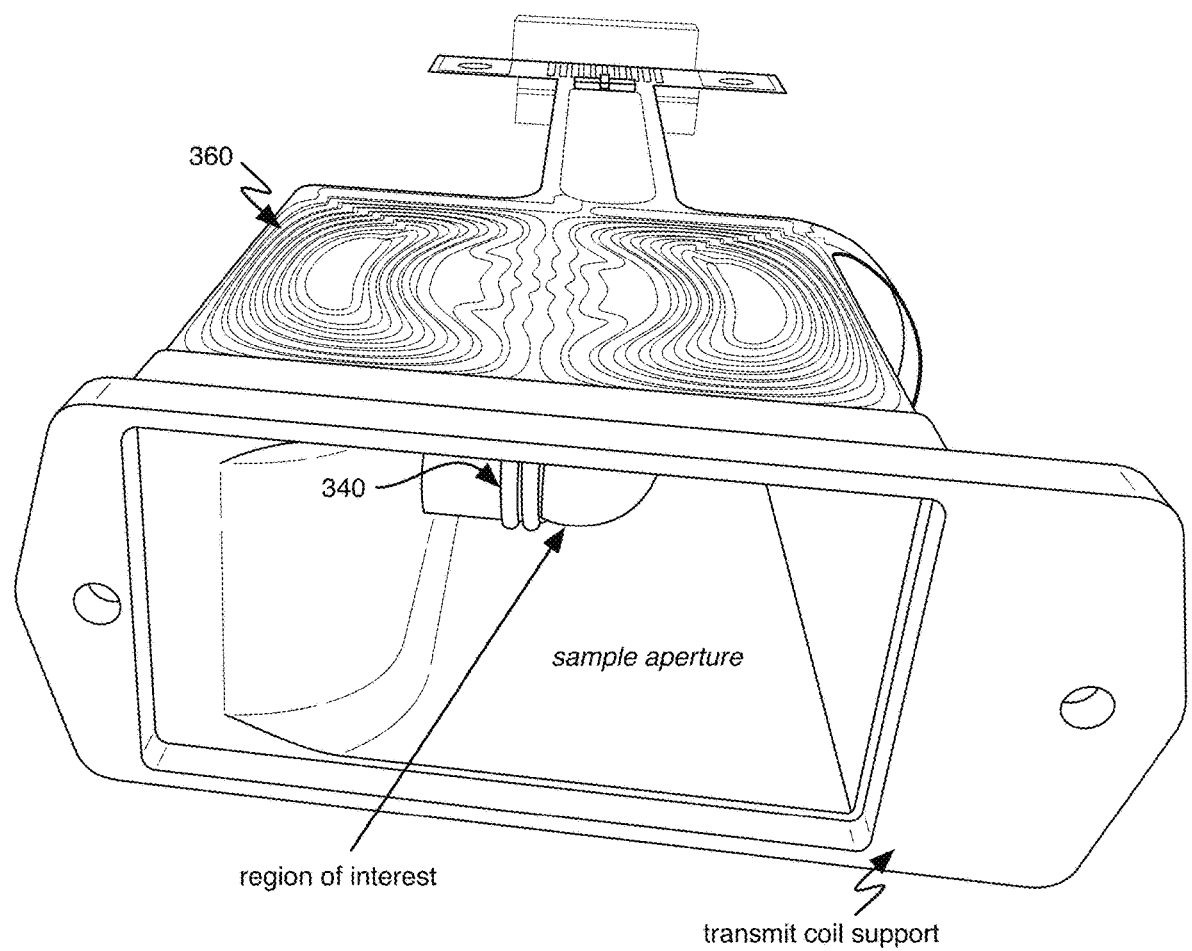
FIGS. 11A and 11B depict examples of the gradient coil mounted to a coil support.
Figure 11B:
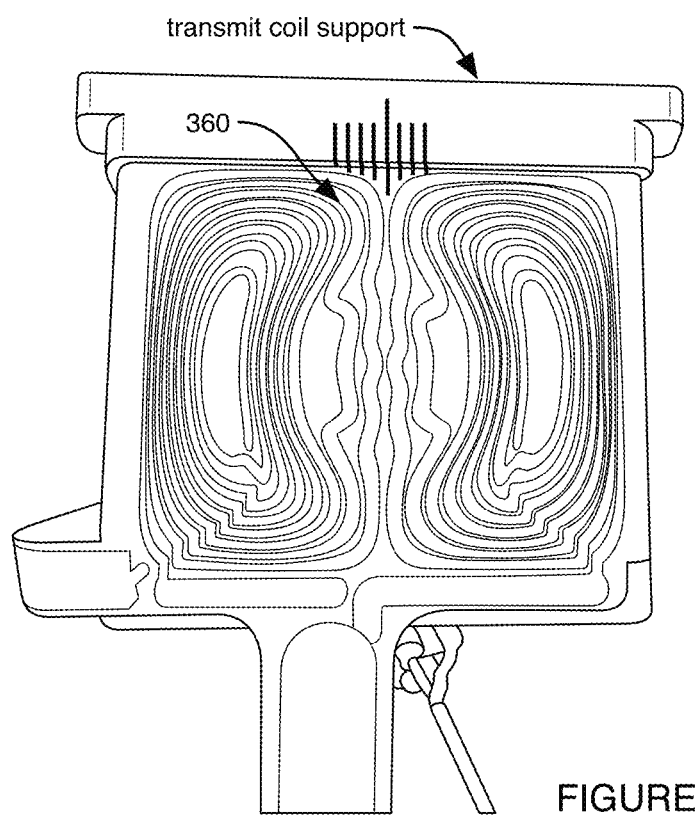
Figure 11C:
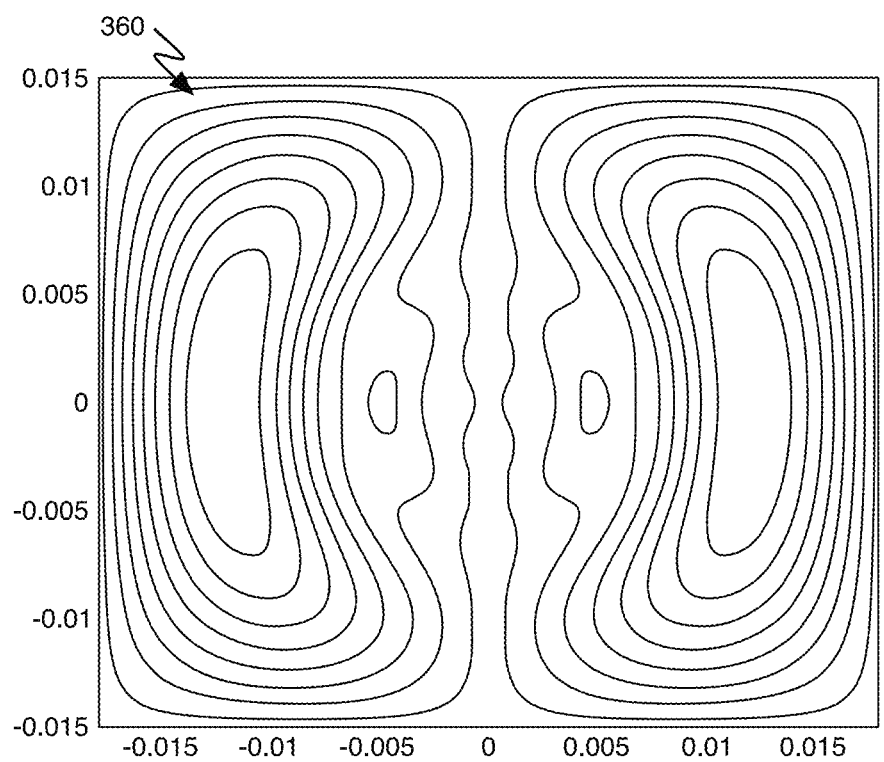
FIG. 11C depicts a plot of an example of the gradient coil.
Figure 23:
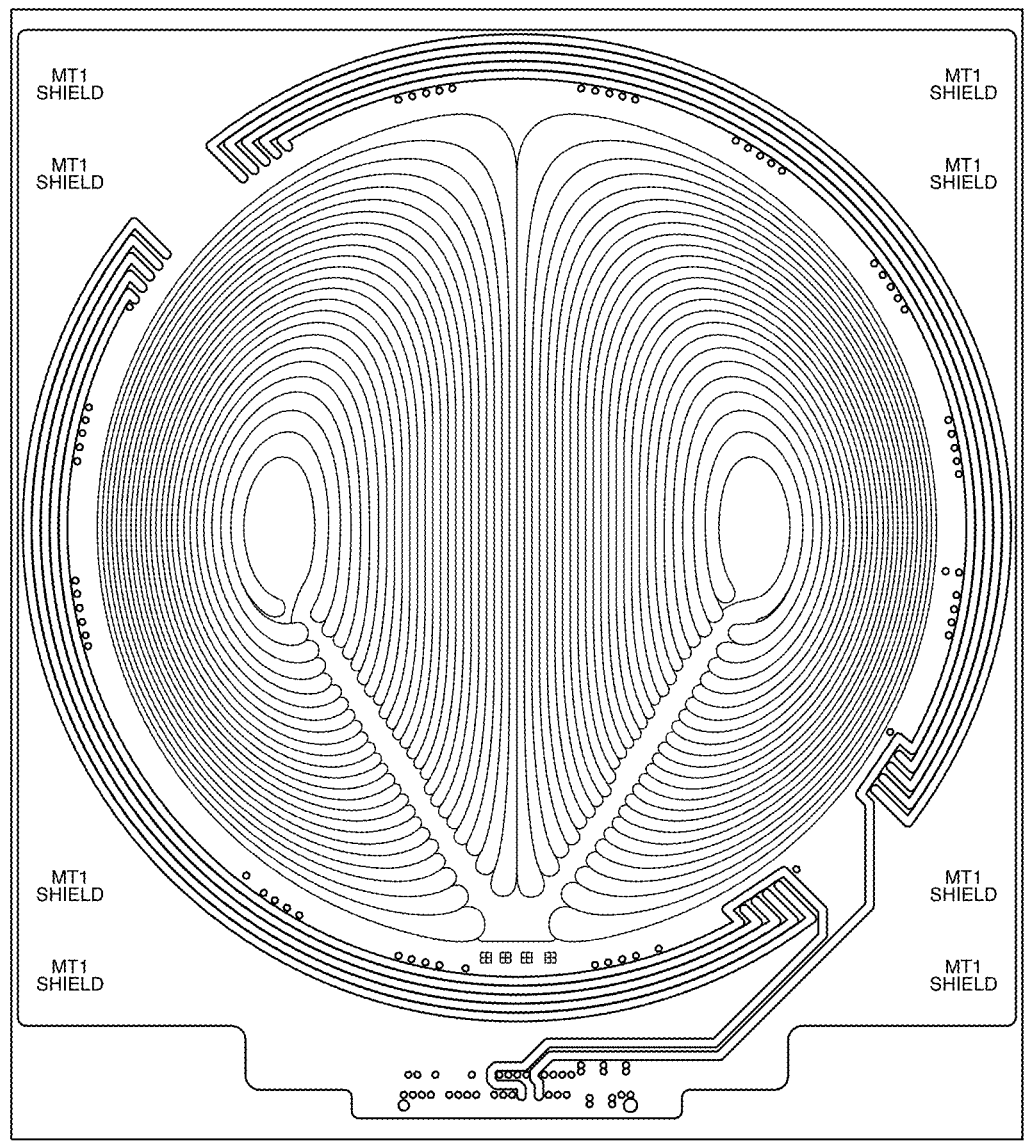
FIG. 23 depicts an example of a coil geometry (e.g., for a gradient coil and/or any other coil).

The set of gradient coils 360 functions to modulate the magnetic field. Examples are shown in FIG. 11C and FIG. 23. For example, the set of gradient coils 360 can function to apply a gradient sequence (e.g., S200). In a first example, the set of gradient coils 360 can enable isolation of a target region (e.g., slice, column, voxel, any other region of interest, etc.) of the ROI (e.g., slice selection). In a second example, the set of gradient coils 360 can impart a corrective gradient (e.g., a crusher gradient to reduce unwanted signals). In a third example, the set of gradient coils 360 can function as active shim coils. The set of gradient coils 360 can be used: concurrently with the transmit coil 320 and/or the receive coil 340; asynchronously with the transmit coil 320 and/or the receive coil 340; and/or at any other time.

The set of gradient coils 360 can impart a magnetic field gradient along one or more axes (e.g., 1 axis, 2 axis, 3 axis, etc.; with one or more gradient coils for each axis). The number of gradient coils in the set of gradient coils (e.g., the number of axes) can be 1, 2, 3, or greater than 3. In a first example, the set of gradient coils 360 can include a single gradient coil linearly modulate the magnetic field along the x-axis, enabling slice selection across layers of the sample (e.g., from the skin of the fingertip, through the pulp). In a second example, the set of gradient coils 360 can include two gradient coils modulating the magnetic field along two directions. In a third example, the set of gradient coils 360 can include three gradient coils modulating the magnetic field along three directions, enabling selection of a voxel of the sample. In a first specific example, the set of gradient coils 360 can modulate the magnetic field in Cartesian coordinates (e.g., the x-axis, the y-axis, and the z-axis, etc.). In a second specific example, the set of gradient coils 360 can modulate the magnetic field in non-Cartesian coordinates (e.g., where a non-planar receive coil 340 is used as a reference).

The set of gradient coils 360 is preferably in series with the transmit coil 320, but can alternatively be in parallel with the transmit coil 320, not coupled to the transmit coil 320, and/or otherwise arranged. Examples are shown in FIG. 11A and FIG. 11B. The set of gradient coils 360 can optionally be shielded (e.g., using a copper layer, using one or more active shield coils, etc.). For example, the set coils can include a set of shield coils configured to shield the magnetic field generated by the set of gradient coils 360. In variants, shielding the gradient coil can function to decouple the set of gradient coils 360 from the transmit coil 320 and/or the receive coil 340.

However, the gradient coil 360 can be otherwise configured.

The active shim coil 380 functions to produce a magnetic field to correct field distortions within the ROI. The active shim coil 380 can include a matrix (e.g., a composition of coils), wherein the current distribution of the matrix can be modified to homogenize (e.g., optimize) the magnetic field. The active shim coil 380 can include one or more coils (e.g., 1, 2, 3, 4, 5, etc.). The active shim coil 380 can optionally be located above (in the positive z-direction) the sample aperture (e.g., above the transmit coil 320 and/or the gradient coil 360) and/or below (in the negative z-direction) the sample aperture. In a specific example, a first active coil is located above the sample aperture and a second active coil is located below the sample aperture. The active shim coil 380 is preferably aligned to the gradient coil 360 (e.g., the flux from the active shim coil 380 is aligned with the flux from the gradient coil 360), but can alternatively be otherwise oriented. However, the active shim coil 380 can be otherwise configured.

However, the set of coils 300 can be otherwise configured.

The system 10 can optionally include a set of passive shims 400 (e.g., set of localized shims) which function to fine-tune the homogenization of the magnetic field within the ROI. The set of passive shims 400 can be located: outside the sample aperture (e.g., defined by the housing 200), within the bore (defined by the set of magnets 100), above or below one or more coils in the set of coils 300, between two magnets in the set of magnets 100, and/or otherwise located. The set of passive shims 400 can be located on one or more substrates (e.g., plates, sleeves, paper, non-magnetic metal sheet, a coil support, etc.), wherein the substrate(s) can optionally be removably mounted to the housing 200 such that the set of passive shims 400 can be adjusted during a shimming stage. One or more passive shims in the set of passive shims 400 can optionally be located on the same substrate as one or more coils in the set of coils 300 (e.g., the substrate can be a coil support). In a specific example, a first subset of passive shims are located on a top plate (e.g., on the upper surface of the top plate) containing a first active shim coil 380 (e.g., on the bottom surface), and a second subset of passive shims are located on a bottom plate (e.g., on the bottom surface of the bottom plate) containing a second active shim coil 380 (e.g., on the top surface). The substrate can optionally form a three-dimensional sleeve. A cross-section of the sleeve (e.g., in the xz plane; in a plane perpendicular to a longitudinal axis of the bore) can optionally be noncircular. In a specific example, the cross-section of the sleeve is oblong (e.g., elongated in a dimension). For example, the cross-section of the sleeve can be elongated in the x-direction (e.g., along the central axis of the surface coil, along the dorsal-palmar axis of the finger, etc.). In a specific example, the cross-section of the sleeve can be elliptical (e.g., the substrate forms an elliptical tube). In another specific example, the cross-section of the sleeve can be spiraled (e.g., the substrate forms an elliptical spiral).

In a first variant, the set of passive shims 400 can include button shims, including permanent magnets or other magnetized materials. In a second variant, the set of passive shims 400 can include ferrous components (e.g., steel). In a third variant, the set of passive shims 400 can include magnetic ink that can be printed or otherwise transferred in a magnetic pattern onto the substrate.

However, the set of passive shims 400 can be otherwise configured.

Figure 13A:
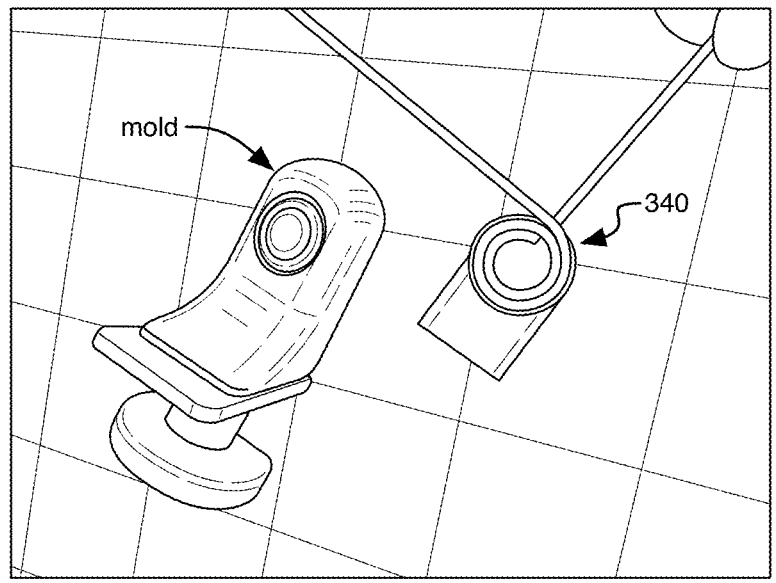
FIG. 13A depicts an example of a sample interface mold.
Figure 13B:
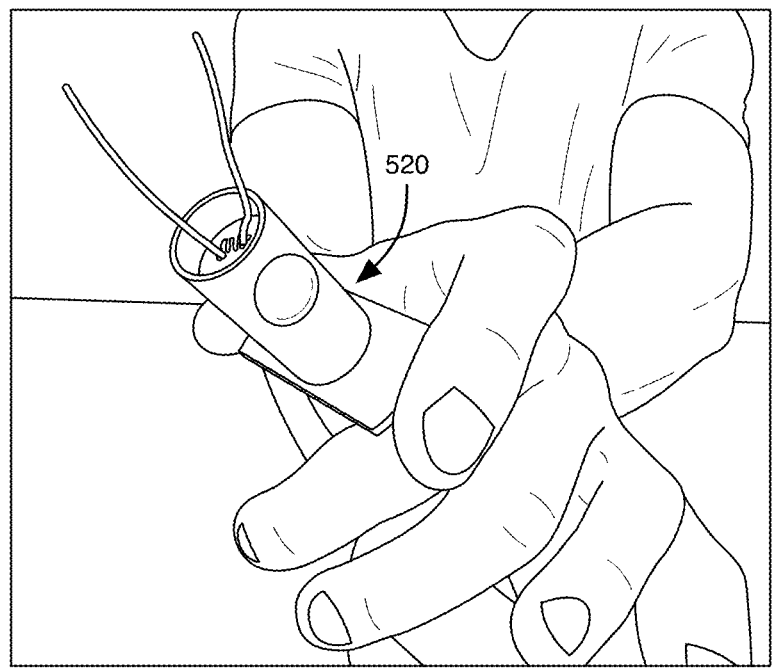
FIG. 13B depicts an example of a sample interface.

The system 10 can optionally include a sample interface 520, which functions to: (repeatably) position the sample in the housing 200 relative to the ROI and/or relative to the receive coil 340, minimize air volume around the sample (e.g., filling volume between the sample and the receive coil 340 with a susceptibility matching material), optimize presence of the analyte of interest in the measurable section of the ROI, reduce signal impact of the user interacting with the device, and/or minimize movement of the sample during the measurement acquisition. The sample interface 520 can be part of the housing 200, mounted to the housing 200, separate from the housing 200, and/or otherwise configured. In a specific example, the sample interface 520 can include the receive coil 340 (e.g., the receive coil 340 is cast inside the sample interface material), interface with the receive coil 340 (e.g., wherein the outer surface of the sample interface 520 includes a negative imprint of the receive coil 340), mount to the housing 200 at a predetermined location relative to the receive coil 340, and/or be otherwise associated with the receive coil 340. An example is shown in FIG. 13B.

The sample interface 520 can optionally include the sample aperture (e.g., the sample interface 520 can include a sleeve forming the sample aperture), wherein the geometry of the sample aperture interfaces with the sample (e.g., conforming to the sample shape, providing a cap at the end of the sample aperture to restrict sample movement in the y direction, compressing the sample, etc.). In variants, the geometry of the sample interface 520 sample aperture can facilitate repeatable positioning of the sample within the sample interface 520 and/or can retain the finger in a desired position. In a first example, the sample interface 520 is a custom fit for each user (e.g., 3D printed for each user). In a second example, the sample interface 520 is one of a set of sizes (e.g., small, medium, large), wherein the optimal size is selected for the user. In a third example, the sample interface 520 is generalized across users.

Figure 12:
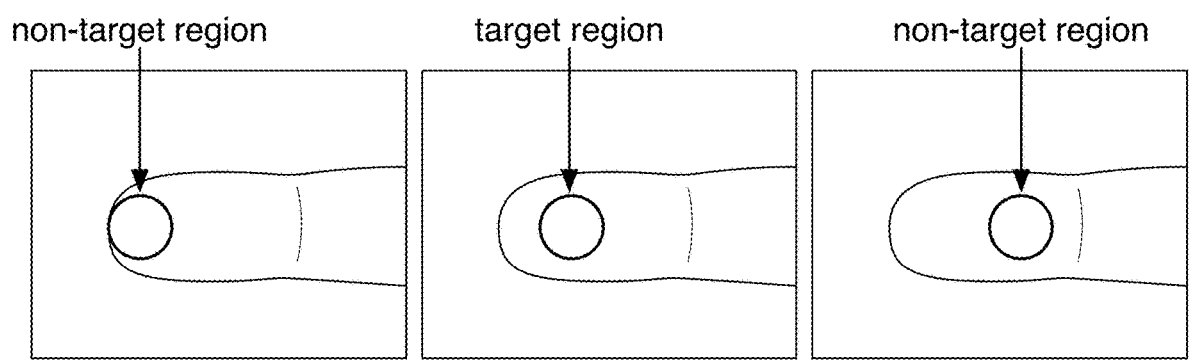
FIG. 12 depicts an example of a target region on a finger.

The sample interface 520 can optionally retain the sample such that the receive coil 340 is located at or near a target location on the sample. In an example, for a finger sample, the target location can be between 1 mm-25 mm from the tip of the finger along the length of the finger (e.g., in the negative y-direction), or any range or value therebetween (e.g., 5 mm-15 mm, etc.), but can alternatively be less than 1 mm or greater than 25 mm. In an illustrative example, the target location can be approximately ⅓ of the way down the length of the finger pad. An example is shown in FIG. 12. In an example, for a finger sample, the gap (e.g., spacing distance) between the receive coil 340 and the surface of the finger can be between 0 mm-50 mm or any range or value therebetween (e.g., less than 10 mm, less than 5 mm, less than 2 mm, less than 1 mm, etc.), but can alternatively be greater than 50 mm. In a specific example, the sample interface 520 can be configured to position the surface of the pulp of the finger within a threshold distance of the surface coil (e.g., within 10 mm, within 7 mm, within 5 mm, within 2 mm, within 1 mm, etc.). In a specific example, the center of the receive coil 340 is at or near the y-location of the sample target location, and optionally a predetermined gap from the sample target location in the x-direction (e.g., where a 0 mm gap results in the sample touching the receive coil). The sample interface 520 can optionally include a cutout for all or a portion of a finger pad (e.g., to enable a decreased gap). The sample interface 520 can optionally include material (e.g., not air) within the gap.

The sample interface material is preferably of a similar susceptibility to a target material (e.g., human tissue, copper, sample material, etc.), but can alternatively have a different susceptibility. For example, the sample interface material susceptibility can match the susceptibility of the target material to within a threshold difference (e.g., (e.g., within 50%, within 40%, within 30%, within 20%, within 10%, within 5%, etc.). The sample interface material is preferably soft (e.g., such that it conforms to the user's finger), but can alternatively be hard. In specific examples, the material can include polyurethane, silicone, and/or any other material. The sample interface 520 can be manufactured using 3D printing, molding, and/or any other manufacturing method. An example of a mold used to manufacture the sample interface 520 is shown in FIG. 13A.

However, the sample interface 520 can be otherwise configured.

The system 10 can optionally include an interference reduction 540, which functions to reduce and/or otherwise correct for thermal and/or electromagnetic noise.

In a first variant, the interference reduction system 540 can include a grounding system which functions to ground the user. The grounding system can be part of the housing 200, mounted to the housing 200 (e.g., outside of the housing 200 or within the housing 200), separate from the housing 200, and/or otherwise configured. The material of the grounding system can include gold, copper, and/or any other electrically conductive material. The grounding system can provide a surface that the skin of the user is in contact with during NMR signal acquisition. In a specific example, the grounding system can include a handle, wherein the user places their hand around the handle (with a finger within the bore). Examples are shown in FIG. 29A, and FIG. 29B. The surface area of the skin of the user that is in contact with the grounding system can optionally be greater than a threshold (e.g., at least 1 cm$^2$, at least 5 cm$^2$, at least 10 cm$^2$, at least 50 cm$^2$, at least 100 cm$^2$, etc.).

In a second variant, the interference reduction system 540 can include a processing system module that performs active NMR measurements and post-processes the measurements to correct for noise.

However, the interference reduction system 540 can be otherwise configured.

The system 10 can optionally include a thermal regulation system 560, which functions to maintain the sample and/or one or more system components at a target temperature, to reduce temperature gradients across system components, and/or otherwise regulate temperature. This can increase measurement accuracy (e.g., by reducing field fluctuations), increase the volume of blood in the sample, improve calibration, and/or otherwise improve system function. In a first example, the thermal regulation system 560 can include a heater and/or a cooler. In a specific example, the thermal regulation system 560 can include a peltier junction. The thermal regulation system 560 can be located on the outside of the housing 200, integrated into the housing 200 (e.g., at or near the sample aperture), and/or otherwise arranged relative to any system component. The thermal regulation system 560 preferably maintains the sample and/or one or more system components above room temperature (e.g., 25° C., 30° C., 35° C., 37° C., 40° C., 45° C., body temperature, any range or value therebetween etc.), but can alternatively maintain the sample and/or one or more system components below room temperature. The thermal regulation system 560 can optionally include a sensor (e.g., temperature sensor, NMR measurements, etc.), wherein sensor measurements can be used to: flag an error, provide feedback to the thermal regulation system 560, adjust signal processing, and/or otherwise used. In a second example, the thermal regulation system 560 can include insulation. The insulation material can include: foam, potting material, plastics (e.g., PVC), and/or any other thermally insulating material. The insulation is preferably non-magnetic, but can alternatively be magnetic. However, the thermal regulation system 560 can be otherwise configured.

The processing system 600 functions to: send and/or receive signals from the set of coils; process signals (e.g., to determine analyte levels, to generate images of the sample; etc.); control the thermal regulation system 560; store measured analyte levels; and/or perform other functionalities. For example, the processing system 600 can send sequences to the transmit coil 320, gradient coil 360, and/or active shim coil 380; and can receive signals from the receive coil 340. In a specific example, the processing system 600 can function to apply a pulse sequence (e.g., S100) via the transmit coil 320; apply a gradient sequence (e.g., S200) via the gradient coil 360; acquire a signal (e.g., S300) via the receive coil 340; process the signal (e.g., S400); and/or perform any other methods. Additionally or alternatively, the processing system 600 can function to simulate: a pulse sequence, a gradient sequence, a signal, and/or simulate any other input or output. Simulating sequences and/or signals can function to calibrate the system 10 and/or method, determine sequence parameters, predict signal parameters, and/or perform other functions.

The processing system 600 can perform one or more scans (e.g., calibration scans to calibrate one or more parameters, measurement scans to determine analyte levels in the sample, etc.). Scans can optionally be simulated scans (e.g., with simulated sequences and/or simulated signals). Each scan can include transmitting sequences to one or more coils (e.g., transmit coil 320, gradient coil 360, active shim coil 380, etc.) and acquiring signals from the receive coil 340.

In an example, the processing system 600 can be configured to: using the transmit coil 320, transmit a sequence of electromagnetic pulses (e.g., including an excitation pulse configured to excite the finger and a set of refocusing pulses); using the set of gradient coils 360, transmit a sequence of gradient pulses (e.g., gradient pulses concurrent with a subset of the set of refocusing pulses) configured to select a target region of the finger; using the receive coil 340, sample a receive signal; and determine a blood analyte concentration in the finger (e.g., in the target region of the finger) based on the receive signal. In a specific example, the sequence of electromagnetic pulses can include a first set of refocusing pulses (e.g., a train of non-selective refocusing pulses) and second set of refocusing pulses (e.g., a train of selective refocusing pulses), wherein each gradient pulse in the sequence of gradient pulses is transmitted approximately concurrently with a refocusing pulse in the second set of refocusing pulses.

Figure 16A:
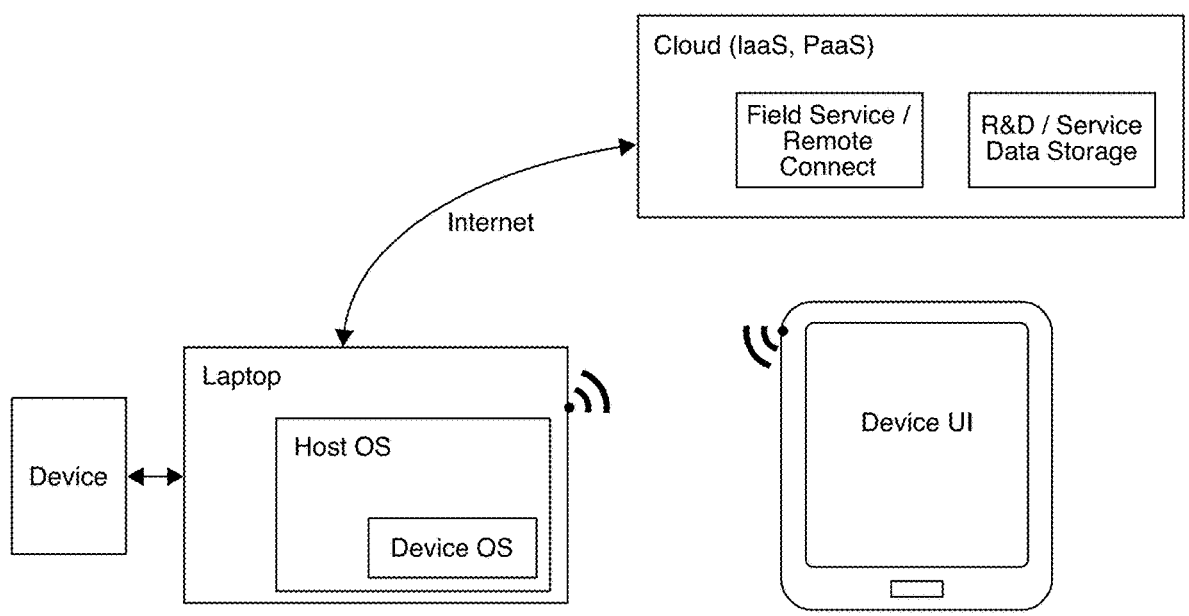
FIGS. 16A-16C are schematic representations of examples of the system.
Figure 16B:
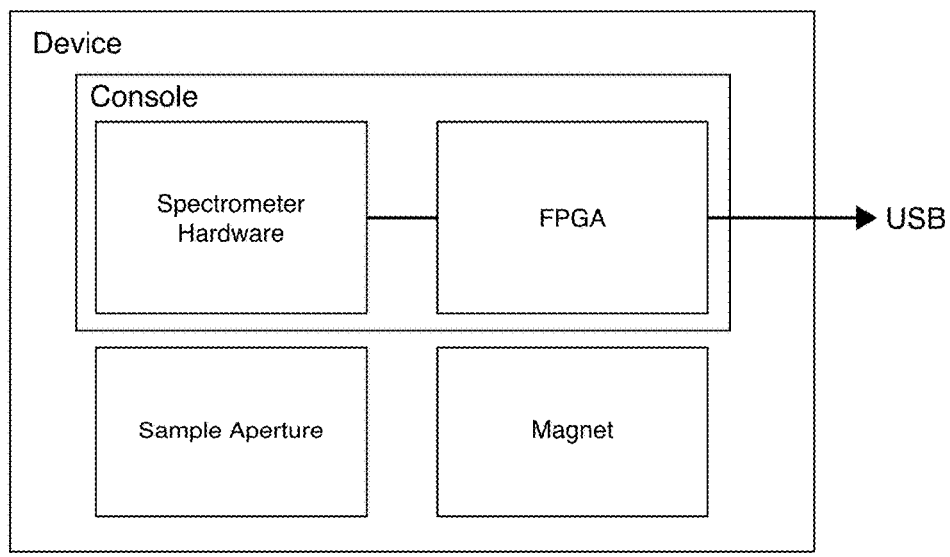
Figure 16C:
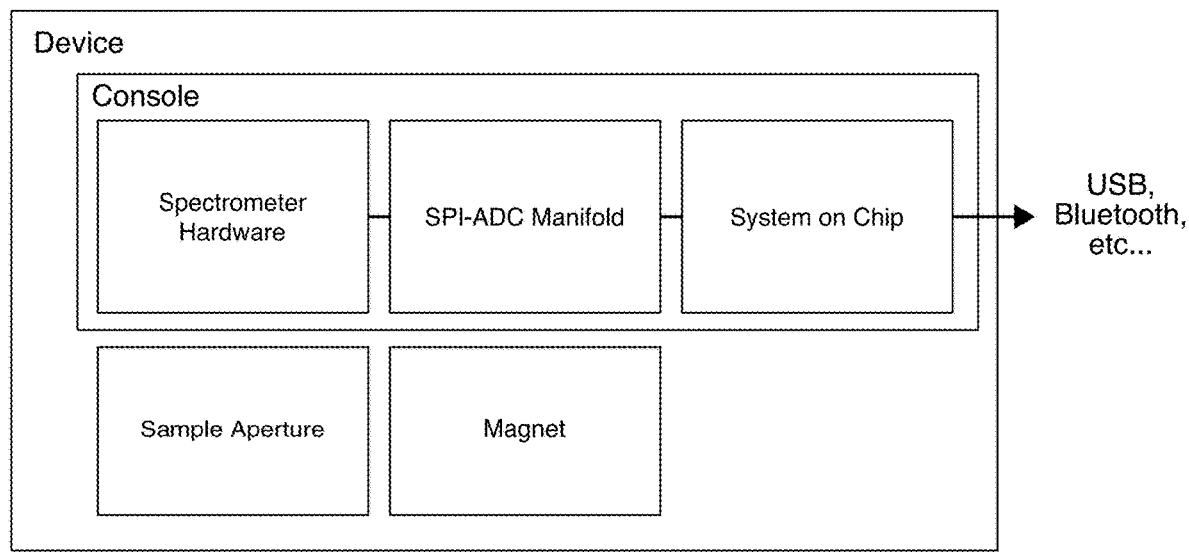
Figure 17A:
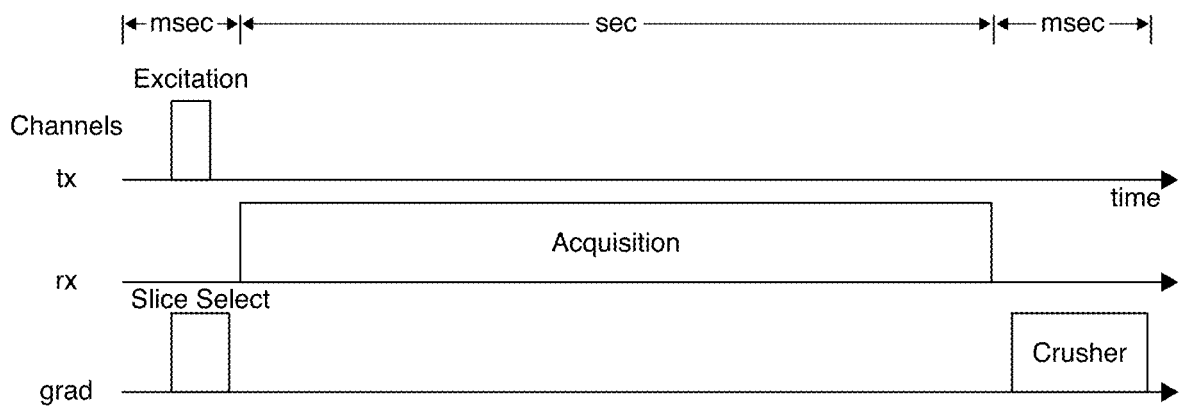
FIG. 17A depicts an example of a free-induction decay sequence.
Figure 17B:
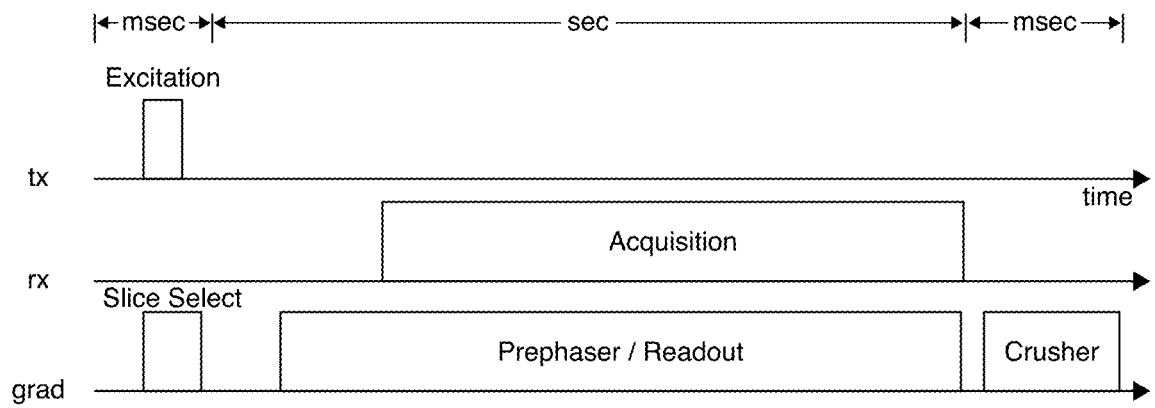
FIG. 17B depicts an example of a gradient echo sequence.
Figure 17C:
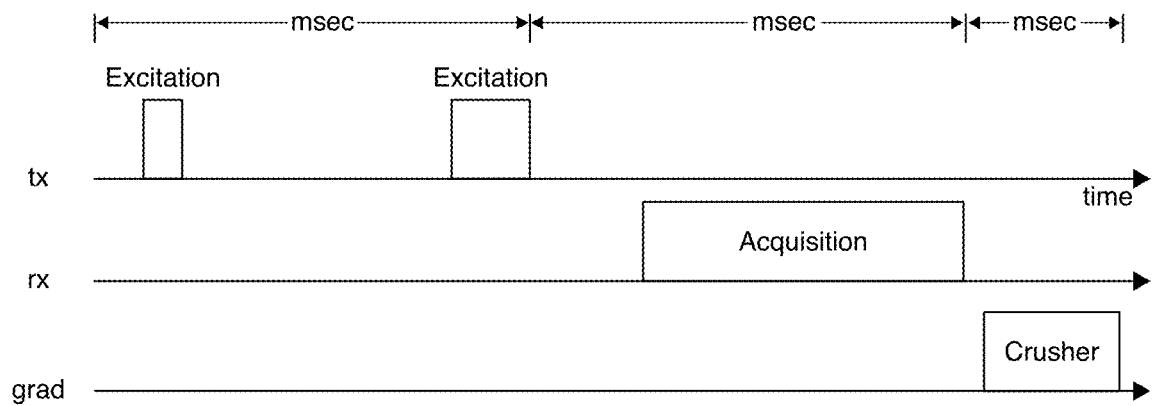
FIG. 17C depicts an example of a spin echo sequence.
Figure 17D:
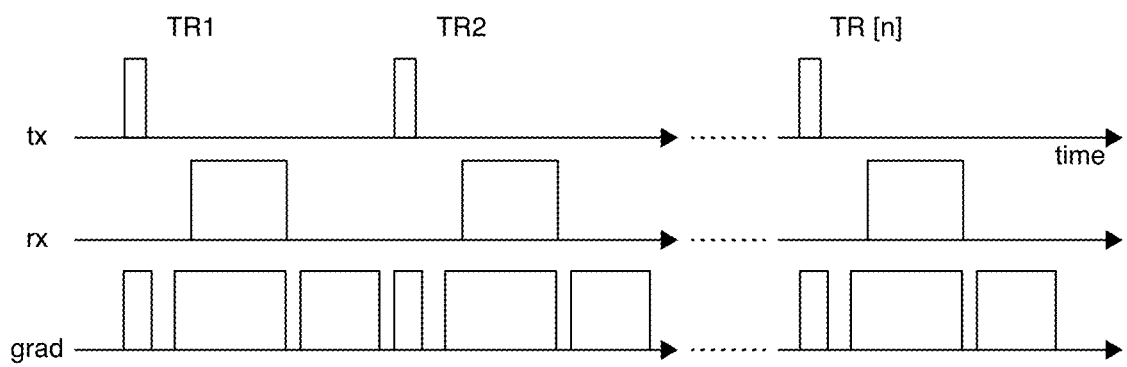
FIG. 17D depicts an example of a gradient echo train sequence.
Figure 17E:
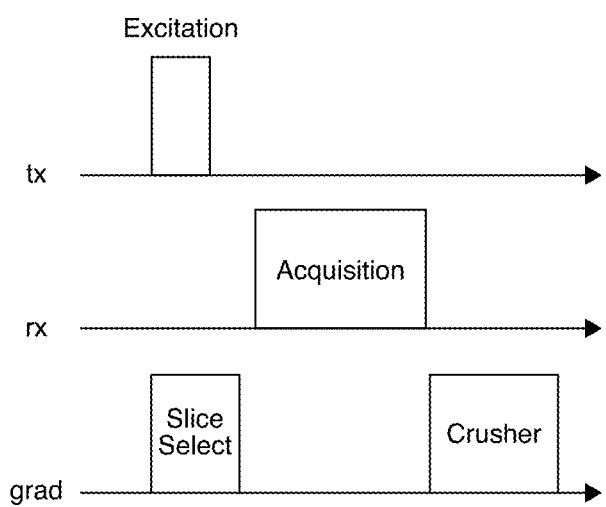
FIG. 17E depicts an example of a center frequency calibration sequence.
Figure 18:
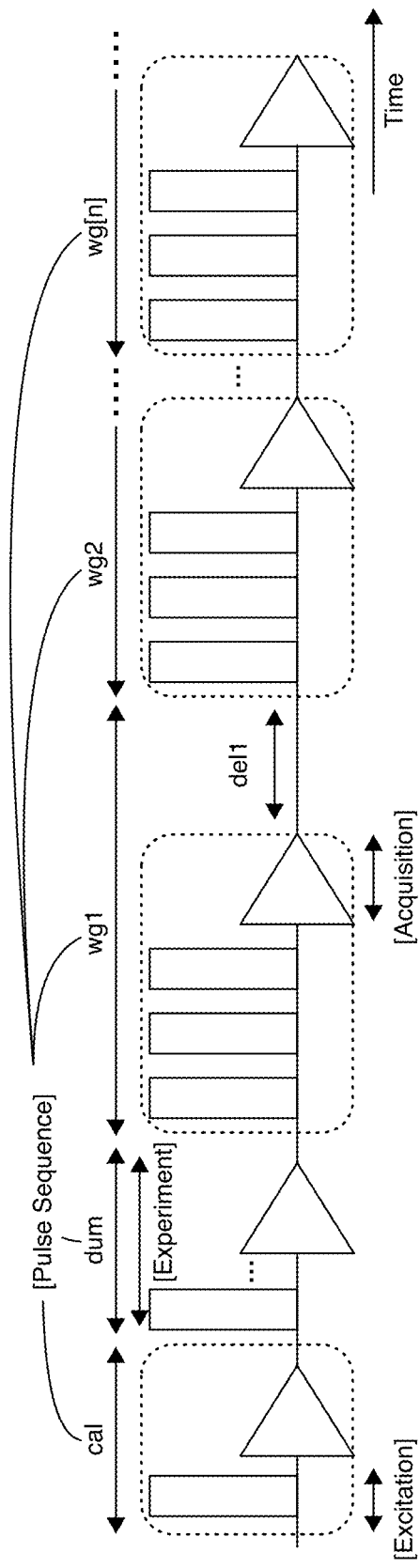
FIG. 18 depicts an example of a measurement scan sequence.

The processing system 600 can include one or more: CPUs, GPUs, custom FPGA/ASICS, microprocessors, servers, cloud computing, and/or any other suitable components. The processing system 600 can be local (e.g., mounted within the housing 200, connected to the set of coils 300 and/or thermal regulation system 560, etc.), remote, distributed, and/or otherwise arranged relative to any other system or module. The processing system 600 can optionally communicate with a user device and/or a user interface (e.g., to display analyte levels, instructions to the user, etc.). Examples are shown in FIG. 16A, FIG. 16B, and FIG. 16C.

However, the processing system 600 can be otherwise configured.

5. Method

As shown in FIG. 2, the method can include: applying a pulse sequence S300, acquiring a signal S500, and processing the signal S600. The method can optionally include shimming the system S100, calibrating the system S200, applying a gradient sequence S400, and/or any other suitable steps. However, the method can additionally or alternatively include any other suitable steps.

All or portions of the method can be performed during system assembly (e.g., manufacturing) of the system 10, during calibration of the system 10 (e.g., to determine active shimming parameters, to determine a target region), before an experiment, during an experiment, after an experiment, between experiments, and/or at any other time. All or portions of the method can be performed in real time (e.g., responsive to a request), iteratively, concurrently, asynchronously, periodically, and/or at any other suitable time. All or portions of the method can be performed automatically, manually, semi-automatically, and/or otherwise performed.

All or portions of the method can be performed by one or more components of the system 10, using a computing system, using a database (e.g., a system database, a third-party database, etc.), user interface, by a user, and/or by any other suitable system.

The method can optionally include shimming the system S100, which functions to increase homogeneity of the magnetic field within the region of interest (ROI). After shimming, homogeneity difference of the magnetic field within the ROI can be below a threshold value (e.g., 500 ppm, 100 ppm, 50 ppm, 10 ppm, 1 ppm, 0.5 ppm, etc.). The system 10 can optionally be shimmed based on one or more measurements. In a first example, the system 10 can be shimmed based on magnetic field measurements in the ROI acquired using a probe (e.g., a capillary probe; positioned within the bore using an actuator in one or more dimensions). In a second example, the system 10 can be shimmed based on NMR measurements of a sample and/or sample proxy (e.g., another user's finger, a phantom, etc.) within the ROI. In a specific example, measurements can be acquired during a shimming stage, and shimming parameters (e.g., magnet shimming parameters, passive shimming parameters, active shimming parameters, etc.) can be determined based on the measurements. The shimming parameters can be determined and/or adjusted automatically, manually, and/or otherwise determined.

In a first variant, the system 10 can be shimmed by adjusting the position of magnets in the set of magnets. For example, magnets can be shifted radially inwards (e.g., towards the center of the bore, towards the center of the ROI, etc.), shifted radially outwards (e.g., away from the center of the bore, away from the center of the ROI, etc.), shifted to increase a gap with an adjacent magnet, shifted to decrease a gap with an adjacent magnet, and/or otherwise moved. Magnet shimming parameters can include magnet position, magnet position adjustment, and/or any other suitable parameters. The magnets in the set of magnets 100 can optionally be bonded (e.g., using thermal bonding) after positioning.

In a second variant, the system 10 can be shimmed using the set of passive shims 400 (e.g., button shims, ink shims, etc.). Passive shimming parameters can include location, quantity, geometry, magnetic strength, material properties, and/or any other parameter of each passive shim in the set of passive shims 400. In a first embodiment, unmagnetized button shimming elements can be individually magnetized and inserted into a corresponding location in a substrate (e.g., a button shimming sleeve), wherein the substrate is positioned within the bore. In a specific example, the substrate can be positioned to surround all or a portion of the set of coils 300. In an example, the location and magnetization of each button shimming element on the substrate can be determined based on one or more magnetic field measurements of the ROI. The substrate can optionally contain pockets configured to retain the button shimming elements (e.g., using crush ribs, using adhesive, etc.). In a specific example, the set of button shims can be retained within pockets of a sleeve, wherein the sleeve is positioned within the bore. The number of button shimming elements can be between 10-100,000 or any range or value therebetween (e.g., at least 100, at least 500, at least 1000, at least 5000, etc.), but can alternatively be less than 10 or greater than 100,000. The material of the button shimming elements can optionally be neodymium (e.g., grain-oriented neodymium). The material of the substrate can optionally be polycarbonate and/or any other plastic material. In a second embodiment, magnetic ink can be deposited (e.g., printed) on an substrate (e.g., an ink shimming sleeve), wherein the substrate is positioned within the bore. For example, the quantity (e.g., number of droplets) of magnetic ink deposited at each of a set of locations on the substrate can be determined based on one or more magnetic field measurements of the ROI. The magnetic ink can optionally be cured (e.g., UV cured). In a specific example, the substrate can be positioned to surround the sample and the receive coil 340. In a specific example, the ink shimming sleeve can be positioned to be surrounded by a transmit coil 320, a gradient coil 360, an active shim coil 380, a shield coil, and/or any other coils in the set of coils 300. In a third embodiment, the system 10 can be shimmed first using a set of button shims (e.g., for coarse shimming) and then using ink shims (e.g., for fine-tuned shimming).

In a third variant, the system 10 can be shimmed using the active shim coil 380. Active shimming parameters can include current, voltage, current pattern, voltage pattern, coil geometry, and/or any other parameters. In an example, in a shimming stage, the processing system 600 can determine active shimming parameters based on an initial calibration scan. In a specific example, the initial calibration scan can include a transmitted pulse sequence that includes all or a portion of a transmitted pulse sequence in the measurement scan (e.g., the same pulse sequence(s) are used). In a first example, active shimming can include shimming on the water signal. In a specific example, shimming can be performed at long echo times (e.g., at least: 50 ms, 75 ms, 100 ms, 200 ms, 300 ms, any range or value therebetween, etc.). Shimming at long echo times can optionally facilitate achieving narrow shims (e.g., narrow NMR linewidths). In an illustrative example, at long echo times, signals from fast-relaxing components in the sample are suppressed so the slowly relaxing water compartment remains (with an analyte signal). Shimming pulses can include tip angles between 1°-180° or any range or value therebetween (e.g., 90°, 180°, less than 90°, less than 45°, etc.), but can alternatively be less than 1° or greater than 180°. In a second example, 3D gradient shimming (e.g., using GRE imaging) can be used.

In a fourth variant, a combination of the previous variants can be used (e.g., in succession, concurrently, etc.). In a specific example, a first shimming stage includes positioning the set of magnets 100, a second shimming stage includes shimming using button shims, a third shimming stage includes shimming using ink shims, and a fourth shimming stage includes shimming using the active shim coil 380. However, shimming stages can be performed at any other time.

However, the system 10 can be otherwise shimmed.

The method can optionally include calibrating the system S200, which functions to calibrate parameters of system components, calibrate signal processing, calibrate pulse sequences, and/or otherwise calibrate systems and/or methods. Calibration the system can be performed during system assembly (e.g., manufacturing), before an experiment, during an experiment (e.g., the experiment includes a calibration, the experiment is a calibration, etc.), after an experiment, and/or at any other time. A calibration can be performed for one or more times for each user, one or more times for each experiment, and/or any other number of times. Calibration can be performed without a sample present, with a sample present, with a sample proxy (e.g., a phantom, another user's finger, etc.) present, and/or can be otherwise performed. In a specific example, calibrating the system can include preforming a calibration scan (e.g., applying a calibration sequence using methods in S300), wherein a calibration signal is acquired (e.g., using methods in S500) and used to calibrate the system.

In a first embodiment, a pilot scan can be used to perform one or more criteria checks (e.g., verifying noise level is below a threshold). The user can optionally be instructed to adjust finger position, adjust temperature, and/or any other adjustments based on the pilot scan.

In a second embodiment, center-frequency calibration can be used to account for the sample temperature. The center-frequency (CF) can be determined based on a calibration signal, wherein the calibration signal can be acquired using a calibration scan of the sample and/or a water signal portion of a measurement scan (e.g., in a first portion of the measurement scan). In a specific example, the center-frequency can be determined using a fit function applied to the calibration signal. In examples, center-frequency calibration can be performed as disclosed in U.S. application Ser. No. 18/503,909 filed 7 Nov. 2023, which is incorporated in its entirety by this reference.

In a third embodiment, calibration can include determining T1 measurements and/or T2 measurements. For example, sequence parameters used in S300 can optionally be dependent on T1 measurements. In a first example, for a fast T1 estimation, the Faster Longitudinal relaxation Investigated by Progressive Saturation (FLIPS) method can be used. In a second example, a (traditional) T1 curve can be measured, which can optionally be used to determine an inversion time to use for the sample.

In a fourth embodiment, performing a calibration can include determining (e.g., selecting) a target region. The target region can be determined by iterating through each region (e.g., each slice) of a set of regions in the ROI, by performing an imaging experiment (e.g., using the system 10 as an MRI or other imagining system), and/or otherwise determined. The target region and/or parameters thereof (e.g., location, dimensions, etc.) can optionally be variable between users, wherein the target region can be determined using a calibration signal for each user. The target region can be determined (e.g., selected) using a set of heuristics, criteria, a model, and/or any other selection methods.

Figure 15A:
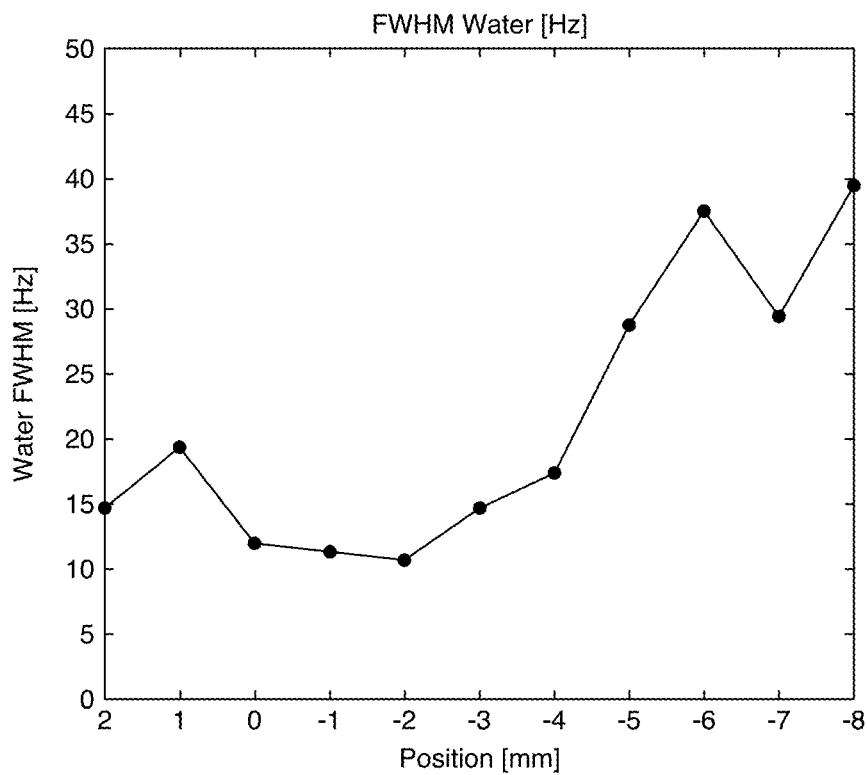
FIG. 15A depicts an example of full width at half maximum (FWHM) of a water signal across slices.
Figure 15B:
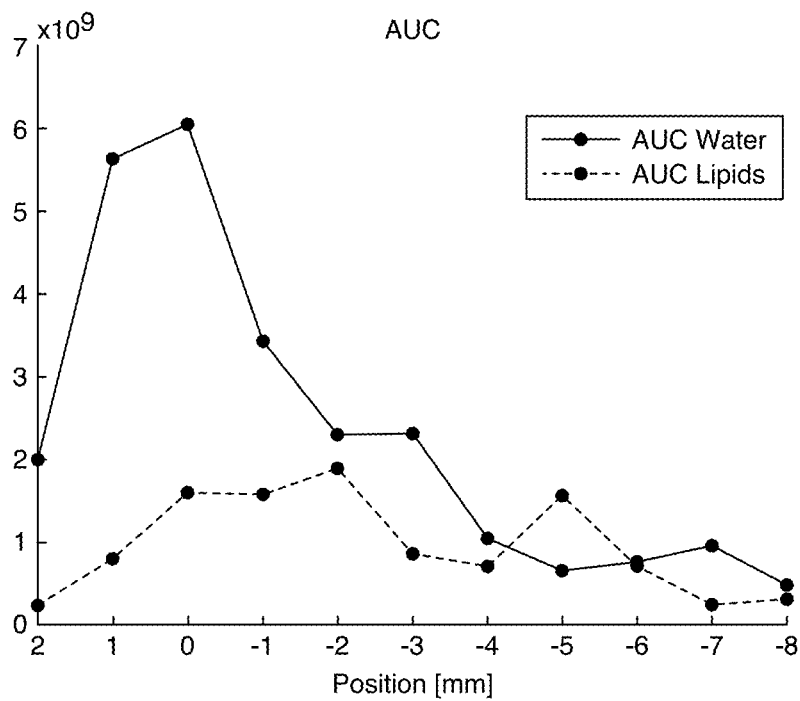
FIG. 15B depicts an example of area under the curve for a water signal and a lipid signal across slices.

The target region and/or parameters thereof can optionally be determined based on a measurement. The measurement can include or be based on one or more calibration signals acquired in one or more calibration scans. In a specific example, the location of the target region is determined based on a calibration signal acquired in a calibration scan. In a specific example, the target region can be determined based on one or more parameters of a calibration signal and/or a portion thereof (e.g., a water component, a lipid component, etc.). Examples of calibration signal parameters include: maximum signal intensity, signal shape (e.g., area under the curve, full width at half maximum, etc.), lipid components, water components, lipid content, water content, lipid compartments, water compartments, parameters thereof (e.g., location, composition, etc.), relative parameters (e.g., height) between a lipid component and a water component (e.g., a ratio between a lipid component and a water component), percentage of the signal from blood, and/or any other signal parameters. In a first embodiment, the measurement includes one or more images of the sample. The image can be a 1-dimensional image, a two-dimensional image, a three-dimensional image, and/or have any other dimensions. For example, the system 10 can be used as an MRI system, wherein one or more images are acquired of the sample. The image(s) can optionally be images of water content in the sample, lipid content in the sample, water compartments, lipid compartments, and/or any other sample components. In a second embodiment, the measurement includes one or more NMR measurements. For example, the measurement can include a sequence of slices of the sample. Examples of parameters across slices are shown in FIG. 15A and FIG. 15B. In another example, the measurement is acquired using T2 and/or diffusion. In a specific example, the measurement can include the content of water compartments and/or lipid compartments.

Figure 14:
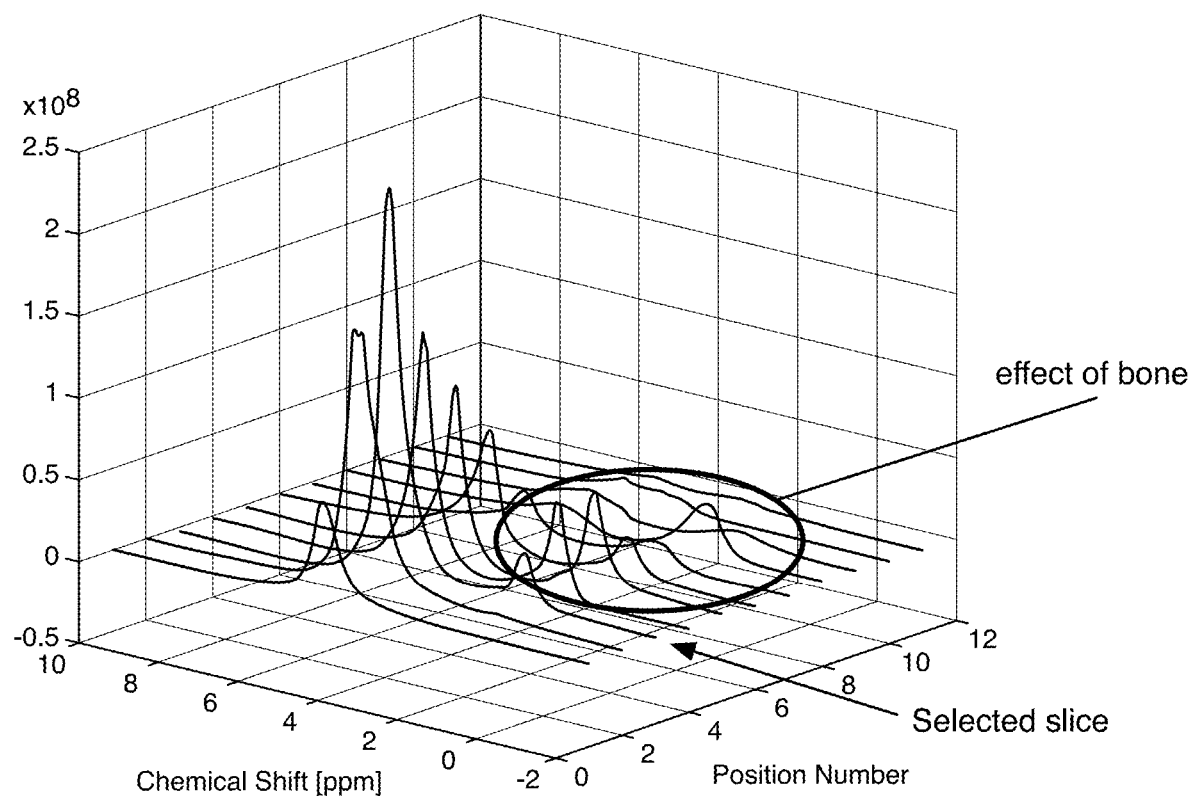
FIG. 14 depicts an example of slice selection.

The target region can optionally be determined based on the composition of the target region. For example, the target region can be determined based on lipid content, water content, lipid compartments, water compartments, parameters thereof (e.g., location, composition, etc.), and/or any other composition parameters of the target region. In a specific example, the target region is determined such that signal artifacts due to bone are reduced and/or signal strength from blood is increased. An example is shown in FIG. 14. In another specific example, the target region is determined such that a concentration of lipids in the target region is reduced (e.g., minimized) and/or the concentration of water in the target region is increased (e.g., maximized).

However, the system 10 can be otherwise calibrated.

Applying a pulse sequence S300 functions to perform one or more measurement scans to determine analyte levels in the sample. S300 can be performed after S100, concurrently with S100 (e.g., while active shimming), after S200, concurrently with S200 (e.g., where measurement scans include calibration scans), and/or at any other time. Specific examples of pulse sequences are shown in FIGS. 17A-17E, FIG. 18, and FIGS. 21A-21G.

Figure 21A:
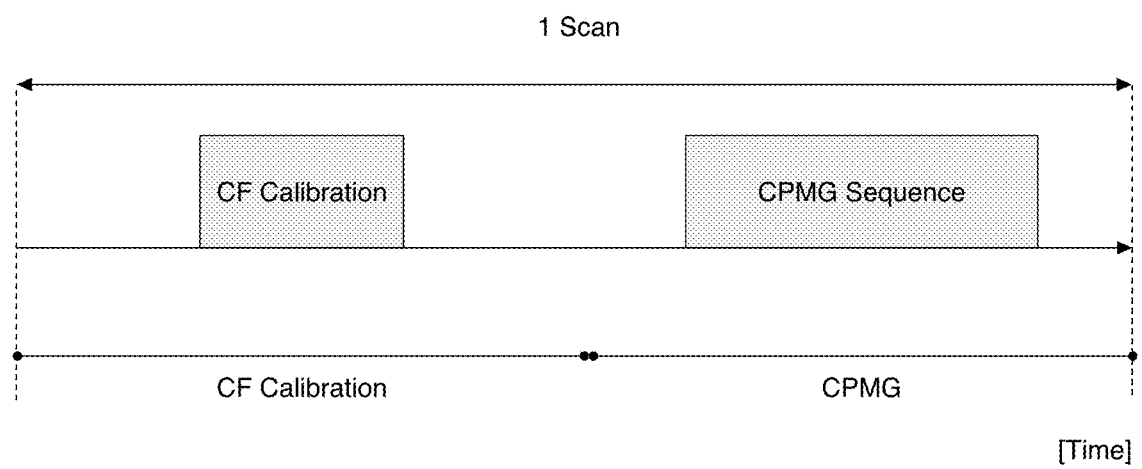
FIG. 21A depicts another example of a measurement scan sequence.
Figure 21B:
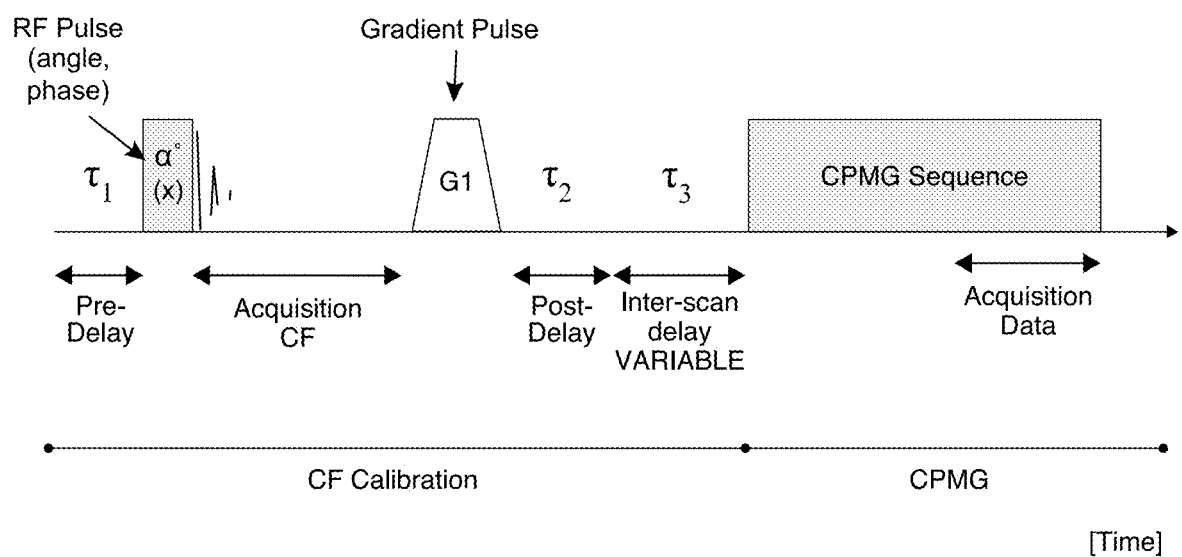
FIG. 21B depicts an example of a calibration sequence.
Figure 21C:
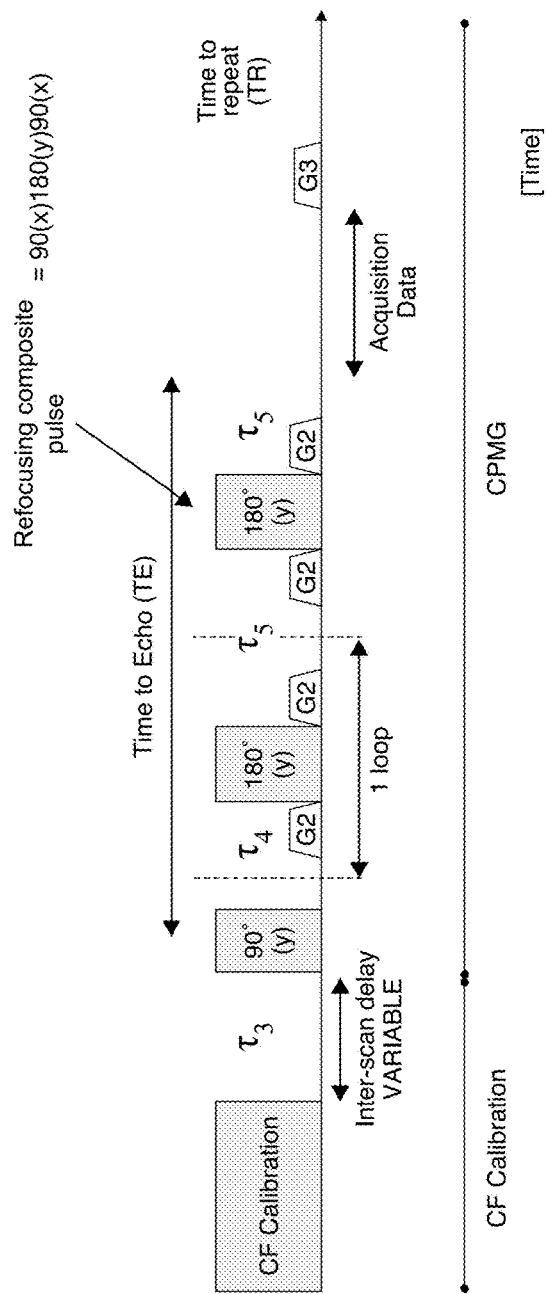
FIG. 21C depicts another example of a measurement scan sequence including a CPMG sequence.
Figure 21D:
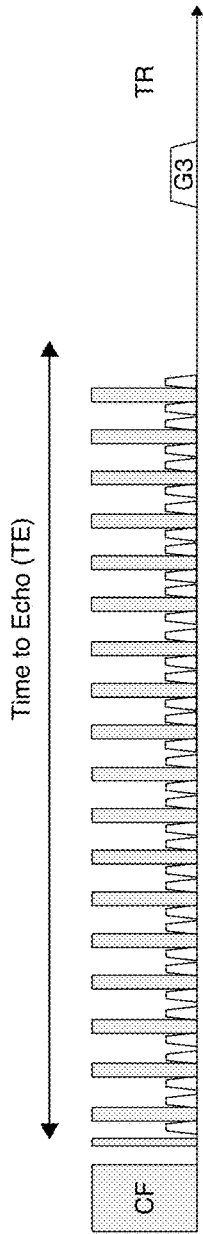
FIG. 21D depicts an example of a measurement scan sequence including a CPMG sequence with 18 loops.
Figure 21E:
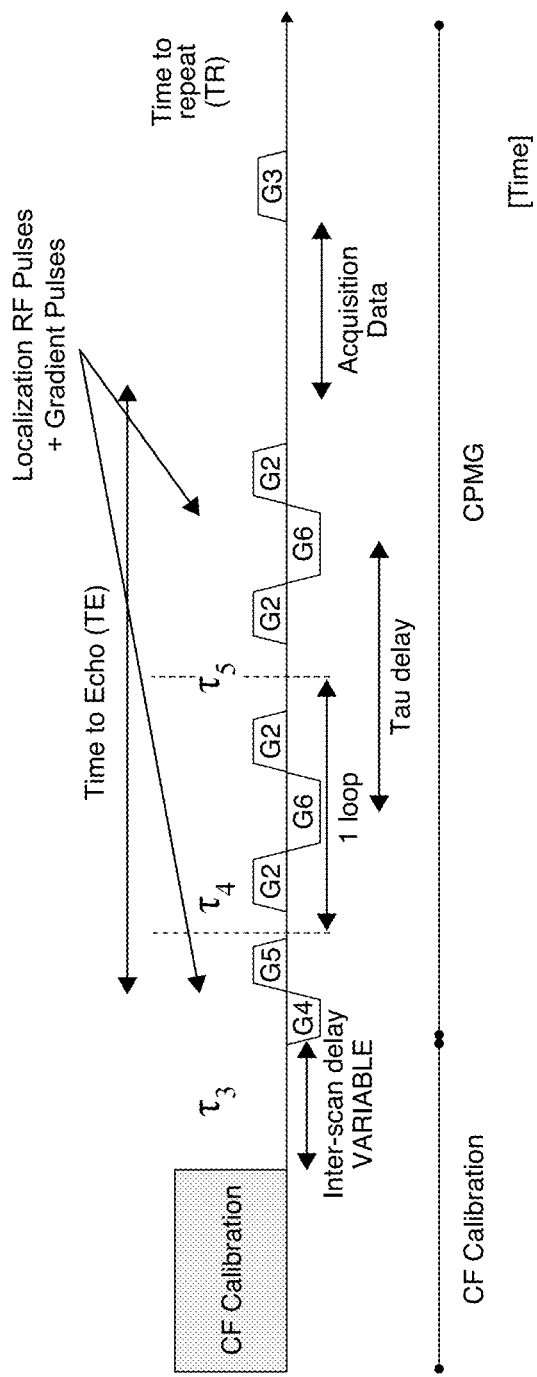
FIG. 21E depicts an example of a measurement scan sequence including a localized CPMG sequence.
Figure 21F:
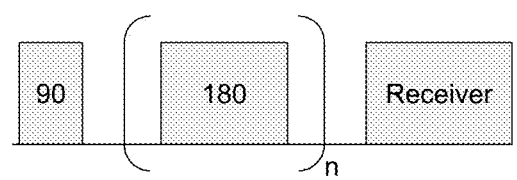
FIG. 21F depicts an example of phase cycle steps for a CPMG pulse sequence.

The number of measurement scans can be between 1-1000 or any range or value therebetween (e.g., 100-500, 200-300, 264, etc.). All or a subset of the measurement scans can be used to determine analyte levels in the sample. For example, one or more initial measurement scans can be dummy scans, which can function to equilibrate the system 10. Dummy scans are preferably not used to determine analyte levels, but can alternatively be used to determine analyte levels. The number of dummy scans can be between 0-50 or any range or value therebetween (e.g., 4-12, 8, etc.). Measurement scans can optionally be phase cycled (e.g., wherein the number of scans is a multiple of the number of phase cycle steps). For example, the number of phase cycle steps can be between 2-64 or any range or value therebetween (e.g., 4, 8, 16, etc.), but can alternatively be less than 2 or greater than 64. An example is shown in FIG. 21F. Phase cycles with more than one refocusing pulse can optionally be implemented. The number of dummy scans is preferably a multiple of the number of phase cycling steps, but can alternatively not be a multiple of the number of phase cycling steps. A measurement scan can optionally include a calibration scan.

Applying a pulse sequence can include transmitting a pulse sequence associated with a set of sequence parameters to the transmit coil 320. The pulse sequence(s) can optionally function to isolate a resulting signal acquired from the analyte in the sample (e.g., dampening and/or separating signal received from water, reducing signal from lipids, refocusing J evolution, etc.). For example, a pulse sequence can include a sequence of one or more pulses and/or one or more delays (e.g., between pulses). Sequence parameters can be static, adjustable (e.g., adjustable based on a known, predicted, or estimated reference frequency; adjustable based on a target region; etc.), and/or otherwise configured. Sequence parameters can be predetermined, automatically determined, manually determined, randomly determined, determined based on the target region, determined based on calibration measurements, determined based on simulations, and/or otherwise determined. Examples of sequence parameters include: pulse type, pulse shape (e.g., square wave, trapezoidal, gaussian, etc.), number of pulses, pulse duration (e.g., width), frequency parameters (e.g., characteristic frequency, modulation frequency, frequency range, bandwidth, pattern, etc.), amplitude, tip angle (e.g., flip angle), timing parameters (e.g., pulse times, delay times, loop times, repetition times, echo time, etc.), and/or any other parameters. Types of pulses can include: adiabatic pulses, Shinnar-Le Roux (SLR) pulses, composite pulses, hard pulses (e.g., square pulses), shaped pulses (e.g., Gaussian, sinc, truncated-sinc, etc.), a combination thereof, and/or any other pulse type. Pulses can be excitation pulses, refocusing pulses, inversion pulses, supplemental pulses, and/or any other pulse. Examples of pulse sequences and/or pulse sequence techniques can include: gradient echo, spin echo, gradient echo train, phase cycling, Carr-Purcell-Meiboom-Gill (CPMG), Localization through Adiabatic SElective Refocusing (LASER), Semi-LASER, Point Resolved Spectroscopy (PRESS), Stimulated Echo Acquisition Mode (STEAM) (e.g., for a T2 relaxation measurement), T1-filtering, T2-filtering, perfect echo, XY-based sequences, KDD sequences, slice-selective sequencing, averaging techniques, a combination thereof and/or any other pulse sequence and/or pulse sequence technique.

The pulse sequence can have an echo time between 5 ms-500 ms or any range or value therebetween (e.g., 5 ms-500 ms, 50 ms-200 ms, 70 ms-150 ms, 70 ms-100 ms, greater than 50 ms, greater than 75 ms, greater than 100 ms, less than 100 ms, less than 150 ms, less than 200 ms, etc.), but can alternatively be less than 5 ms or greater than 500 ms. T1-filtering, T2-filtering (e.g., using an echo time greater than a threshold), and/or a combination of T1-filtering and T2-filtering can be optionally used. In a specific example, water in the sample can exhibit different T2 relaxation parameters, with a first subset of the water relaxing faster than a second subset of the water; the fast-relaxing water can optionally be filtered out using a T2 filter (e.g., wherein the analyte can exhibit a slower relaxation).

Figure 19A:
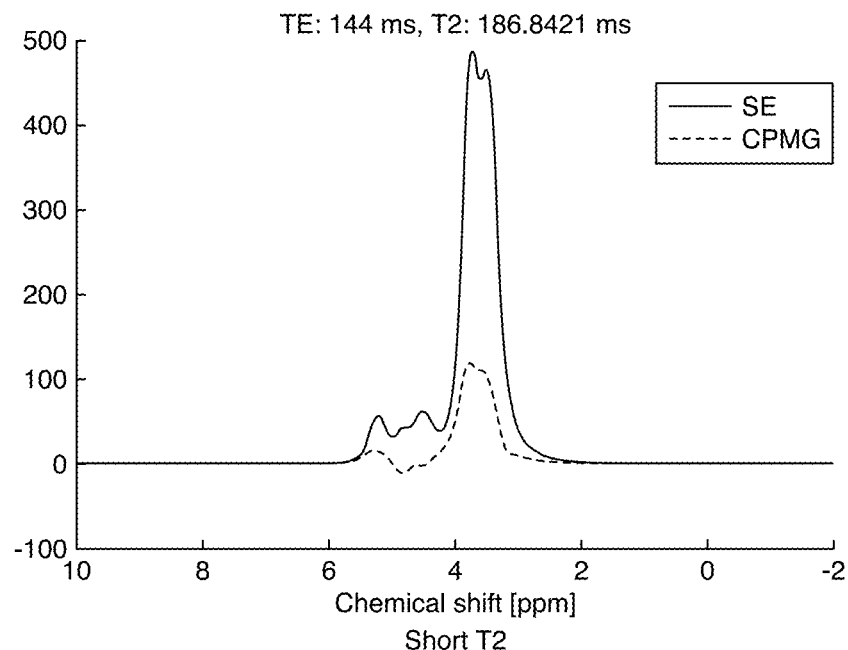
FIGS. 19A and 19B depict examples of simulations of signals acquired using a spin echo (SE) pulse sequence and a CPMG pulse sequence, the measured signals corresponding to a blood analyte.
Figure 19B:
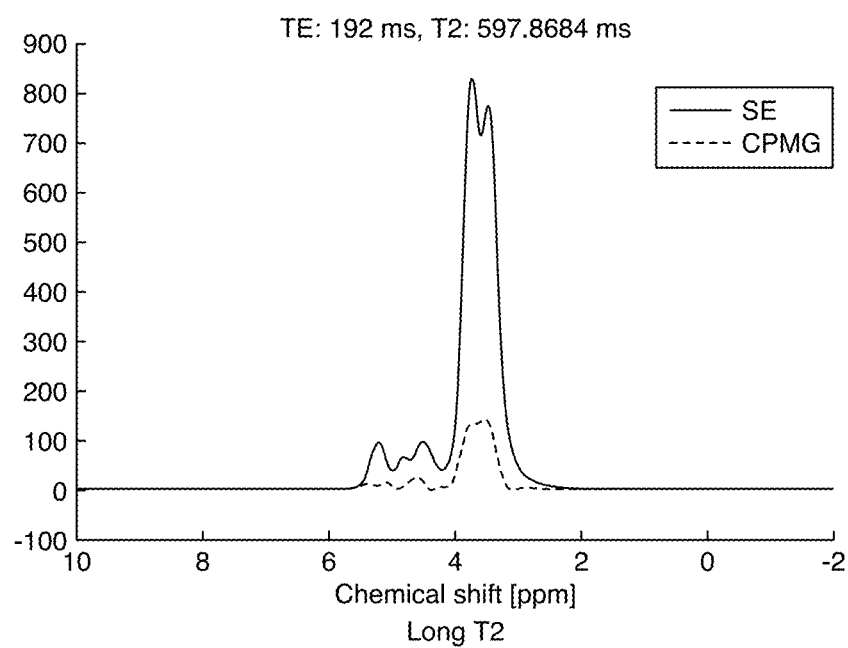
Figure 20:
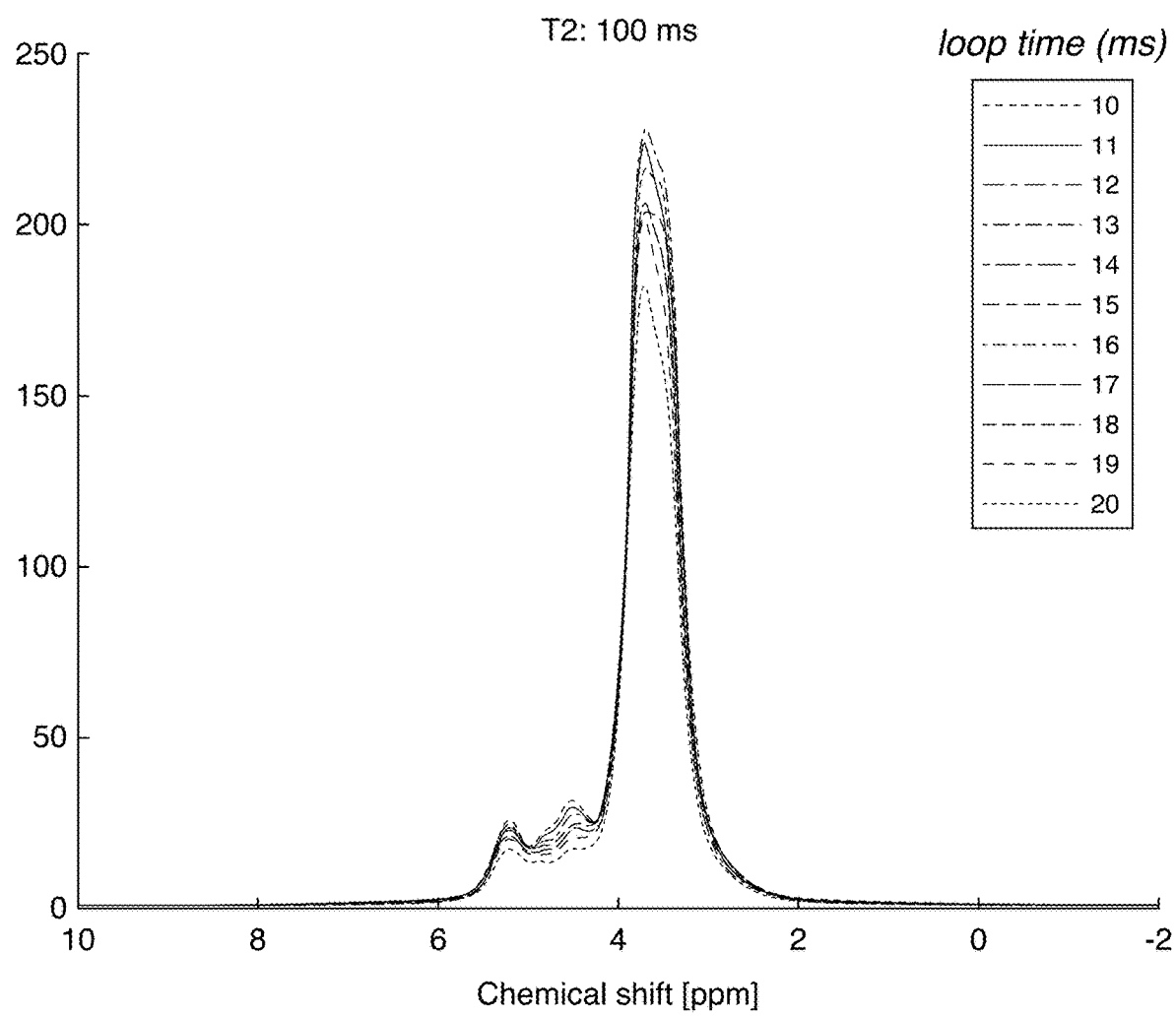
FIG. 20 depicts examples of measured signals acquired using a pulse sequence with loop times between 10 ms and 20 ms.

The pulse sequence preferably includes one or more refocusing pulses (e.g., a train of refocusing pulses), but can alternatively not include refocusing pulses. In a specific example, refocusing pulses can function to refocus the J-coupling evolution of the analyte, which can improve parameters of the signal received from the analyte (e.g., increased signal amplitude, reduced dephasing, etc.). Examples of simulated signals corresponding to a spin echo (SE) pulse sequence (without a train of refocusing pulses) and a CPMG pulse sequence (with a train of refocusing pulses) are shown in FIG. 19A and FIG. 19B. In an example, the pulse sequence can include an excitation pulse, one or more refocusing pulses, and optionally one or more supplemental pulses (e.g., 90° pulses between refocusing pulses and/or any other additional pulses). In a specific example, a pulse sequence and/or subsequences thereof can include one or more loops, wherein each loop includes a refocusing pulse, an optional supplemental pulse, and optional delays. The delay between loops is preferably zero, but can alternatively be nonzero. The number of loops can be between 1-1000 or any range or value therebetween (e.g., 2-20, 2-6, 8-12, 5-50, 6, 12, 14, 16, 18, 20, etc.), but can alternatively be greater than 1000. The number of loops can optionally be determined based on the loop time, the echo time, and/or other timing parameters. The number of loops is preferably an even number, but can alternatively be an odd number. The excitation pulse can have a pulse width between 1 μs-10 ms or any range or value therebetween (e.g., 1 ms-5 ms, 1 ms, 2 ms, 3 ms, 4 ms, etc.), but can alternatively be less than 1 us or greater than 10 ms. The excitation pulse preferably has a tip angle of 90°, but can alternatively have any other tip angle. Each refocusing pulse can have a pulse width between 1 ms-30 ms or any range or value therebetween (e.g., less than 20 ms, less than 15 ms, less than 10 ms, less than 5 ms, etc.), but can alternatively be less than 1 ms or greater than 30 ms. Each refocusing pulse preferably has a tip angle of 180°, but can alternatively have any other tip angle. The delay between the excitation pulse and the first refocusing pulse can be between 0 μs-50 ms or any range or value therebetween (e.g., 1 ms-5 ms, 2 ms, etc.), but can alternatively be greater than 50 ms. The loop time for a train of refocusing pulses can be between 0 ms-100 ms or any range or value therebetween (e.g., 10 ms-20 ms, 10 m-15 ms, less than 20 ms, less than 18 ms, less than 16 ms, less than 15 ms, less than 14 ms, less than 12 ms, less than 10 ms, etc.), but can alternatively be greater than 100 ms. In a specific example, a loop time less than a threshold value can reduce dephasing of the analyte signal; an example is shown in FIG. 20. The loop time can optionally be fixed or variable (e.g., dependent on measured T1 parameters of the sample). The loop time can optionally be dependent on whether an intervening pulse (e.g., a 90° supplemental pulse in a perfect echo sequence) is used between refocusing pulses. For example, the loop time can be less than a first threshold for a CPMG sequence, and less than a second threshold for a perfect echo sequence (e.g., wherein the second threshold is greater than the first threshold). The delay between pulses (e.g., between refocusing pulses, between a refocusing pulse and a supplemental 90° pulse, etc.) can be between 0 μs-50 ms or any range or value therebetween (e.g., 1 ms-5 ms), but can alternatively be greater than 50 ms. The delay ($\tau$) between pulses is preferably less (e.g., significantly less) than $1/J$ (e.g., $\tau \ll 1/|J|$), where J is the maximum J-coupling constant for the analyte, but can alternatively be greater than $1/J$.

In an example, the pulse sequence can include an excitation pulse, a first pulse subsequence (e.g., a first train of refocusing pulses), and a second pulse subsequence (e.g., a second train of refocusing pulses). In a specific example, the excitation pulse is selective excitation pulse (e.g., with target region selection via the set of gradient coils 360). In a specific example, the first pulse subsequence is a non-selective subsequence (e.g., without target region selection via the set of gradient coils 360). In a specific example, the second pulse subsequence is a selective subsequence (e.g., with target region selection via the set of gradient coils 360).

Figure 6A:
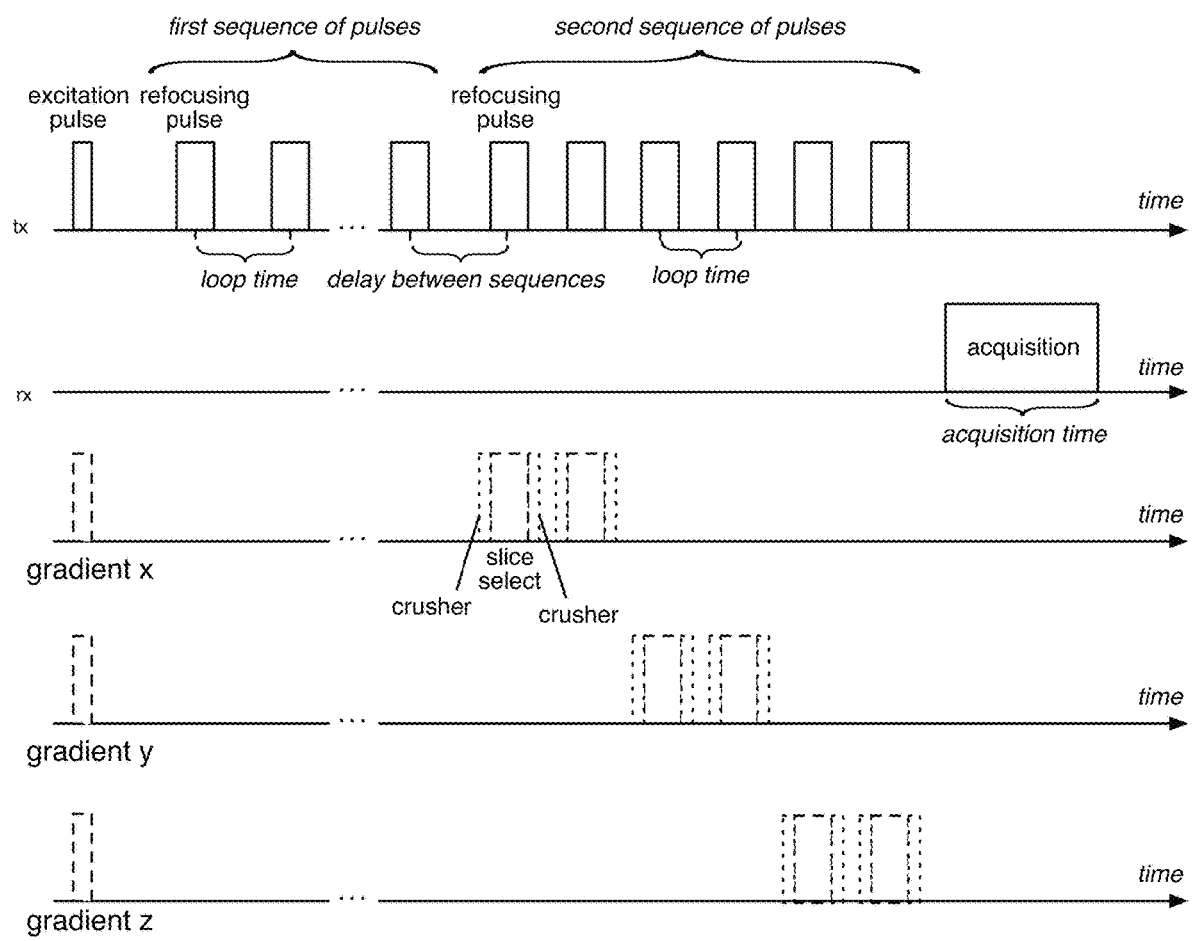
FIG. 6A depicts an example of a measurement scan sequence including a first set of refocusing pulses (e.g., a Carr-Purcell-Meiboom-Gill (CPMG) sequence) and a second set of slice-selective refocusing pulses (e.g., a CPMG laser sequence).

The number of loops in the first pulse subsequence can be between 2-12 or any range or value therebetween (e.g., 2, 4, 6, less than 10, less than 6, etc.), but can alternatively be less than 2 or greater than 12. The number of loops in the second pulse subsequence can be between 2-12 or any range or value therebetween (e.g., 2, 4, 6, less than 10, less than 6, etc.), but can alternatively be less than 2 or greater than 12. The loop time for the first pulse subsequence and/or the second pulse subsequence can be between 0 ms-100 ms or any range or value therebetween (e.g., 10 ms-20 ms, 10 m-15 ms, less than 20 ms, less than 18 ms, less than 16 ms, less than 15 ms, less than 14 ms, less than 12 ms, less than 10 ms, etc.), but can alternatively be greater than 100 ms. In an example, the second pulse subsequence can include one or more pairs of refocusing pulses, wherein each pair corresponds to (e.g., is concurrent with) a pair of gradient pulses on a gradient coil in the set of gradient coils 360. In a specific example, the second pulse subsequence includes three pairs of refocusing pulses, wherein each pair is slice selective in a different direction (e.g., the first pair is slice selective in a first direction using a first gradient coil, the second pair is slice selective in a second direction using a second gradient coil, and the third pair is slice selective in a third direction using a third gradient coil). In a specific example, the second pulse subsequence includes three pairs of refocusing pulses, and the sequence of gradient pulses includes three pairs of gradient pulses, each pair of gradient pulses corresponding to a different direction. An example is shown in FIG. 6A. In an illustrative example, the first pulse subsequence includes a CPMG sequence and the second pulse subsequence includes a CPMG LASER sequence.

Figure 6B:
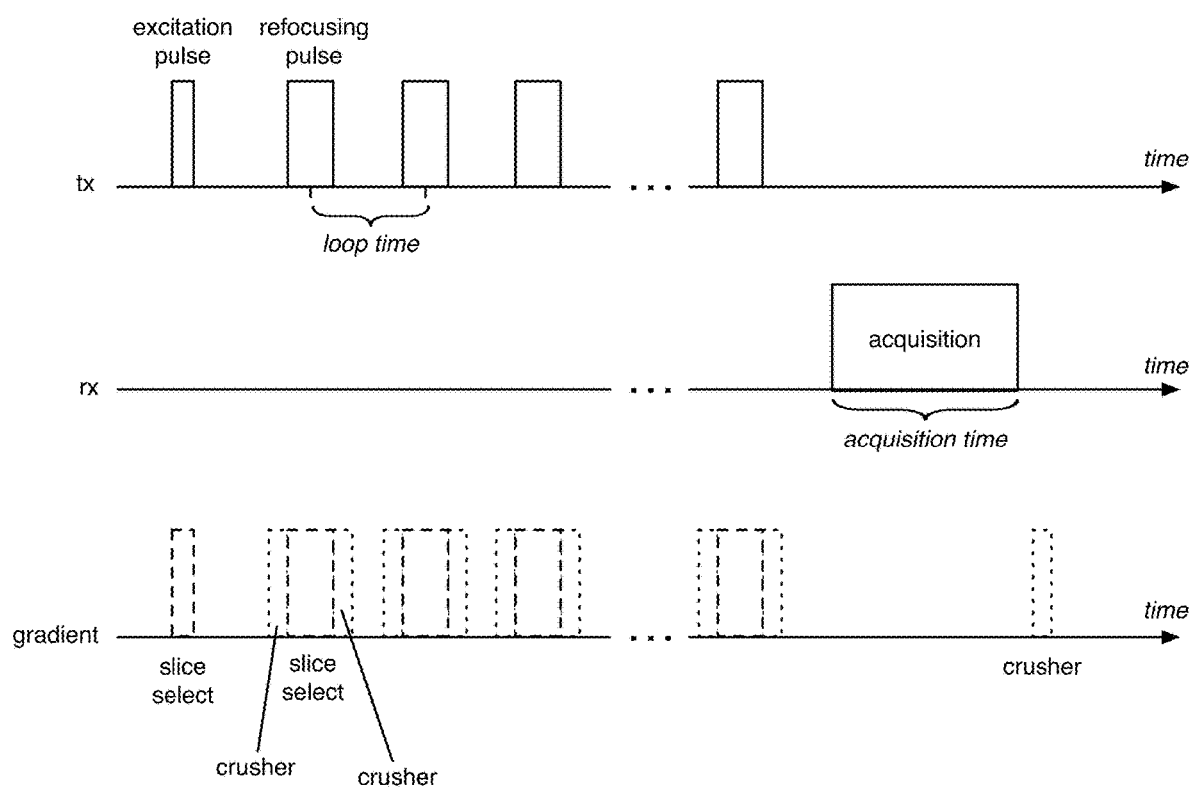
FIG. 6B depicts an example of a measurement scan sequence including a set of refocusing pulses.
Figure 7A:
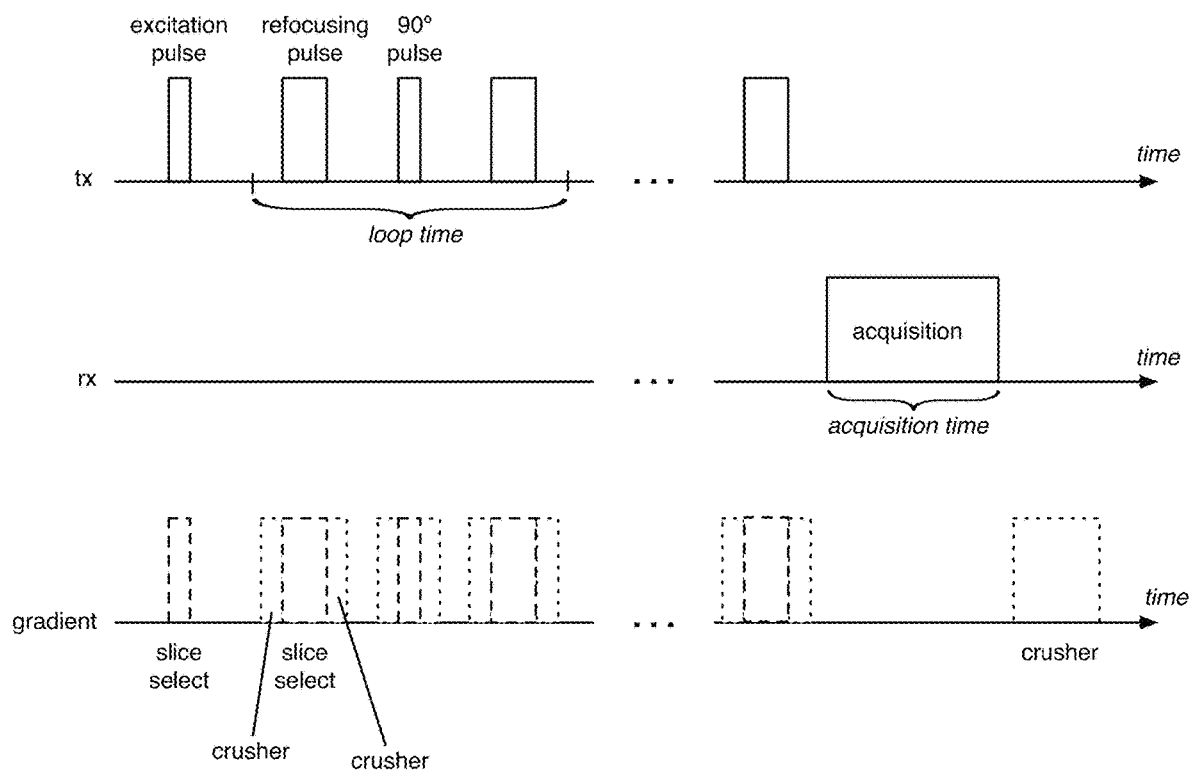
FIGS. 7A-7B depict examples of a measurement scan sequence including a perfect echo sequence.
Figure 7B:
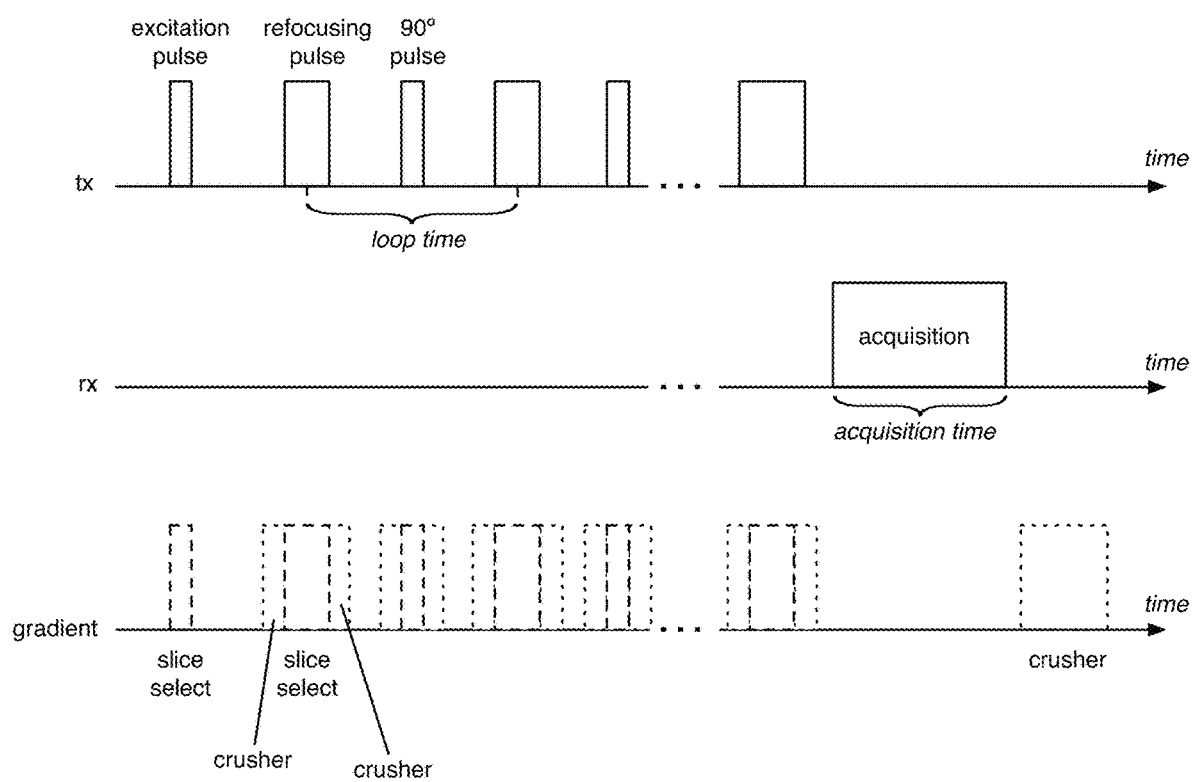
Figure 8A:
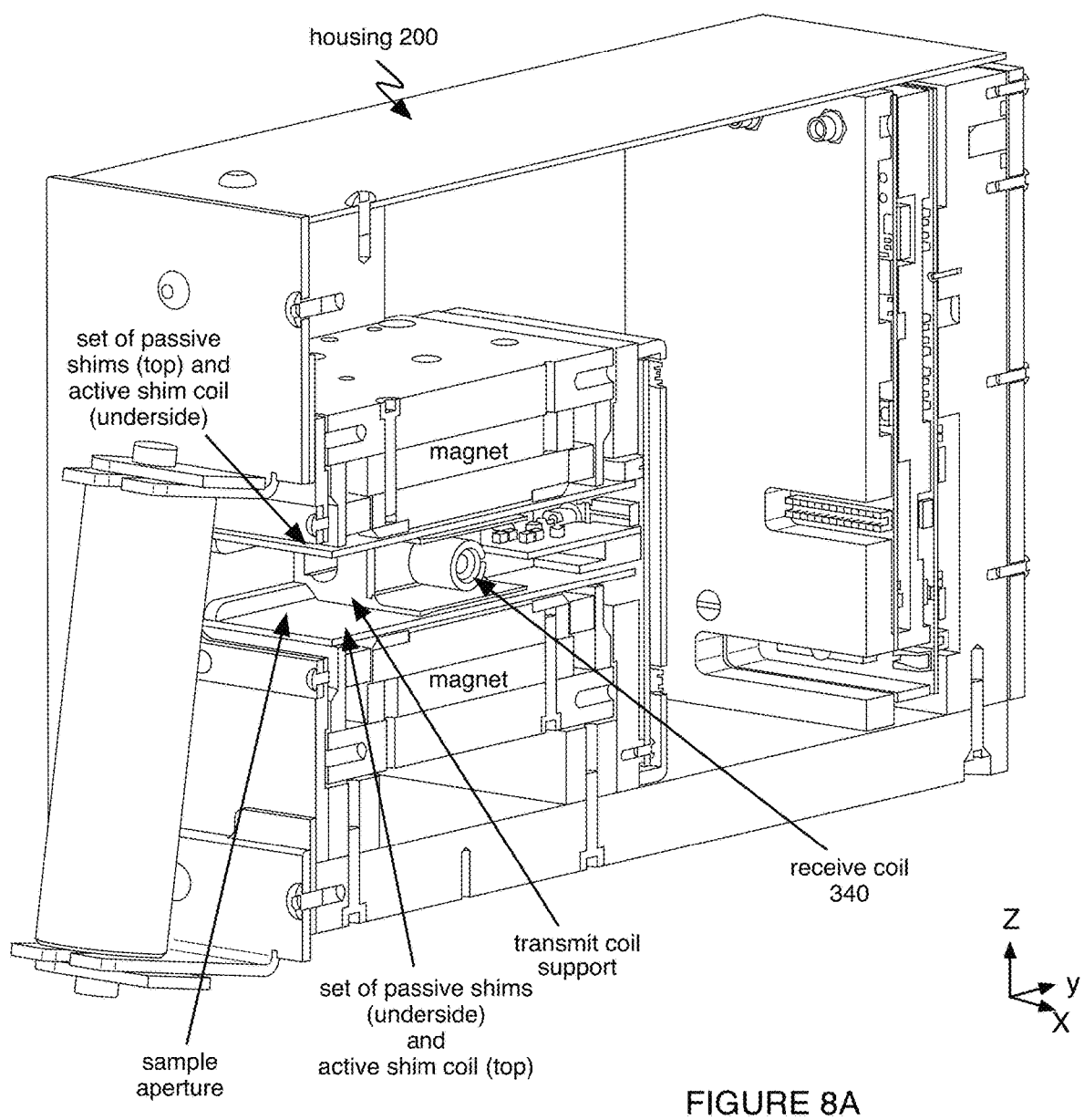
FIG. 8A is a cross-sectional view of an example of the system.
Figure 8B:
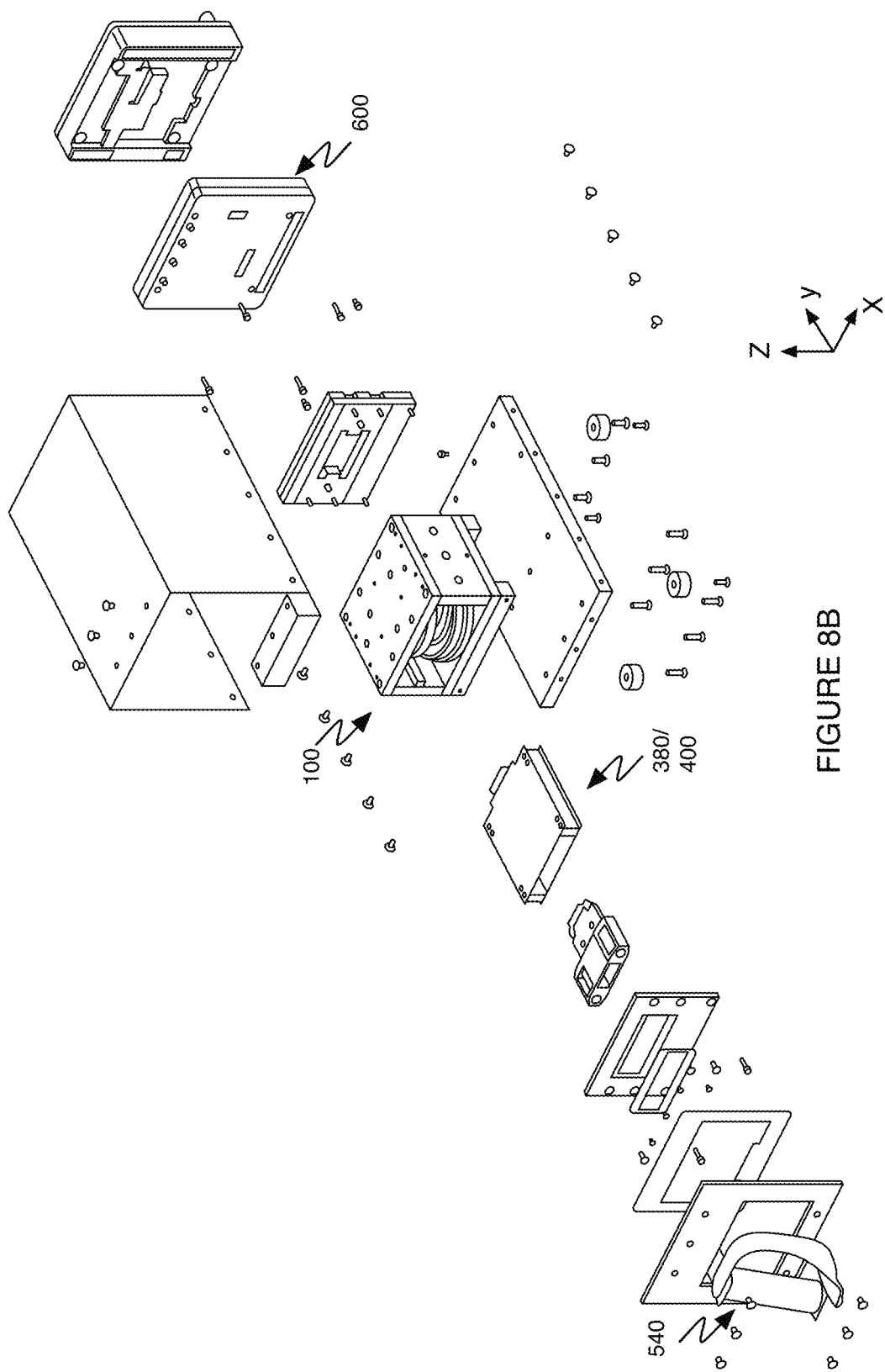
FIG. 8B is an exploded view of an example of the system.
Figure 8C:
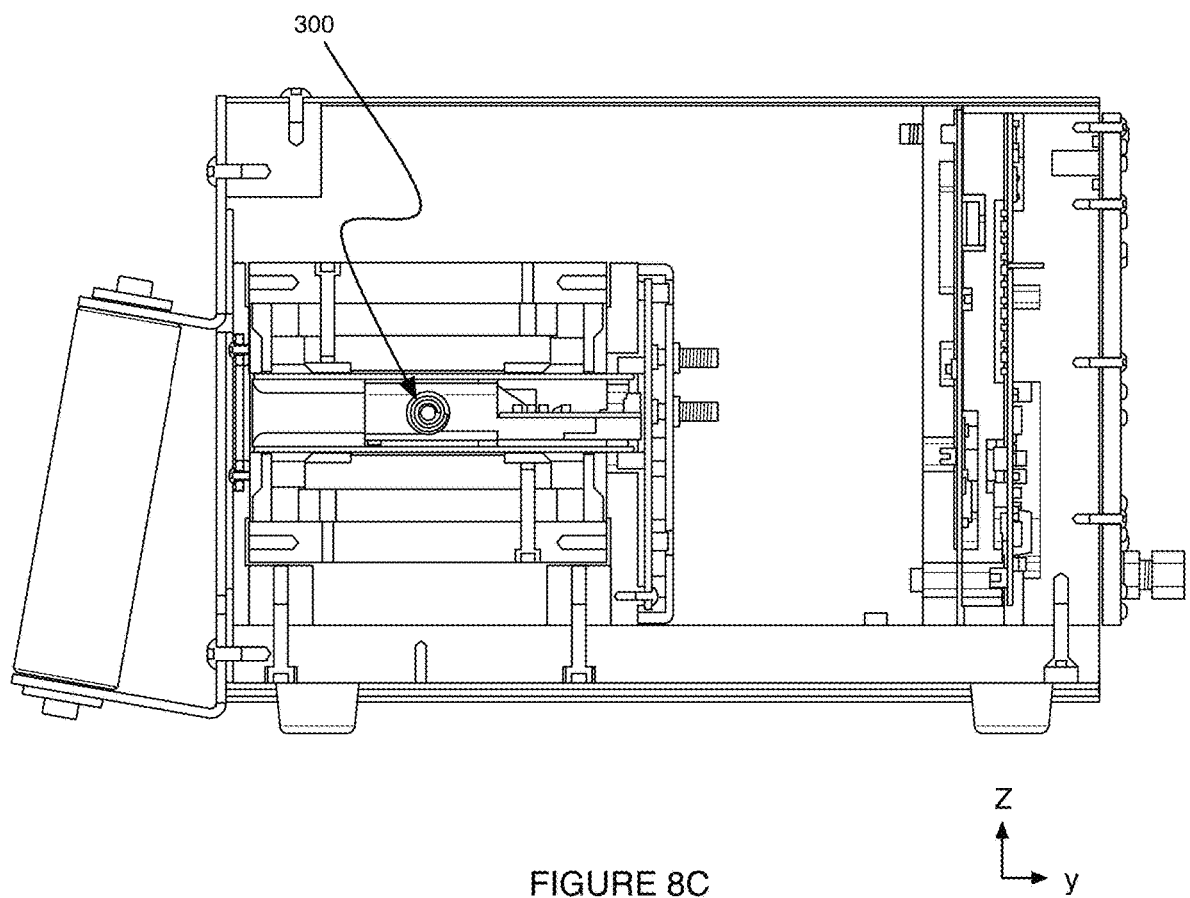
FIGS. 8C-8G are cross-sectional views of an example of the system.
Figure 8D:
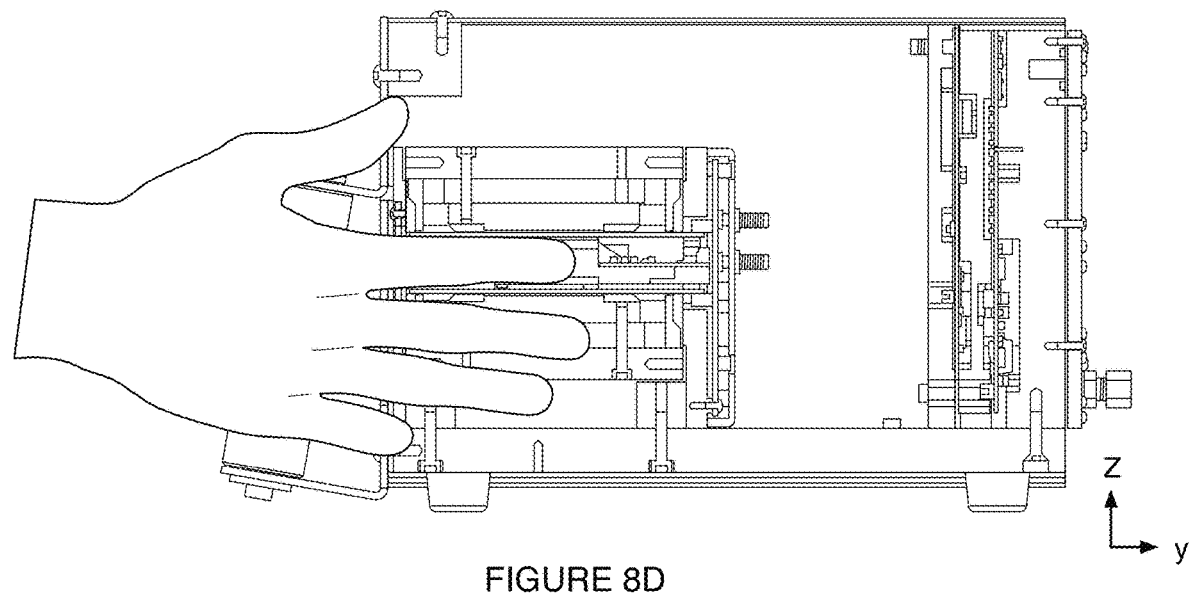
Figure 8E:
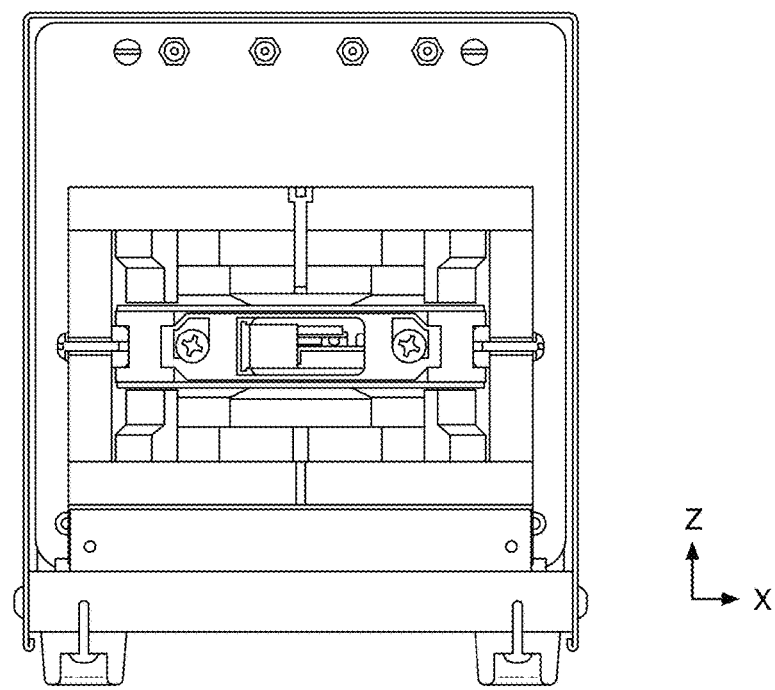
Figure 8F:
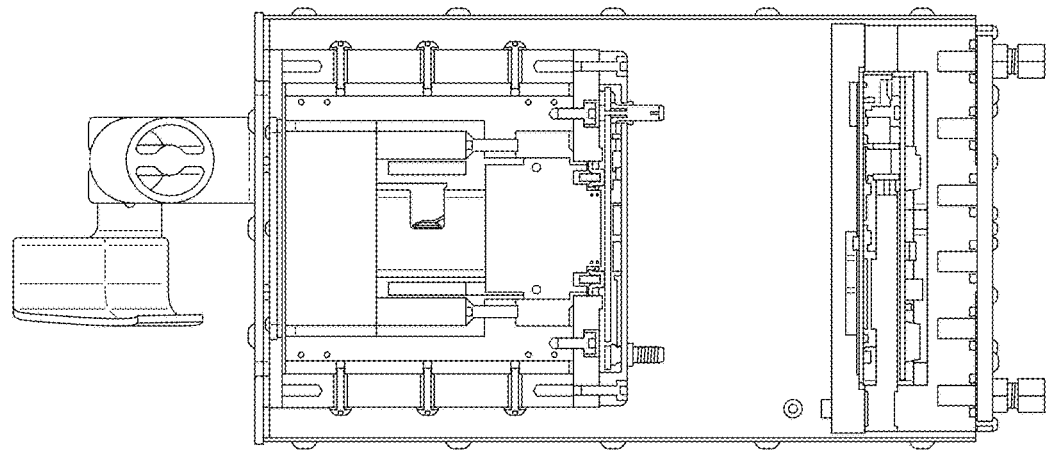
Figure 8G:
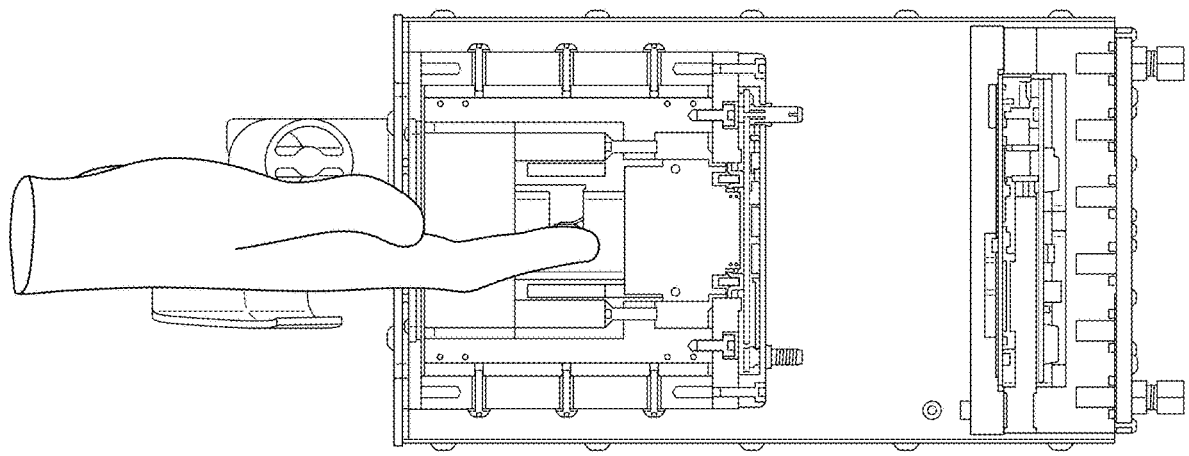
Figure 8H:
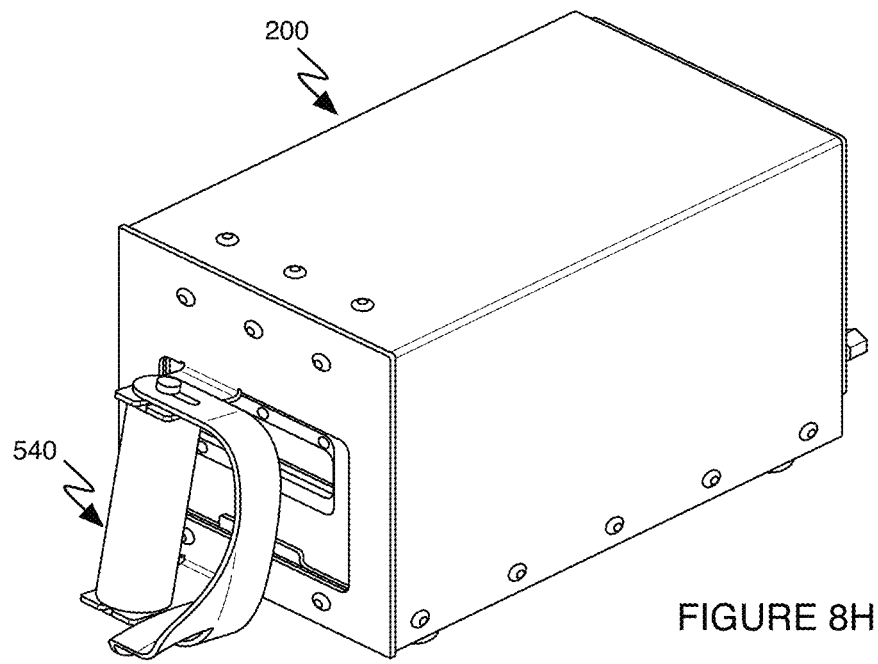
FIGS. 8H-8J depict examples of the system.
Figure 8I:
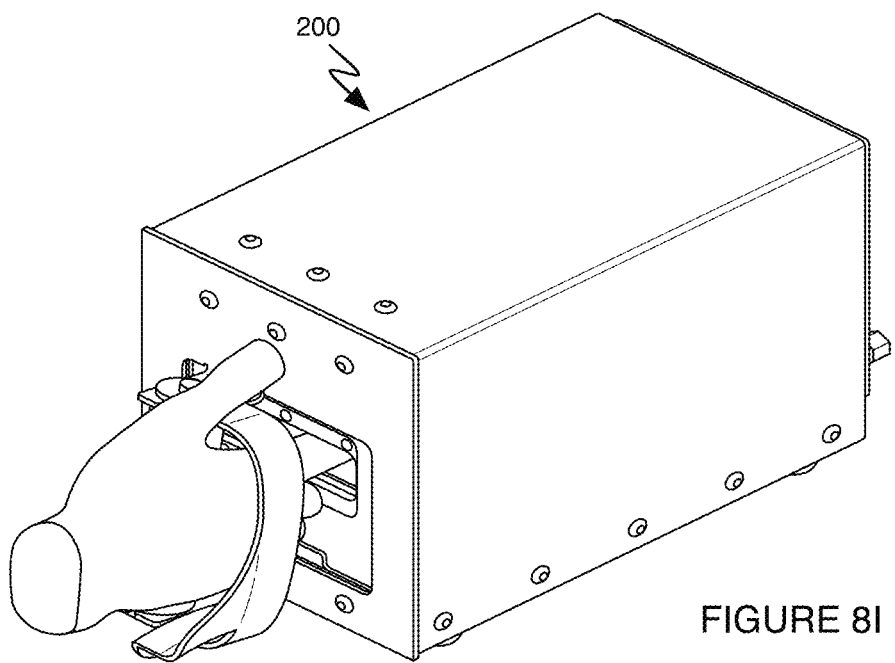
Figure 8J:
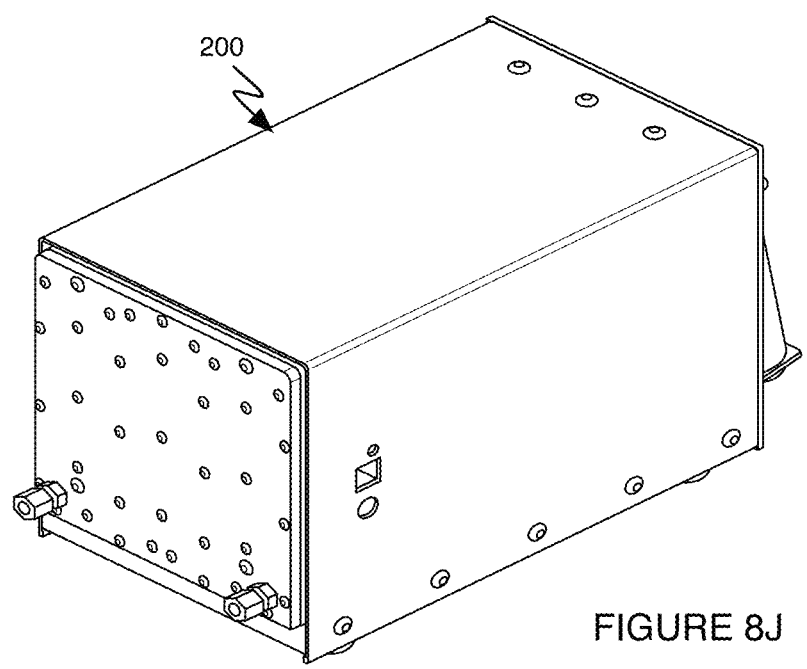
Figure 8K:
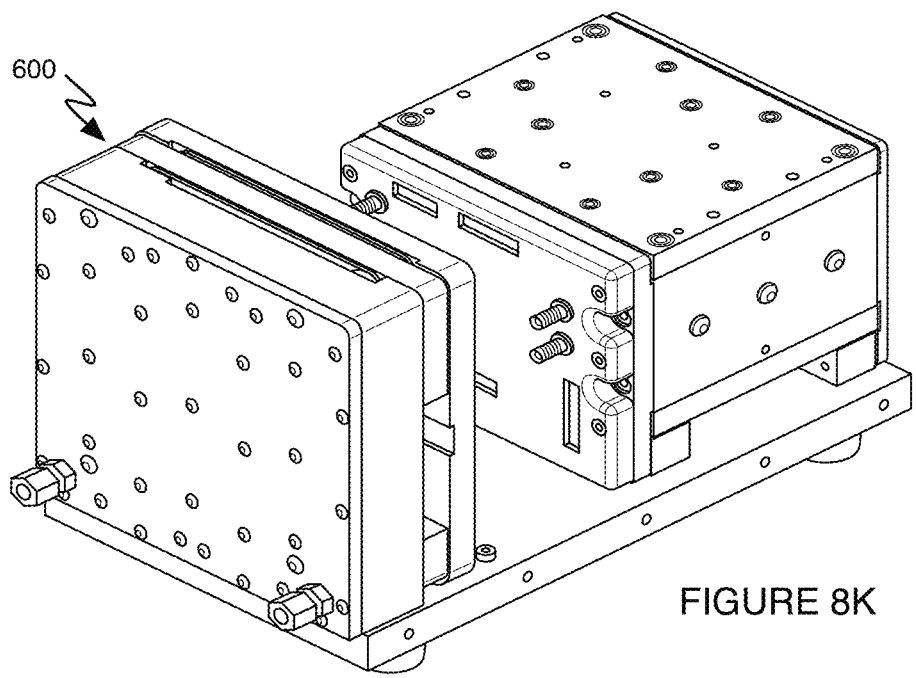
FIGS. 8K and 8L depict examples of the system without an enclosure.
Figure 8L:
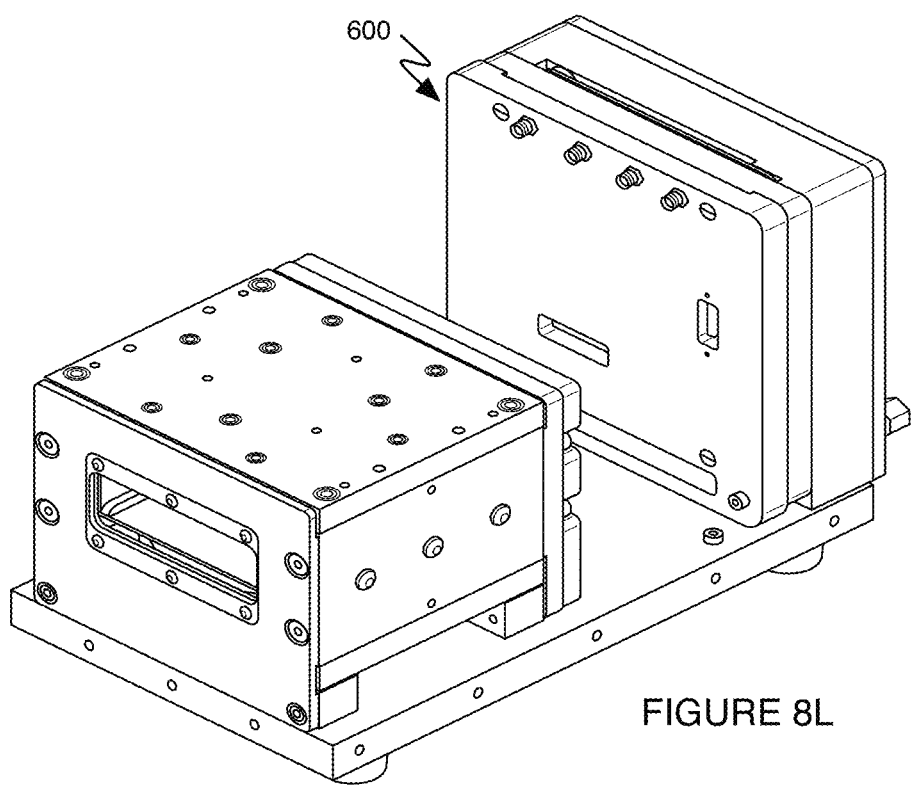
Figure 21G:
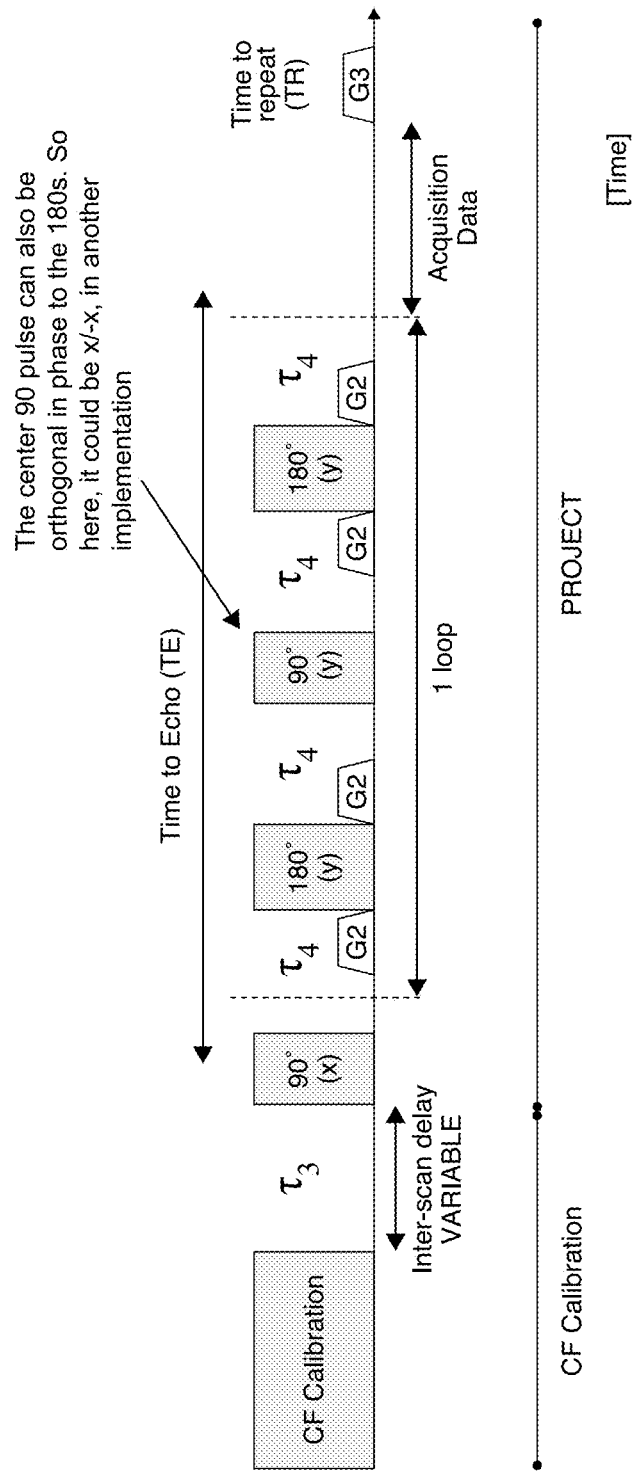
FIG. 21G depicts an example of a measurement scan sequence including a Periodic Refocusing of J Evolution by Coherence Transfer (PROJECT) sequence.
Figure 22:
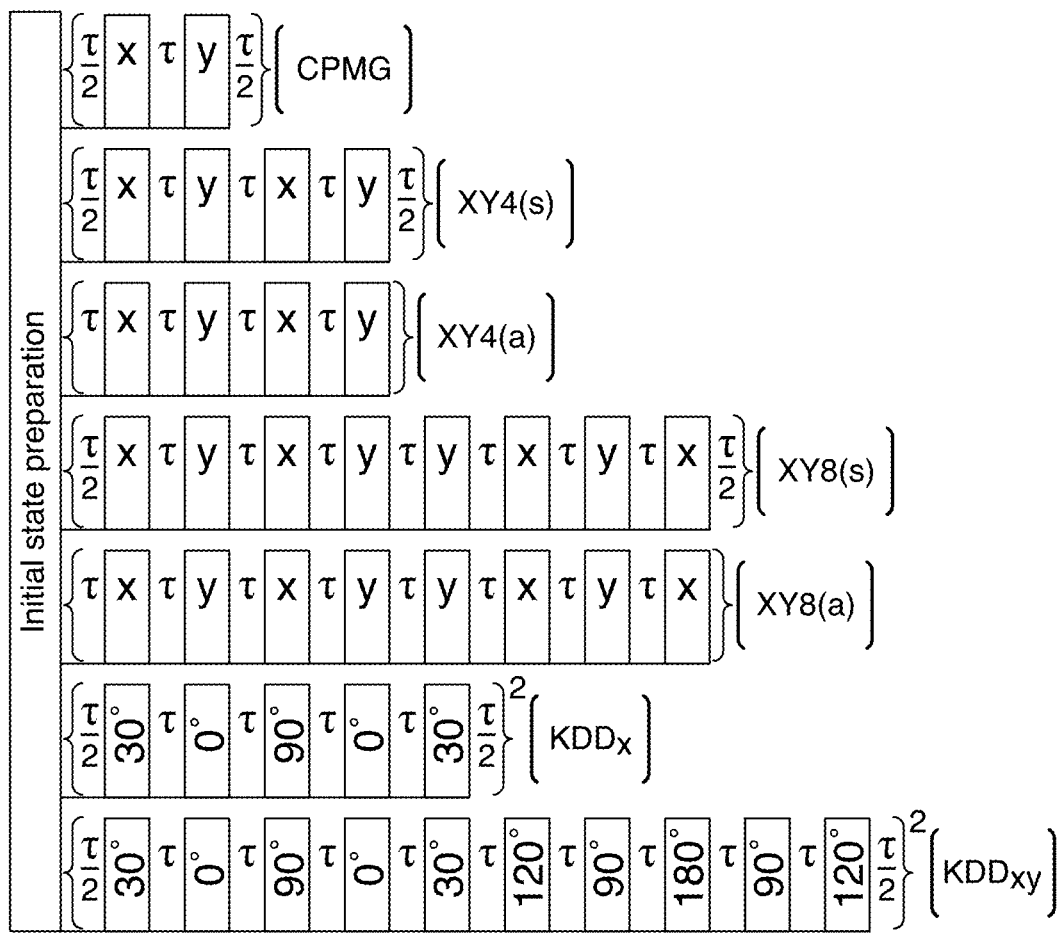
FIG. 22 depicts examples of pulse sequences.

In a first example, the pulse sequence includes a CPMG sequence and/or a CPMG LASER sequence; examples are shown in FIG. 6A and FIG. 6B. In a second example, the pulse sequence includes a perfect echo sequence (e.g., Periodic Refocusing of J Evolution by Coherence Transfer (PROJECT)) and/or a modified perfect echo sequence; examples are shown in FIG. 7A, FIG. 7B, and FIG. 21G. In a third example, the pulse sequence includes an XY-based pulse sequence (e.g., XY16, XY4, XY4a, XY8, etc.); an example is shown in FIG. 22. In a specific example, a combination of CPMG and spin echo can be used to determine analyte levels (e.g., differences between a signal acquired using CPMG and a signal acquired using spin echo).

In a first illustrative example, sequence parameters can include any or all of: T2 filter (e.g., echo time of at least 50 ms, echo time of at least 70 ms, echo time of at least 100 ms, etc.), CPMG, CPMG LASER, and/or a loop time less than 20 ms (for both CPMG and CPMG LASER). In a second illustrative example, sequence parameters can include any or all of: T2 filter (e.g., echo time of at least 50 ms, echo time of at least 70 ms, echo time of at least 100 ms, etc.), localized CPMG, and/or a loop time less than 20 ms. In a third illustrative example, sequence parameters can include any or all of: T2 filter, perfect echo (e.g., localized perfect echo), and/or a loop time less than 50 ms. In a fourth illustrative example, sequence parameters can include any or all of: localized spin echo, echo time (TE) approximately 200 ms, 64×2 scans, and/or repetition delay approximately 2 seconds. In a fifth illustrative example, sequence parameters can include a T2 filter with any or all of: localized CPMG, 16 loops, TE approximately 12.5 ms, total TE=200 ms, 128 scans, and/or a repetition delay approximately 2 sec. In a sixth illustrative example, sequence parameters can include a T2 filter with any or all of: interleaved combination of spin echo (e.g., adiabatic refocusing) and CPMG, and subtraction of their respective spectra. In a seventh illustrative example, sequence parameters can include (e.g., in addition to a T2 filter): a T1 filter with one or more inversion pulses (e.g., before a localization module with a T2 filter).

The pulse sequence preferably excludes inversion pulses, but can alternatively include inversion pulses. The pulse sequence preferably excludes lipid suppression pulses, but can alternatively include lipid suppression pulses. The pulse sequence preferably excludes lipid suppression filters (e.g., T2 and/or T1 filters that filter lipid signals), but can alternatively include lipid suppression filters.

Averaging techniques can optionally be used. Examples of averaging techniques include: waiting for T1 to recover (e.g., repetition time at least 2 seconds), Ernst angle averaging (e.g., repetition time less than or equal to 2 seconds), and/or any other averaging technique. In a first example, a predetermined number of averages can be used. In a second example, NMR measurement can continue until a criterion is reached (e.g., a target SNR is achieved).

However, one or more pulse sequences can be otherwise applied.

Applying a gradient sequence S400 functions to localize the pulse sequence to a target region (e.g., slice selection), reduce unwanted signals (e.g., a crusher gradient), impart any other gradient, and/or otherwise modulate the magnetic field. In an example, the processing system 600 can transmit a gradient sequence associated with a set of sequence parameters to the set of gradient coils 360. The gradient sequence and/or one or more components (e.g., gradient pulses) therein can be applied concurrently with the pulse sequence and/or one or more components therein (e.g., RF pulses), asynchronously with the pulse sequence and/or one or more components therein, and/or at any other time.

The gradient sequence can optionally include one or more crusher gradients, which can function to reduce unwanted coherences. For example, the crusher gradients can be positioned before a pulse (e.g., excitation pulse, refocusing pulse, etc.), after a pulse, with a delay between the crusher gradient and a pulse, without a delay between the crusher gradient and a pulse, concurrently with a pulse, a combination thereof, and/or at any other time. In a specific example, when the pulse sequence (transmitted to the transmit coil 320) includes one or more refocusing pulses (e.g., a CPMG sequence, a perfect echo sequence, etc.), gradient crushers can be applied around all or a subset of the refocusing pulses. In another specific example, a gradient crusher can be applied after acquiring a signal.

The gradient sequence (e.g., a localized sequence) can optionally include one or more selective gradients (e.g., slice selective gradients), which can function to localize all or a portion of the pulse sequence to a target region (e.g., slice, column, voxel, any other region, etc.) in the ROI. The selective gradient can be a single-axis selective gradient (e.g., applied via a single-axis gradient coil), a two-axis selective gradient (e.g., applied via a two-axis set of gradient coils), a three-axis selective gradient (e.g., applied via a three-axis set of gradient coils), and/or a gradient along any other dimensions. In examples, the selective gradients can be positioned before a pulse, after a pulse, concurrently with a pulse, a combination thereof, and/or at any other time. In a specific example, when a selective gradient can be applied during all or a subset of excitation pulses, refocusing pulses, supplemental pulses, and/or any other pulses of the pulse sequence. Parameters for the gradient sequence can be determined based on the target region (e.g., automatically determined after selecting the target region), automatically determined, manually determined, predetermined, randomly determined and/or otherwise determined.

However, one or more gradient sequences can be otherwise applied.

Figure 25A:
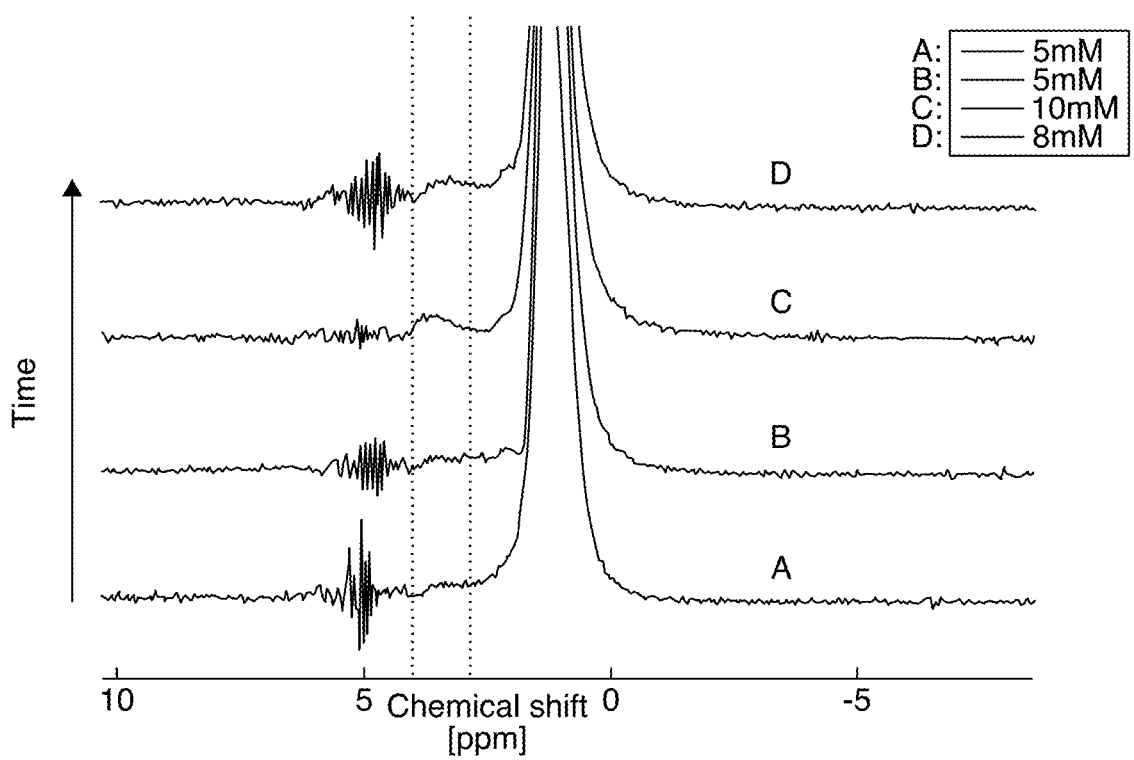
FIG. 25A-25B depicts data showing a response in a measured glucose signal to blood-glucose concentration (e.g., without calibration) in oral glucose tolerance tests. For example, a subject fasts overnight and then consumes 75 g of glucose; the measured glucose signal goes up and down with their blood-sugar.
Figure 26:
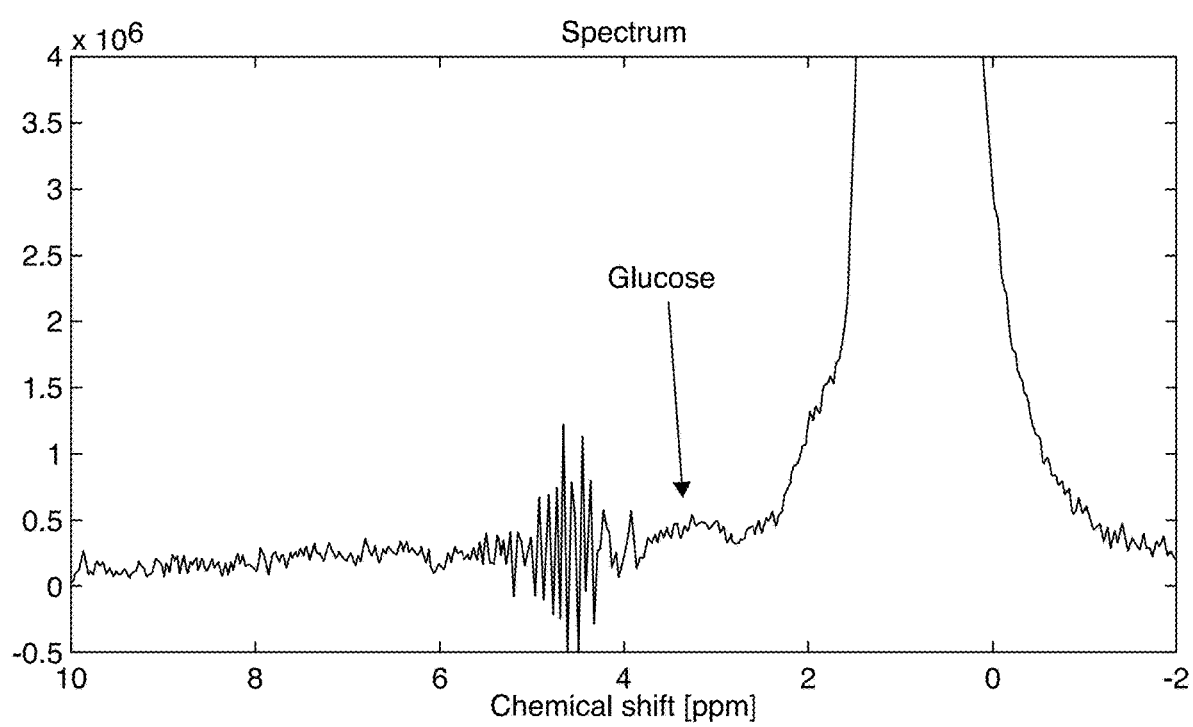
FIG. 26 depicts an example of a measured signal, including a signal corresponding to glucose.
Figure 28:
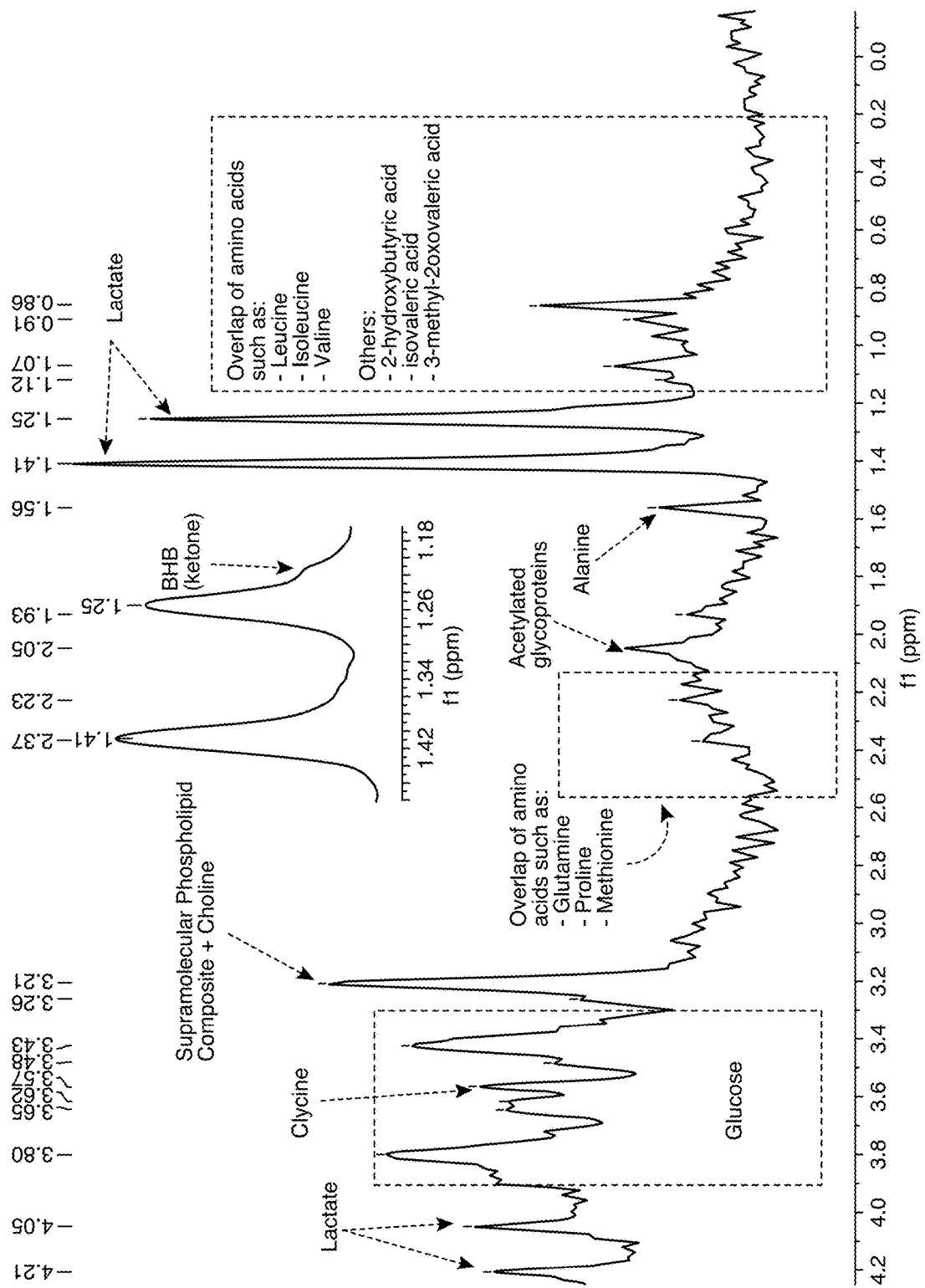
FIG. 28 depicts an example of metabolites identified in a measured signal (e.g., blood magnetic resonance spectrum).

Acquiring a signal S500 functions to measure a signal from the sample (e.g., from the target region of the sample). In an example, the processing system 600 can receive the signal via the receive coil 340. The signal can optionally be received (e.g., sampled) based on one or more acquisition parameters. Acquisition parameters can include time to echo (TE), acquisition time, acquisition frequency, sampling frequency, any sequence parameters, and/or any other suitable parameters. The acquisition time can be between 100 ms-5 s or any range or value therebetween (e.g., 750 ms, greater than 200 ms, greater than 500 ms, greater than 700 ms, etc.), but can alternatively be less than 100 ms or greater than 5 s. Examples of measured signals (e.g., processed or unprocessed measured signals) are shown in FIG. 25A, FIG. 26, and FIG. 28. However, one or more signals can be otherwise acquired.

Processing the signal S600 functions to determine analyte levels and/or generate images of the sample. The signal is preferably a signal received in S500, but can alternatively be any other signal.

Signals can be processed using one or more models. The models can include classical or traditional approaches, machine learning approaches, and/or be otherwise configured. The models can include: neural networks, regression, decision tree, LSA, clustering, association rules, dimensionality reduction, ensemble methods, optimization methods, classification, rules, heuristics, equations (e.g., weighted equations), selection, support vectors, statistical methods, comparison, lookups, regularization methods, Bayesian methods, instance-based methods, kernel methods, deterministics, genetic programs, feature extraction, and/or any other suitable model. Models can be trained, learned, fit, predetermined, calibrated, and/or can be otherwise determined.

In examples, processing a signal can include: filtering, normalizing, extracting signal parameters, transforming (e.g., using Fast Fourier Transform, Fast Pade Transform, other discrete transforms, continuous transforms, etc.), aggregating, statistical analysis, downsampling, fitting, denoising, a combination thereof, and/or otherwise processing a signal. Examples of signal parameters include: maximum signal intensity, signal shape (e.g., area under the curve, full width at half maximum, etc.), relative parameters (e.g., height) between components (e.g., between an analyte component and a lipid component, between an analyte component and a water component, between a lipid component and a water component, etc.), percentage of the signal from blood, echo time, relaxation time (e.g., T2 relaxation, T2* relaxation, T1 relaxation, etc.), and/or any other parameters. In a specific example, multiple received signals, each corresponding to a measurement scan, can be aggregated (e.g., averaging, weighted averaging, etc.), wherein the analyte level can be determined based on the aggregated signal. In another specific example, a signal (e.g., an aggregated signal) can be filtered in the frequency domain (e.g., above or below a threshold frequency). In an example, the analyte level can be determined by determining signal parameters for all or a portion of the processed or unprocessed signal (e.g., a component of the signal corresponding to the analyte), and determining the analyte level based on the signal parameters using a model (e.g., a machine learning model). The model can optionally be trained (e.g., calibrated) in a set of initial experiments with a known analyte level.

Figure 25B:
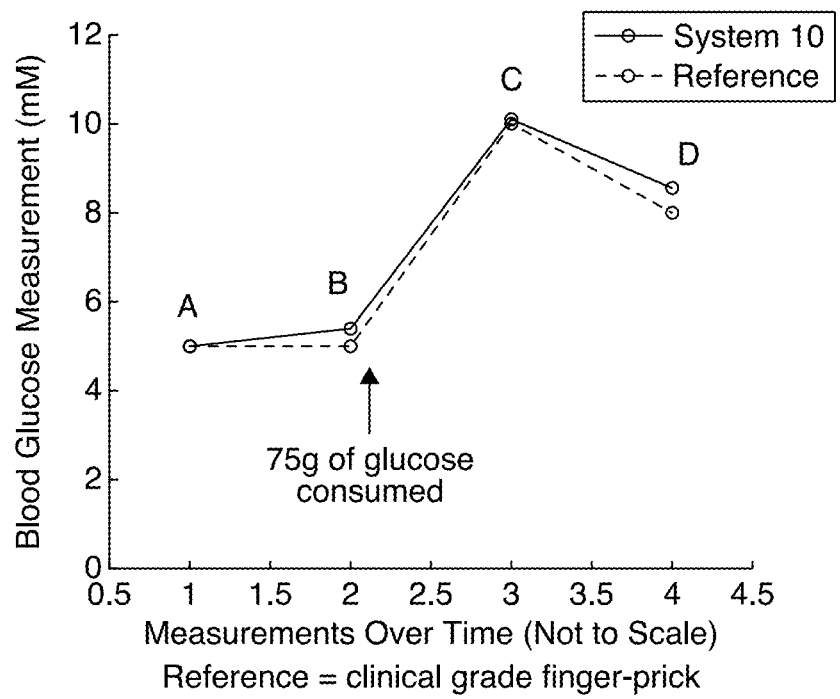
Figure 27:
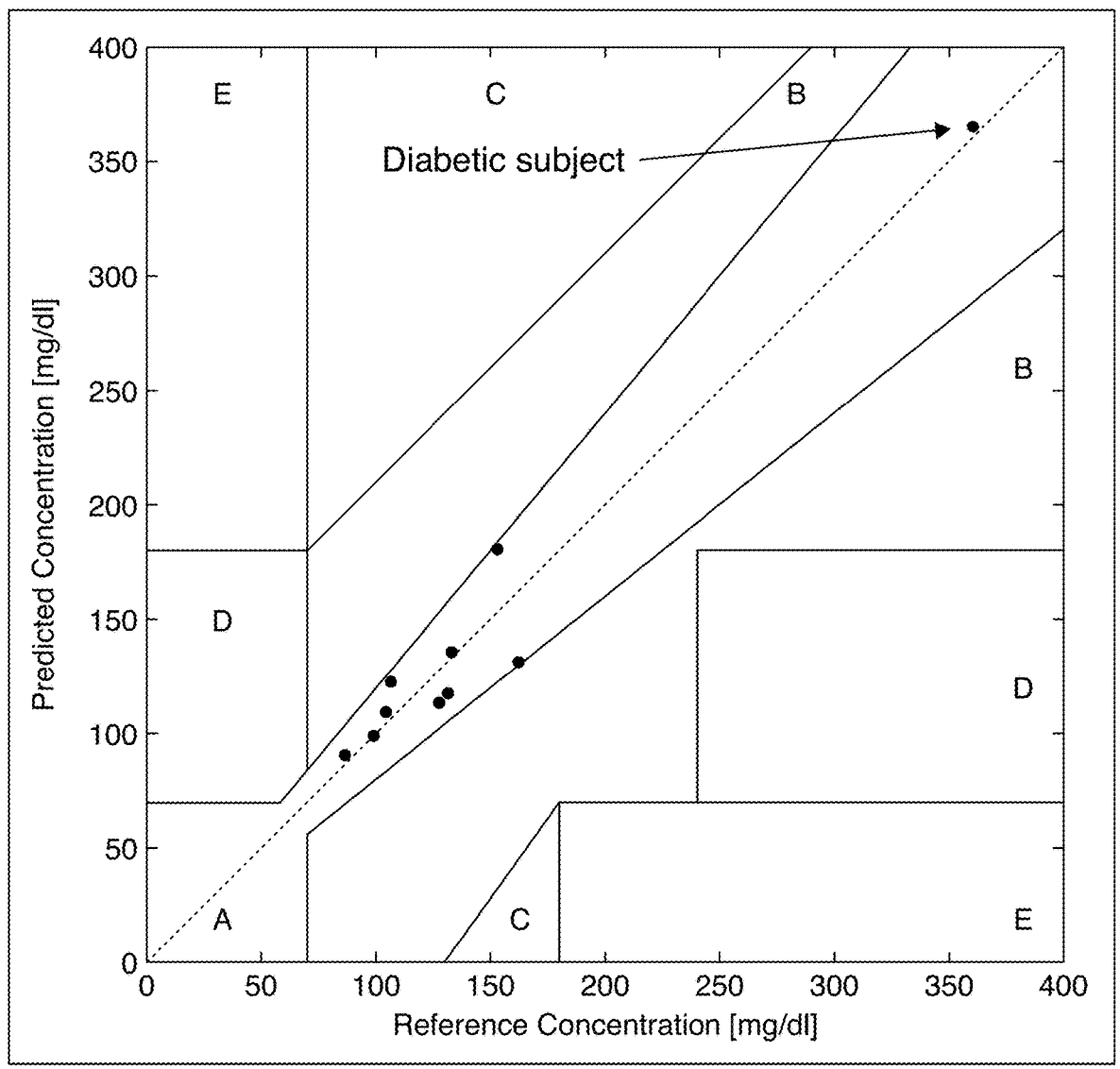
FIG. 27 depicts data from 8 subjects who underwent a study protocol measuring their blood glucose using the FDA gold standard device compared to the system 10 measurement (e.g., with no calibration of the system with a reference finger prick). The signal from the system 10 (e.g., a direct measurement of glucose) responds with blood-glucose concentration. This study included a diverse set of subjects, showing high performance (sex, ethnicity).

Examples of analyte level data are shown in FIG. 25B and FIG. 27.

However, signals can be otherwise processed.

6. Specific Examples

A numbered list of specific examples of the technology described herein are provided below. A person of skill in the art will recognize that the scope of the technology is not limited to and/or by these specific examples.

Specific Example 1. A nuclear magnetic resonance (NMR) system, comprising: a set of magnets producing a magnetic field over a region of interest within a bore configured to receive a finger of a user; a transmitter; a receiver comprising a surface coil, wherein a central axis of the surface coil intersects with a pulp of the finger; and a processing system configured to: using the transmitter, transmit an electromagnetic pulse sequence; using the receiver, sample a receive signal; and determine a blood analyte concentration in the finger based on the receive signal.

Specific Example 2. The NMR system of Specific Example 1, further comprising a sample interface configured to position a surface of the pulp of the finger within a threshold distance of the surface coil.

Specific Example 3. The NMR system of Specific Example 2, wherein the threshold distance is less than 5 mm.

Specific Example 4. The NMR system of Specific Example 2, wherein a susceptibility of the sleeve is within 20% of a susceptibility of the finger.

Specific Example 5. The NMR system of any of Specific Examples 1-4, wherein the surface coil comprises a loop coil of between 2 and 5 turns.

Specific Example 6. The NMR system of any of Specific Examples 1-5, further comprising a set of button shims retained within pockets of a sleeve, wherein the sleeve is positioned within the bore.

Specific Example 7. The NMR system of any of Specific Examples 1-6, wherein the region of interest is nonspherical.

Specific Example 8. The NMR system of any of Specific Examples 1-7, wherein a length of the region of interest along the central axis of the surface coil is less than a length of the region of interest along an axis perpendicular to the central axis of the surface coil.

Specific Example 9. The NMR system of any of Specific Examples 1-8, wherein the set of magnets comprise an array of magnets arranged around the bore, wherein a width of the bore along a first axis is greater than a height of the bore along a second axis, the second axis perpendicular to the first axis; wherein the first axis is parallel to the central axis of the surface coil; wherein the second axis is perpendicular to a longitudinal axis of the bore.

Specific Example 10. The NMR system of any of Specific Examples 1-9, wherein the blood analyte comprises glucose.

Specific Example 11. A nuclear magnetic resonance (NMR) system, comprising: a set of magnets supported by the housing, the magnets producing a magnetic field over a region of interest within a bore configured to receive a finger of a user; a set of coils comprising: a transmitter, a set of gradient coils, and a receiver; and a processing system communicatively coupled to the set of coils, the processing system configured to: using the transmitter, transmit a pulse sequence; using the set of gradient coils, transmit a sequence of gradient pulses configured to select a target region of the finger; using the receiver, sample a receive signal; and determine a blood analyte concentration in the target region of the finger based on the receive signal.

Specific Example 12. The NMR system of Specific Example 11, wherein a proximal-distal axis of the finger is approximately parallel to and offset from a longitudinal axis of the bore.

Specific Example 13. The NMR system of any of Specific Examples 11-12, wherein the target region comprises at least one of the dermis or the hypodermis of a pulp of the finger.

Specific Example 14. The NMR system of any of Specific Examples 11-13, wherein the set of gradient coils comprises three gradient coils corresponding to three directions, wherein the target region comprises a voxel, wherein the target region of the finger comprises a voxel, wherein a width of the voxel along a dorsal-palmar axis of the finger is less than a length of the voxel along a radial-ulnar axis of the finger and is less than a length of the voxel along a proximal-distal axis of the finger.

Specific Example 15. The NMR system of any of Specific Examples 11-14, wherein a location of the target region is determined based on a calibration signal acquired in a calibration scan.

Specific Example 16. The NMR system of any of Specific Examples 11-15, wherein the set coils further comprise a set of shield coils configured to shield the magnetic field generated by the set of gradient coils.

Specific Example 17. The NMR system of any of Specific Examples 11-16, further comprising an active shim coil, wherein the transmitter, the active shim coil, and the set of gradient coils are arranged in a set of layers as nested coils.

Specific Example 18. The NMR system of Specific Example 17, wherein, for each layer in the set of layers, a width of the layer in a first dimension is greater than a width of the layer in a second dimension.

Specific Example 19. The NMR system of any of Specific Examples 11-18, wherein the receiver comprises a surface coil, wherein a gap between the surface coil and a surface of the appendage is less than 10 mm.

Specific Example 20. The NMR system of any of Specific Examples 11-19, wherein the blood analyte comprises at least one of glucose or lactate.

Specific Example 21. A nuclear magnetic resonance (NMR) method, comprising: transmitting a sequence of electromagnetic pulses using a transmit coil, the sequence of electromagnetic pulses comprising: an excitation pulse configured to excite a finger of a user; a first set of refocusing pulses; and a second set of refocusing pulses; transmitting a sequence of gradient pulses using a set of gradient coils, wherein each gradient pulse in the sequence of gradient pulses is transmitted approximately concurrently with a refocusing pulse in the second set of refocusing pulses, wherein the sequence of gradient pulses is configured to select a target region of the finger; sampling a receive signal using a surface coil; and determining a blood analyte concentration in the target region of the finger based on the receive signal.

Specific Example 22. The NMR method of Specific Example 21, wherein the set of gradient coils comprises three gradient coils corresponding to three directions.

Specific Example 23. The NMR method of Specific Example 22, wherein the second set of refocusing pulses comprises three pairs of refocusing pulses, wherein the sequence of gradient pulses comprises three pairs of gradient pulses, each pair of gradient pulses corresponding to a different direction.

Specific Example 24. The NMR method of any of Specific Example 22-23, wherein the target region of the finger comprises a voxel, wherein a width of the voxel along a dorsal-palmar axis of the finger is less than a length of the voxel along a radial-ulnar axis of the finger and is less than a length of the voxel along a proximal-distal axis of the finger.

Specific Example 25. The NMR method of Specific Example 24, wherein the width of the voxel is less than 5 mm.

Specific Example 26. The NMR method of any of Specific Examples 21-25, wherein the finger is positioned within a bore defined by an array of magnets, wherein a central axis of the surface coil intersects with a pulp of the finger, wherein a width of the bore along the central axis of the surface coil is greater than a height of the bore.

Specific Example 27. The NMR method of Specific Example 26, wherein a proximal-distal axis of the finger is approximately parallel to and offset from a longitudinal axis of the bore.

Specific Example 28. The NMR method of any of Specific Examples 21-27, wherein the target region is determined based on at least one of lipid content or water content in the target region.

Specific Example 29. The NMR method of any of Specific Examples 21-28, wherein a loop time for the first set of refocusing pulses is less than 20 ms and a loop time for the second set of refocusing pulses is less than 20 ms.

Specific Example 30. The NMR method of any of Specific Examples 21-29, wherein the blood analyte comprises glucose.

Specific Example 31. A nuclear magnetic resonance (NMR) system, comprising: a set of permanent magnets producing a magnetic field in a finger of a user; a set of coils comprising a transmit coil, a set of gradient coils, and a surface coil; and a processing system in communication with the set of coils, wherein the processing system is configured to: using the transmit coil, transmit a sequence of electromagnetic pulses comprising: an excitation pulse configured to excite the finger and a set of refocusing pulses; using the set of gradient coils, transmit a sequence of gradient pulses concurrent with a subset of the set of refocusing pulses, wherein the sequence gradient pulses are configured to select a target region of a pulp of the finger; using the surface coil, sample a receive signal; and determine a blood analyte concentration in the target region of the finger based on the receive signal.

Specific Example 32. The NMR system of claim 11, wherein a central axis of the surface coil intersects with the pulp of the finger.

Specific Example 33. The NMR system of any of Specific Examples 31-32, wherein a gap between the surface coil and a surface of a pulp of the finger is less than 10 mm.

Specific Example 34. The NMR system of any of Specific Examples 32-33, wherein the set of permanent magnets comprise an array of permanent magnets defining a bore, wherein a width of the bore along the central axis of the surface coil is greater than a height of the bore.

Specific Example 35. The NMR system of Specific Example 34, wherein a proximal-distal axis of the finger is positioned approximately parallel to and offset from a longitudinal axis of the bore.

Specific Example 36. The NMR system of any of Specific Examples 31-35, wherein the set of refocusing pulses comprises a train of non-selective refocusing pulses and a train of selective refocusing pulses, wherein the sequence of gradient pulses is transmitted concurrently with the train of selective refocusing pulses.

Specific Example 37. The NMR system of any of Specific Examples 31-36, wherein the set of gradient coils comprises three gradient coils corresponding to three directions, wherein the target region of the finger comprises a voxel, wherein a width of the voxel along a dorsal-palmar axis of the finger is less than a length of the voxel along a radial-ulnar axis of the finger and is less than a length of the voxel along a proximal-distal axis of the finger.

Specific Example 38. The NMR system of any of Specific Examples 31-37, wherein a loop time for the set of refocusing pulses is less than 20 ms.

Specific Example 39. The NMR system of any of Specific Examples 31-38, wherein the receive signal is sampled based on an echo time greater than 50 ms and less than 200 ms.

Specific Example 40. The NMR system of any of Specific Examples 31-39, wherein the blood analyte comprises at least one of glucose or lactate.

As used herein, "substantially" or other words of approximation (e.g., "about," "approximately," etc.) can be within a predetermined error threshold or tolerance of a metric, component, or other reference (e.g., within +/−0.001%, +/−0.01%, +/−0.1%, +/−1%, +/−2%, +/−5%, +/−10%, +/−15%, +/−20%, +/−30%, any range or value therein, of a reference).

All references cited herein are incorporated by reference in their entirety, except to the extent that the incorporated material is inconsistent with the express disclosure herein, in which case the language in this disclosure controls.

Different subsystems and/or modules discussed above can be operated and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A nuclear magnetic resonance (NMR) system, comprising:
    a set of magnets producing a magnetic field over a region of interest within a bore configured to receive a finger of a user, wherein the set of magnets comprises an array of magnets arranged around the bore;
    a transmitter;
    a receiver comprising a surface coil, wherein a central axis of the surface coil intersects with a pulp of the finger, wherein a width of the bore along a first axis is greater than a height of the bore along a second axis, the second axis perpendicular to the first axis, wherein the first axis is parallel to the central axis of the surface coil, wherein the second axis is perpendicular to a longitudinal axis of the bore; and
    a processing system configured to:
        using the transmitter, transmit an electromagnetic pulse sequence;
        using the receiver, sample a receive signal; and
        determine a blood analyte concentration in the finger based on the receive signal.

2. The NMR system of claim 1, further comprising a sample interface configured to position a surface of the pulp of the finger within a threshold distance of the surface coil.

3. The NMR system of claim 2, wherein the threshold distance is less than 5 mm.

4. The NMR system of claim 2, wherein a susceptibility of the sample interface is within 20% of a susceptibility of the finger.

5. The NMR system of claim 1, wherein the surface coil comprises a loop coil of between 2 and 5 turns.

6. The NMR system of claim 1, further comprising a set of button shims retained within pockets of a sleeve, wherein the sleeve is positioned within the bore.

7. The NMR system of claim 1, wherein the region of interest is nonspherical.

8. The NMR system of claim 7, wherein a length of the region of interest along the central axis of the surface coil is less than a length of the region of interest along an axis perpendicular to the central axis of the surface coil.

9. The NMR system of claim 1, wherein the blood analyte comprises glucose.

* * * * *